1

(12) United States Patent
Bringe et al.

(10) Patent No.: US 7,704,540 B2
(45) Date of Patent: Apr. 27, 2010

(54) SOY COMPOSITIONS HAVING IMPROVED ORGANOLEPTIC PROPERTIES AND METHODS OF GENERATION

(75) Inventors: Neal A. Bringe, St. Charles, MO (US); Robert G. Orth, Gerald, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1114 days.

(21) Appl. No.: 11/177,943

(22) Filed: Jul. 8, 2005

(65) Prior Publication Data
US 2006/0021090 A1   Jan. 26, 2006

Related U.S. Application Data

(60) Provisional application No. 60/521,846, filed on Jul. 9, 2004.

(51) Int. Cl.
| A23L 1/31 | (2006.01) |
| A23D 9/013 | (2006.01) |
| A23L 1/22 | (2006.01) |
| C12N 5/04 | (2006.01) |
| A01H 1/00 | (2006.01) |
| A01H 5/00 | (2006.01) |

(52) U.S. Cl. ................... 426/574; 800/262; 800/263; 800/312; 800/264; 435/415; 426/531; 426/534

(58) Field of Classification Search .......... None
See application file for complete search history.

(56) References Cited

U.S. PATENT DOCUMENTS

| 4,677,247 A | 6/1987 | Kitamura ................. 800/1 |
| 5,530,183 A | 6/1996 | Fehr et al. ............... 800/200 |
| 5,534,425 A | 7/1996 | Fehr et al. ............. 435/172.1 |
| 5,710,365 A | 1/1998 | Kerr et al. ............... 800/200 |
| 5,710,369 A | 1/1998 | Fehr et al. ............... 800/200 |
| 5,714,668 A | 2/1998 | Fehr et al. ............... 800/200 |
| 5,714,669 A * | 2/1998 | Fehr et al. ............... 800/312 |
| 5,714,670 A | 2/1998 | Fehr et al. ............... 800/200 |
| 5,727,689 A | 3/1998 | Anderson et al. ........ 209/139.1 |
| 5,763,745 A | 6/1998 | Fehr et al. ............... 800/200 |
| 5,777,080 A | 7/1998 | Boatright ................ 530/378 |
| 5,850,030 A | 12/1998 | Fehr et al. ............... 800/312 |
| 5,981,781 A | 11/1999 | Knowlton ............... 554/224 |
| 5,986,118 A | 11/1999 | Fehr et al. ............... 554/224 |
| 6,133,509 A * | 10/2000 | Fehr et al. ............... 800/312 |
| 6,171,640 B1 * | 1/2001 | Bringe .................... 426/656 |
| 6,184,442 B1 | 2/2001 | Nickell .................. 800/312 |
| 6,355,296 B1 | 3/2002 | Altemueller et al. ........ 426/656 |
| 6,369,302 B1 | 4/2002 | Matson .................. 800/312 |
| 6,444,874 B1 | 9/2002 | Duvick et al. ............ 800/279 |
| 6,566,134 B2 | 5/2003 | Bringe .................... 435/410 |
| 6,653,534 B1 | 11/2003 | Conway ................ 800/312 |
| 2002/0102339 A1 | 8/2002 | Akashe ................. 426/507 |
| 2004/0005346 A1 | 1/2004 | Boatright ................ 424/439 |
| 2004/0107460 A1 | 6/2004 | Fillatti et al. ............. 800/281 |
| 2004/0161513 A1 | 8/2004 | Akashe ................. 426/422 |
| 2005/0138681 A1 | 6/2005 | Takahashi et al. ........... 800/278 |
| 2006/0062894 A1 | 3/2006 | Smith et al. ............. 426/656 |

FOREIGN PATENT DOCUMENTS

| WO | WO 88/06919 | 9/1988 |
| WO | WO 01/06866 | 2/2001 |
| WO | WO 2004/001000 | 12/2003 |
| WO | WO 2006/039136 | 4/2006 |

OTHER PUBLICATIONS

Inouye et al Journal of Agricultural and Food Chemistry 2002 50:1652-1658, provided by Applicant in IDS.*
Anai et al., "Identification of corresponding genes for three low-alpha-linolenic acid mutants and elucidation of their contribution to fatty acid biosynthesis in soybean seed," *Plant Science* 168:1615-1623, 2005.
Bilyeu and Beuselinck, "Molecular genetics of low linolenic acid soybeans," *10th Biennial Conference Of The Cellular And Moecular Biology Of The Soybean*, 2004.
Bilyeu and Beuselinck, "The contribution of multiple genes to one trait: Linolenic acid production in soybean seeds," *Plant Genetics 2003: Mechanisms of Genetic Variation, American Society of Plant Biologists*, Abstract 50, XP009060561, 2003.
Bilyeu et al., "Three microsomal omega-3 fatty-acid desaturase genes contribute to soybean linolenic acid levels," *Crop Sci*, 43(5):1833-1838, 2003.
Byrum, et al., "Alteration of the omega-3 fatty acid desaturase gene is associated with reduced linolenic acid in the A5 soybean genotype," *Theor. Appl. Genet.*, 94:356-359, 1997.
Fehr et al., "Inheritance of reduced linolenic acid content in soybean genotypes a16 and a17," *Crop Sci.*, 32:903-906, 1992.
Jourdren et al., "Specific molecular marker of the genes controlling linolenic acid content in rapeseed," *Theor Appl. Genet*, 93:512-518, 1996.
Knutzon et al., "Modification of Brassica ssed oil by antisense expression of a stearoyl-cyl carrier protein desaturase gene," *Proc. Natl. Acad. Sci. USA*, 89:2624-2628, 1992.
Lui and White, "Oxidative stability of soybean oils with altered fatty acid composition," *J. Am. Oil Chem. Soc.*, 69:528-532, 1992.
O'Brien, "Fats and oils: formulating and processing for applications," Second Edition, *CRC Press*, 14-15, 2003.
Primomo et al., "Inheritance and interaction of low palmitic and low linolenic soybean," *Crop Sci.*, 42:31-36, 2002.
Rahman and Takagi, "Inheritance of reduced linolenic acid content in soybean seed oil," *Theor. Appl. Genet.*, 94:299-302, 1997.
Rahman et al., "Combining ability in loci for high oliec and low linolenic acids in soybean," *Crop Sci*, 41:26-29.

(Continued)

*Primary Examiner*—Anne Marie Grunberg
*Assistant Examiner*—Brent Page
(74) *Attorney, Agent, or Firm*—Chunping Li, Esq.; Sonnenschein Nath & Rosenthal LLP

(57) ABSTRACT

The present invention provides soy meat compositions with improved organoleptic properties and methods of identifying soybeans with improved organoleptic qualities. The invention also provides methods for producing soy compositions with improved organoleptic properties and for creating plants producing soybeans with such characteristics.

20 Claims, No Drawings

OTHER PUBLICATIONS

Rahman et al., "Genetic relationships of soybean mutants for different linolenic acid contents," *Crop Sci.*, 38:702-706, 1998.

Rennie and Tanner, "New allele at the fan locus in the soybean line A5," *Crop Sci*, 31:297-301, 1991.

Ross et al., "Agronomic and seed traints of 1%-linolenate soybean genotypes," *Crop Sci.*, 40:383-386, 2000.

Stoisin et al., "Inheritance of low linolenic acid level in the soybean line RG10," *Crop Sci.*, 38:1441-1444, 1998.

Walker et al., "Reduced-linolenate content associations with agronomic and seed traits of soybean," *Crop Sci*, 38:352-255, 1998.

Wilcox and Cavins, "Gene symbol Assigned for linolenic acid mutant in the soybean," *J. Heredity*, 78:410, 1987.

Wilcox and Cavins, "Inheritance of low linolenic acid content of the seed of a mutant of *Glycine max*," *Theor. Appl. Genet.*, 71:74-78, 1985.

Yadev et al., "Cloning of higher plant ω-3 fatty acid desaturases," *Plant Physiol.*, 103:467-476, 1993.

Poysa and Buzzell, "AC X790P soybean," *Can. J Plant Sci.*, 81:447-448, 2001.

Boue et al., "Effect of soybean lipoxygenase on volatile generation and inhibition of Aspergillus flavus mycelial growth," *J Agric Food Chem* 53(12):4778-83, 2005.

Takahashi et al., "Accumulation of high levels of free amino acids in soybean seeds through integration of mutations conferring seed protein deficiency," *Planta* 217(4):577-86, 2003.

Boatright and Lei, "Compounds contributing to the 'beany' odor of aqueous solutions of soy protein isolates," *J. Food Sci.*, 64:667-670, 1999.

Boatright et al., "Effect of pro-oxidants on the occurrence of 2-pentyl pyridine in soy protein isolate," *JAOCS*, 75:1379-1383, 1998.

Boatright, 2003, poster 45C-26, IFT annual meeting, Chicago.

Dahuja and Madaan, "Off-flavour development in soybeans: comparative role of some antioxidants and related enzymes," *Sci. Food Agric.*, 84:547-550, 2004.

Feng, Cornell University Ph.D. Dissertation, 2000.

Frankel, "Hydroperoxide decomposition," chapter 4 in *Lipid Oxidation*, The Oily Press, Dundee, Scotland, 1998.

Freese, "Sweet beans, sweet profit," *Successful Farming*, 97:7, 1999.

Hajika et al., "A line lacking all the seed lipoxygenase isozymes in soybean [glycine max (L.) Merrill] induced by gamma-ray irradiation," *Jpn J. Breed.*, 41:507-509, 1991.

Hao et al., "Effects of lipoxygenase null genes of soybean in controlling beany-flavor of soymilk and soyflour," *Agricultural Sciences in China*, 1:965-971, 2002.

Husson et al., "Induction and localization of a lipoxygenase from *Fusarium* proliferatum" *J. Molecular Catalysis B: Enzymatic*, 5:159-163, 1998.

Inouye et al., "Deodorization of soybean proteins by enzymatic and physicochemical treatments", *J Agric Food Chem* 50:1652-1658, 2002.

Joshi, "Physical aspects of color in foods," *Chemical Innovation*, 19-24, 2000.

Kim et al., "Formation of 2-pentylpyridine from the thermal interaction of amino acids and 2,4-decadienal," *J. Agric. Food Chem.*, 44:3906-3908, 1996.

Kobayashi et al., 'aroma consittuents of soybean [glycine max (L.) Merril] milk lacking lipoxygenase isozymes,'*J. Agric. Food Chem.*, 43:2449-2452, 1995.

Lei and Boatright, "Factors influencing the occurrence of methanethiol in aqueous slurries of soy protein concentrates," *J. Food Sci.*, 68:1568-1572, 2003.

Lin and Blank, "Odorants generated by thermally induced degradation of phospholipids," *Agric. Food Chem.*, 51:4364-4369, 2003.

Maheshwari et al., "Characterization and application of procine liver aldehyde oxidase in the off-flavor reduction of soy proteins," *J. Agric. Food Chem.*, 45:2488-2494, 1997.

Minor et al., "Developing soybean varieties with genetic resistance to *Phomopsis* spp.," *JAOCS*, 72:1431-1434, 1995.

O'Keefe et al., "Temperature effect on binding of volatile flavor compounds to soy protein in aqueous model systems," *J. Food Sci.*, 56:802-806, 1991.

Salete et al., "Effect of harvesting and drying conditions on chlorophyll levels of soybean (glycine max L. Merr),"*J. Agric. Food Chem.*, 51:1634-1639, 2003.

Samoto et al., "Improvement of the off-flavor of soy protein isolate be removing oil-body assicated proteins and polar lipids," *Biosci. Biotechnol. Biochem.*, 62:935-940, 1998.

Sinnecker et al., "Relationship between color (instrumental and visual) and chlorophyll contents in soybean seeds during ripening," *J. Agric. Food Chem.*, 50:3961-3966, 2002.

Stawicki et al., "The effect of microflora on the formation of odors in grain during storage" *Annals de Technologie Agricole* 22(3):449-476, 1973, Abstract.

Torres-Penaranda and Reitmeirer, "Sensory descriptive analysis of soymilk," *J. Food Sci.*, 66:352-356, 2001.

Warner et al. "Effect of oleic and linoleic anids on the production of deep-fried odor in heated triolein and trilinolein," *J. Agric. Food Chem.*, 49:899-905, 2001.

Wilson, In: *Lipoxygenase and Lipoxygenase Pathway Enzymes*, Piazza (Ed.), 209-225, 1996.

Wolfe and Cowan, In: *Soybean as a Food Source*, CRC Press, Inc., Boca Raton, Florida, 87-97, 1975.

Wurzenberger and Grosch, "The formation of 1-octen-3-ol from the 10-hydroperoxidase isomer of linoleic acid by a hydroperoxide lyase in mushrooms (psalliota bispora)," *Biochim. Biophys. Acta*, 794:25-30, 1984.

Zhou and Boatright, "Formation of 2-pentyl pyridine during processing of soybean protein isolates as affected by pH," *Food Sci.*, 64:852-854, 1999.

Zhou and Boatright, "Precursors for formation of 2-pentyl pyridine in processing of soybean protein isolates," *J. Food Sci.*, 65:1155-1159, 2000.

Zhou et al., "Binding properties of 2-pentyl pyridine to soy protein as measured by solid phase mocroextraction," *J. Food Sci.*, 67:142-145, 2002.

Blasi et al., "Soybean Hulls: Composition and Feeding Value for Beef and Dairy Cattle," Kansas State Agricultural Experiment Station and Cooperative Extension Service, Kansas State University, pp. 1-16, 2000.

* cited by examiner

SOY COMPOSITIONS HAVING IMPROVED ORGANOLEPTIC PROPERTIES AND METHODS OF GENERATION This application claims the priority of U.S. Provisional Patent Appl. Ser. No. 60/521,846, filed Jul. 9, 2004, the entire disclosure of which is specifically incorporated herein by reference.

BACKGROUND OF THE INVENTION

1. Field of the Invention

The invention relates to the field of nutrition and food sciences. In particular, the invention relates to soy meat compositions with improved organoleptic properties such as decreased odor and methods for the use and production thereof.

2. Description of Related Art

Soybeans provide high quality proteins that provide health benefits for humans (Hermansen et al., 2003; Bazzano et al., 2001; Food and Drug Administration, 1999). The demand for soybeans to make soy foods had not gone up as much as expected in last three decades (Wolfe and Cowan, 1975 and SoySource, The United Soybean Board 1999). This is in-part because of the undesirable odor associated with soy products (McLeod and Ames, 1988 and Freese, 1999). The undesirable soybean odor is commonly described as "beany." Components that impart beany characteristic to soybeans include many volatile fatty acids, aliphatic carbonyls, amines, alcohols, aldehydes, and furans derived from the action of enzymes on various compounds found in soybeans and their further oxidation that is caused by many mechanisms (Wolfe and Cowan, 1975; Sessa and Rackis, 1977).

Kobayashi et al. (1995) concluded the main contributors to the odor of uncooked soymilk were (trans, trans)-2,4-nonadienal, (trans, trans)-2,4-decadienal, hexanal, 2-pentyl furan, 1-octen-3-one, (trans)-2-nonenal, and (trans, cis)-2,4-nonadienal. The strongest odors extracted from heat-treated soymilk were identified as (trans, trans)-2,4 decadienal and n-hexanal (Feng, Cornell University Ph.D. Dissertation, 2000). The formation of (trans, trans)-2,4 decadienal take place at a slow rate at room temperature (Frankel, 1988), however this reaction is enhanced because of thermal degradation during soybean processing under hot conditions (Lin, 2003). Other contributors to odors were (trans)-4,5-epoxy-(E)-2-decenal (formed from 2,4 decadienal), (trans, cis)-2,6-nonadienal, (trans)-2-nonenal, (trans, trans)-2,4-nonadienal, 2,4 nonadienal, maltol, vanillin and β-damascenone. The most powerful odorants in soymilk determined by the minimum headspace volume required to detect by olfactometry, were hexanal, acetaldehyde, methanethiol, dimethyl trisulfide, and 2-pentyl furan (Boatright, 2002).

The strongest odorants in soy protein isolates were identified as dimethyl trisulfide, (trans, trans)-2,4-decadienal, 2-pentyl pyridine, (trans, trans)-2,4,-nonadienal, hexanal, acetophenone, and 1-octen-3-one (Boatright and Lei, 1999). The mechanism of formation of methanethiol and dimethyl trisulfide involves free radicals formed by lipid oxidation (Lei and Boatright, 2003) and products of enzymes such as cysteine synthase (Boatright, 2003, poster 45C-26, IFT annual meeting, Chicago).

The formation of 2-pentyl pyridine occurs from a spontaneous reaction between 2,4 decadienal and ammonia at room temperature. Free amino acids arginine, lysine, asparagine and glutamine increase 2-pentyl pyridine formation probably by providing ammonia during soy protein processing. (Zhou and Boatright, 2000; Kim et al., 1996). Free amino acids can also form other undesirable products. High temperature exposure of asparagine and glucose results in the formation of acrylamide (Jung et al., 2003). Arginine exposed at cooking temperatures can form mutagens (Knize et al., 1994). Free arginine was enriched in soybeans lacking both β-conglycinins and glycinins (Takahashi et al., 2003).

Once formed, odors are difficult to remove from soy ingredients because they are associated with proteins (Franzen and Kinsella, 1974). The quality of natural flavors added to soy foods are also altered unfavorably because some of the odors bind to soy protein. Carbonyl compounds and 2-pentyl pyridine bound with greater affinity to glycinin fractions than β-conglycinin fractions (Zhou et al., 2002; O'Keefe et al., 1991). The extraction of oil-body-associated proteins and polar lipids significantly reduced the quantity of odors associated with soy protein isolate (Samoto et al., 1998).

Textures created by protein-protein interactions can have more effect on flavor intensity than the in-nose odor concentration (Weel et al., 2002). Soy proteins can contribute to the poor organoleptic quality of soy beverages by forming insoluble aggregates and chalky mouthfeel (Skarra and Miller, 2002). Among the main soy proteins, glycinins are more sensitive to pH and $Ca^{+2}$-induced insolubilization (Yuan, 2002) and soybeans containing a low ratio of glycinins to β-conglycinins are useful for creating soluble soy protein ingredients (U.S. Pat. No. 6,171,640). Lipid oxidation reactions also influence protein solubility. Antioxidants can be added during soy protein isolate manufacture to limit free radical induced oxidation of proteins and improve the yield of soluble protein (U.S. Pat. No. 5,777,080). Some peptides can react during processing with polysaccharides to form antioxidant compounds (Matsumura, 2003).

Color influences perceptions of freshness and taste (Joshi, 2000). Low amounts of reducing sugar and aldehydes formed from lipid oxidation react with amino groups of proteins on heating to form brown pigments by the Maillard's browning reaction (Kwok et al., 1999). Soymilk with a higher content of aldehydes will create a darker, less appealing color after heat processing. On the other hand lipid oxidation during soymilk processing decolorizes yellow pigments in soymilk (Obata and Matsuura, 1997).

Soybeans are refined to improve the flavor by extracting lipids and other components either by alcohol extraction, enzyme treatments, washing protein curds, ultrafiltration of protein and or use of flash vaporization. These processes add to the cost of the soy protein ingredients and typically lower the amounts of healthful components that are bioavailable (for example fiber, oligosaccharides, isoflavones, polyunsaturated fatty acids, tocopherols, phospholipids, bioactive peptides). Processing approaches used to improve the organoleptic properties of soy protein ingredients are limited in effectiveness by odors bound to soy proteins and by conditions that promote odor formation (pH 8-10). Soybeans that lack one to three of the lipoxygenases 1, 2, and 3 were created using mutation breeding to reduce the formation of beany odors (Hajika et al., 1991). Aroma analysis of soymilk and soy flour made from soybeans lacking the three lipoxygenases were found to contain lower amounts of several odors, but higher amounts of 1-octen-3-ol than the parent soybean line containing all three lipoxygenases (Hao et al., 2002). Similar levels of 2,4 decadienal were found in defatted flour and soy protein isolate made from one soybean lacking three lipoxygenases and two other soybean lines (Boatright et al., 1998). Soy foods prepared from soybeans lacking lipoxygenases had improved flavor compared to foods made from control soybeans (Wilson, 1996). Soymilk prepared from soybeans lacking three lipoxygenases was perceived as more bitter than the control, especially after 15 months of seed storage, but this difference was expected to be eliminated by adding sugar (Torres-Penaranda and Reitmeirer, 2001).

Transgenic modifications are proposed to improve the flavor of soybeans by reducing the levels of polyunsaturated fatty acids (U.S. Pat. No. 5,981,781), lipoxygenases (U.S. Patent Appln. 20030074693) and or hydroperoxide lyases (U.S. Pat. No. 6,444,874). Soybeans containing less than 10% polyunsaturated fatty acids and greater than 75% oleic fatty acids yield frying oil that is less tasty compared to frying oil with higher polyunsaturated fatty acids (Warner et al., 2001).

Chemicals such as polyphosphates (U.S. Pat. No. 6,355, 296) can be used to limit off-favor production and improve protein solubility. Other additives such as gallic acid (PCT WO 01/06866) or aldehyde oxidase (Maheshwari et al., 1997) can be used to remove odors.

There is little published information on the effects of natural genetic variations on flavor and color attributes of soybeans. The thiobarbituric acid number for 16 soybean varieties was determined as a measure of lipid oxidation and no correlation was found with the vitamin E content of the soybeans (Dahuja and Madaan, 2004). The amounts of 2-pentyl pyridine and 2,4 decadienal in soy flour and soy protein isolate made from three soybean varieties were determined (Zhou and Boatright, 1999). The effects of drying conditions on the removal of the green pigment, chlorophyll from soybeans were studied (Salete et al., 2003; Sinnecker et al, 2002).

In past decades scientists showed that oils prepared from soybeans lacking lipoxygenases did not have improved oxidative stability. Soybean proteins produced from lipoxygenase null soybeans still contained significant levels of beany taste (Maheshwari et al., 1997).

The first step in making soymilk or soy protein ingredients is to dehull (or decoat) the soybeans to create soybean meats. Hypocotyls may also be separated from the cotyledons. Soybean meats are defined as dehulled soybeans and may or may not include cotyledons. A method for preparing meats is described, for example, in U.S. Pat. No. 5,727,689. One method for dehulling includes, but is not limited to, running seeds between counter-current rollers or a cracking mill and aspirating light weight hulls, leaving the meats. Meats may be soaked in water to produce soymilk or flaked and extracted using hexane as an initial step in making defatted soy flour, soy protein concentrates, soy protein isolates and purified protein fractions, as desired.

The present invention provides a new method to determine the ability of soybean meats to resist production of key odor compounds identified as 2,4 decadienal, hexanal, hexanol and 1-octen-3-ol. These compounds were selected as indicators of the extent of different types of oxidation reactions. Hexanal and hexanol result from the breakdown of hydroperoxide containing compounds (peroxides on 9 and 12 carbon positions of fatty acids) by hydroperoxide lyases and alcohol dehydrogenases. 2,4 decadienal is a breakdown product of the lipoxygenase pathway which is not known to involve hydroperoxide lyases. 1-octen-3-ol is formed by the action of hydroperoxide lyases on hydroperoxides formed on the 10 carbon position of linoleic acid. These compounds can react further by additional processing to form more potent odors. For example, 2,4 decadienal is involved in the formation of 2-pentyl pyridine and 1-octen-3-ol is involved in the formation of 1-octen-3-one.

SUMMARY OF THE INVENTION

In one aspect, the invention provides a soybean meat composition produced from soybeans comprising lipoxygenases 1, 2 and 3, wherein the composition comprises greater than 10% linoleic acid as a percentage of total fatty acids and less than 20 µg of total 2,4 decadienal plus hexanal plus hexanol per gram following oxidation under mild aqueous conditions. The composition may or may not comprise the lipoxygenases, or any combination thereof and may comprise deactivated lipoxygenase. In one embodiment, the composition comprises lipoxygenase-2. In certain embodiments, a composition provided by the invention may comprise less than about 15 µg or less than about 18 µg of total 2,4 decadienal plus hexanal plus hexanol. In further embodiments, the composition may comprise about 6 µg- about 20 µg, about 10 µg-20 µg or about 12-18 µg total 2,4 decadienal plus hexanal plus hexanol. In other embodiments, the composition may comprise less than 4% linolenic acid as percent of total fatty acids, including less than about 3% and from about 1%-4% or about to about 2%- about 4%.

In another embodiment, a composition of the invention may comprise less than 2000 µg per gram free arginine and/or less than 400 µg free asparagine per gram, including less than about 1800 µg per gram free arginine and/or less than about 350 µg free asparagine per gram. Such a composition, in certain embodiments, may comprise about 300 µg-2000 µg per gram free arginine, including about 500-2000, about 1200-1800 and about 1000-2000 µg per gram free arginine. A composition provided by the invention may further, in certain embodiments, comprise from about 50 µg- about 400 µg free asparagine per gram, including about 100-400, 100-350, 200-400, 300-400 and 250-400 µg free asparagine per gram.

In still another embodiment, the compositions provided by the invention may have a color measured as b* value of less than 30 and an L* value greater than 80, as monitored by the CIE-L*a*b* system where L* indicates lightness and b* indicates hue on a blue (−) to yellow (+) axis. In certain embodiments, a composition of the invention may comprise a color measured as b* value of about 18-30, about 20-30, about 25-30 and less than about 25. In further embodiments, a composition provided by the invention may comprise an L* value of, about 80-100, about 80-90 and greater than about 90. In certain embodiments, a composition provided by the invention may comprise less than 8 µg of 1-octen-3-ol content per gram following oxidation under mild aqueous conditions, including less than about 6 µg, less than about 5 µg, from about 1.3- about 8 µg, from about 2- about 8 µg, and from about 4- about 8 µg. A composition provided by the invention may also have greater than 30% of the protein as β-conglycinin and may have less than 25% of the protein as glycinin. Such a composition may be further defined as having greater than about 40% of the protein as β-conglycinin, and having a β-conglycinin content of from about 30%- about 60%, about 40%-60%, about 35%-55%, and about 30%- about 50% of the protein. Such a composition may be further defined as having a glycinin content of less than about 20%, 15% and 10%, and may comprise from about 0%-25%, 5%-20%, 1%-25%, and about 10-25% of the protein as glycinin.

In another aspect of the invention, a soybean meat composition is provided having greater than 30% of the protein as β-conglycinin and less than 25% of the protein as glycinin, less than 5,000 µg per gram of free arginine, and less than 900 µg per gram free asparagine. Such a composition may comprise, in certain embodiments, from about 300-5,000 µg per gram, from about 1,000-5,000 µg per gram, from about 3,000-5,000 µg per gram, from about 1,000-4,000 µg per gram, and from about 500-2,000 µg per gram of free arginine. Such a composition may comprise, in certain embodiments, less than 400 µg per gram free asparagine, from about 50-400 µg per gram, from about 100-400 µg per gram, from about 100-700

µg per gram, and from about 200-900 µg per gram free asparagine. In one embodiment, the composition has less than 2,000 µg per gram of free arginine and less than 400 µg per gram free asparagine.

In another embodiment, the composition provided comprises less than 4 µg per gram 1-octen-3-ol content following oxidation under mild aqueous conditions, including less than about 3 µg, from about 1.3 µg-3 µg, from about 1.3 µg-4 µg and from about 2 µg-4 µg per gram. In still further embodiments, the composition has a linolenic acid concentration between 1% and 14% of the total fatty acids, including about 3-14%, about 5-14%, about 1.5%-12%, about 3-12% and about 7-14%. In yet another embodiment, the composition has a linoleic acid concentration between 10% and 60% of the total fatty acids, including between about 10% and 50%, between about 10% and 40%, between about 15% and 60%, between about 20% and 50%, and between about 20% and 60%.

In certain embodiments, a soybean meat composition provided by the invention may be defined as lacking one or more lipoxygenases. In one embodiment, a soybean meat composition provided by the invention may be defined as lacking lipoxygenase-2. In further embodiments, any combination of lipoxygenase-1, lipoxygenase-2 and/or lipoxygenase-3 are absent, including any two or all three of these lipoxygenases. A composition of the invention may also be defined as having a color characterized by b* value less than 30 and an L* value greater than 80 as monitored by the CIE-L*a*b* system where L* indicates lightness and b* indicates hue on a blue (–) to yellow (+) axis. In still other embodiments, a composition provided by the invention may comprise 67-69 mg lysine per gram of protein, may comprise 72-80 mg arginine per gram of protein and/or may comprise 28-30 mg histidine per gram of protein.

In yet another aspect, the invention provides a method of analyzing the odor producing properties of a soybean comprising determining the level of at least one compound selected from the group consisting of 2,4 decadienal, hexanol, hexanal, and 1-octen-3-ol. In one embodiment, the method may comprise determining the level of the compound comprises incubating a mixture of about 1 part of soybean seed flour and about 4 parts of water for a period in the range of about 1 to about 40 minutes and quantifying amounts of at least one compound selected from the group consisting of 2,4 decadienal, hexanol, hexanal, and 1-octen-3-ol and combinations thereof, using deuterated standards for hexanal, hexanol and decadienal. The soybean seed flour may be made from dehulled soybeans.

In still yet another aspect, the invention provides a method of obtaining a soybean variety producing soybeans and soybean meats with decreased odor producing properties comprising measuring the level of at least one compound selected from the group consisting of 2,4 decadienal, hexanol, hexanal, 1-octen-3-ol, and any combination thereof in one or more soybeans or soybean meats from first and second soybean varieties and selecting the variety producing seeds with lower levels of the compound. The method may further comprise crossing a plant of the selected variety with a different plant to produce progeny and measuring the level of at least one compound selected from the group consisting of 2,4 decadienal, hexanol, hexanal, 1-octen-3-ol, and any combination thereof in one or more soybeans or soybean meats from the progeny.

In still yet another aspect, the invention provides a method for selecting a soybean variety that resists fungal contamination comprising selecting a variety that comprises less than 5 µg 1-octen-3-ol per gram of seed as measured by incubating a mixture of about 1 part of soybean seed flour and about 4 parts of water for a period in the range of about 1 to about 40 minutes and measuring the 1-octen-3-ol.

In still yet another aspect, the invention provides a seed of the soybean plant designated 0119149, representative seed of which have been deposited under ATCC Accession No. PTA-6197. The invention further provides a soybean plant 0119149 or parts thereof produced by growing such seed. Such a plant of the invention may comprise a transgene. In still other embodiments, the invention provides a method of producing a soybean plant derived from the soybean plant 0119149, the method comprising the steps of: (a) preparing a progeny plant derived from soybean plant 0119149 by crossing a plant of the soybean plant 0119149 with a second soybean plant, wherein a sample of the seed of the soybean plant 0119149 was deposited under ATCC Accession No. PTA-6197; (b) crossing the progeny plant with itself or a second plant to produce a seed of a progeny plant of a subsequent generation; (c) growing a progeny plant of a subsequent generation from the seed and crossing the progeny plant of a subsequent generation with itself or a second plant; and (d) repeating steps (b) and (c) for an addition 3-10 generations to produce an inbred soybean plant derived from the soybean plant 0119149.

In still yet another aspect, the invention provides soybeans with improved organoleptic properties (i.e. soybeans with improved taste, color, odor and mouth feel properties), following oxidation under mild aqueous conditions. Also provided are soybeans with lighter color to improve the organoleptic properties of soybeans. Further provided are soybeans with low amounts of free arginine and asparagine to improve the organoleptic properties of soybeans. In another embodiment, soybeans with reduced levels of linoleic and linolenic acids are provided to improve organoleptic properties.

A soybean plant provided by the invention may comprise, in one embodiment, one or more transgenes. Examples include a gene conferring herbicide resistance that will produce plants with herbicide resistance and a gene conferring insect resistance.

In accordance with the invention, soybean seed are provided containing lipoxygenases 1, 2 and 3 and greater than about 10% linoleic acid as a percentage to total fatty acids that produces less than 20 µg of total 2,4 decadienal plus hexanal plus hexanol per gram of ground seeds following oxidation under mild aqueous conditions.

In accordance with another aspect of the invention, soybeans containing lipoxygenases are provided having less than about 4% linolenic fatty acid and greater than about 10% linoleic acid as percent of total fatty acid and producing less than 20 µg of total 2,4-decadienal plus hexanal plus hexanol per gram of ground seeds following oxidation under mild aqueous conditions. The same soybeans may also produce less than 8 µg of 1-octen-3-ol content per gram of ground seeds following oxidation under mild aqueous conditions.

In accordance with still yet another aspect of the invention, the invention also provides, soybeans having less than about 2000 µg free arginine and less than about 400 µg free asparagine per gram dry seed weight and producing less than about 20 µg/gm of 2,4-decadienal, hexanal and hexanol per gram ground soybeans following oxidation under mild aqueous conditions. The same seeds may also produces less than 8 µg of 1-octen-3-ol content per gram ground soy seeds following oxidation under mild aqueous conditions.

In accordance with still yet another aspect of the invention, soybeans are provided having yellow color measured as "b* value" of less than 30 and producing less than 20 µg/gm of 2,4-decadienal, hexanal and hexanol per gram ground soybeans following oxidation under mild aqueous conditions. The same seed may also produce less than 8 µg of 1-octen-3-ol content per gram of ground seeds following oxidation under mild aqueous conditions.

In accordance with still yet another aspect of the present invention, soybeans are provided having greater than 30% of the protein as β-conglycinin and or less than 25% of the protein as glycinins that produce less than 20 µg/gm of 2,4-decadienal, hexanal and hexanol per gram ground soybeans following oxidation under mild aqueous conditions. The same seed may also produce less than 8 µg 1-octen-3-ol per gram ground seeds following oxidation under mild aqueous conditions.

In accordance with the present invention, soybeans are provided comprising less than 5,000 µg free arginine, less than 900 µg free asparagine and greater than 30% of the protein as β-conglycinin and less than 25% of the protein as glycinins that produce less than 20 µg/gm of 2,4-decadienal, hexanal and hexanol per gram ground soybeans following oxidation under mild aqueous conditions. The same seed may also produce less than 8 µg 1-octen-3-ol per gram of ground seeds following oxidation under mild aqueous conditions.

In accordance with still yet another aspect of the invention, soybeans are provided resulting from a cross of a first soybean seed having greater than 30% of the total protein as β-conglycinin and less than 25% of the protein as glycinins and a second soybean seed producing less than 20 µg/gm of 2,4-decadienal, hexanal and hexanol per gram ground soybeans following oxidation under mild aqueous conditions.

In accordance with still yet another aspect of the invention, soybeans are provided resulting from a cross of a first soybean seed having less than 4% linolenic fatty acid and greater than 10% linoleic acid as percent of total fatty acids and a second soybean seed containing lipoxygenases 1, 2 and 3 and greater than 10% linoleic acid as a percentage of total fatty acids producing less than 20 µg/gm of 2,4-decadienal, hexanal and hexanol per gram ground soybeans following oxidation under mild aqueous conditions.

In accordance with still yet another aspect of the invention, a method of analyzing the odor-producing property of soybean seed varieties is provided comprising incubating a mixture of about 1 part of soybean seed flour and about 4 parts of water for a period in the range of about 1 to about 40 minutes and quantifying amounts of at least one compound selected from the group consisting of 2,4 decadienal, hexanol, hexanal, and 1-octen-3-ol and combinations of two, three or four thereof using deuterated standards for hexanal, hexanol and decadienal.

In accordance with still yet another aspect of the invention, a method of soybean breeding is provided comprising incubating a mixture of about 1 part of soybean flour or dehulled-soybean flour and about 4 parts of water for a period in the range of about 1 to about 40 minutes at room temperature and quantifying amounts of 2,4 decadienal, hexanol, hexanal, and 1-octen-3-ol using deuterated standards for hexanal, hexanol and decadienal and selecting seed from breeding populations based on the results.

In accordance with another aspect of the invention, soybeans are provided comprising a transgene, for example, a herbicide resistance gene imparting herbicide resistance or an insecticidal gene imparting insect resistance.

In accordance with another aspect of the invention, processed foods for human consumption are provided comprising soybeans having greater than 30% of the protein as β-conglycinin and less than 25% of the protein as glycinins that produce less than 20 µg/gm of 2,4-decadienal, hexanal and hexanol per gram ground soybeans following oxidation under mild aqueous conditions.

DESCRIPTION OF ILLUSTRATIVE EMBODIMENTS

The invention provides soy compositions, soybeans, and soybean seed derivatives with improved organoleptic properties, and methods for producing the same. The soy compositions of the invention provide improved taste, color, odor and mouth feel properties. The invention also provides methods for producing such compositions and methods of determining the ability of a soybean variety to produce key odors identified as 2,4 decadienal, hexanal, hexanol and 1-octen-3-ol and the use of the results to select seeds from breeding populations.

Oxidation conditions may be produced in accordance with the invention when approximately 0.5 soy flour is mixed with 2 mL of water or 1 part of soybean flour is mixed with 4 parts of water to disperse the solid particles in water and allow oxidization reactions to occur for approximately 1-40 minutes at room temperature wherein room temperature could vary from 15° to 40° C. The concentrated suspension allows enzymes, substrates, free radicals, free radical scavenging compounds, enzyme inhibitors, and other factors impact the amounts of odors produced.

The invention provides lipoxygenase containing soybeans and compositions derived therefrom having less than 4% linolenic fatty acid and/or greater than 10% linoleic acid as percent of total fatty acid and producing less than 20 µg 2,4-decadienal ($CH_3(CH_2)_4CHCHCHCHCHO$, CAS No. 25152-84-5) plus hexanal ($CH_3(CH_2)_4CHO$, CAS No. 66-25-1) plus hexanol ($CH_3(CH_2)_5OH$, CAS No. 111-27-3) per gram of ground seeds following oxidation under mild aqueous conditions. The same soybeans may also produce less than 8 µg of 1-octen-3-ol ($CH_3(CH_2)_4CHOHCHCH_2$, CAS No. 3391-86-4) per gram of ground seeds or dehulled soy flour following oxidation under mild aqueous conditions. The compounds 2,4 decadienal, hexanol, hexanal, and 1-octen-3-ol and their combinations were used to quantify odor-producing properties of soybeans. Odors are not restricted to these listed compounds. Other detectable aldehydes, ketones and alcohols can be used as measures of odor producing properties using the method of the invention. Examples of these compounds include but are not restricted to Propanal, Pentenal, Pentanal, Hexenal, Pentenol, Heptanal, Heptenal, Benzaldehyde, Hexadienal, Heptadienal, Heptanol, Octenol, Octenal, Nonanal, Octadienone, 2 pentyl Furan, Pentanal, 2,3-dimethyl, Nonenal, Maltol, Decenal, and 2-Undecenal. According to the invention the term "lipoxygenase" refers to an enzyme that catalyzes oxidation of unsaturated fatty acids with oxygen to yield peroxides. The term "lipoxygenase" (EC. 1.13.11.12) is also referred as lipoxidase and dioxygenase in the art. Odors of soymilk and soy protein ingredients from soybeans lacking one, two or three of the lipoxygenases 1, 2 and 3 were assessed by other researchers. High oleic soybeans exist with less than 4% linoleic acid. Some of the soybeans having those traits may produce less than 20 µg of total 2,4 decadienal plus hexanal plus hexanol per gram of ground soybeans using the assay of this invention and some will not fall in that range. It was discovered in this invention that is possible to create soybeans that contain lipoxygenases 1, 2 and 3 that produce very low levels of odors and that lipoxygenase-null soybeans can produce high levels of off-flavors. In addition to high β-conglycinin compositions that were not previously screened for odor-producing properties, the invention provides in particular new soybean compositions having lipoxygenases 1, 2 and 3 and greater than 10% linoleic acid. Linoleic fatty acid (18:2 n-6) and linolenic fatty acid (18:3 n-6) are polyunsaturated fatty acids with two or three cis double bonds according to the invention. The methods of the invention for selecting low odor-producing lines from the progeny of lipoxygenase-null soybeans or high oleic soybeans are within the scope of the invention.

The odor 1-octen-3-ol is a cleavage product of fatty acids having hydroperoxides on the 10 carbon position of linoleic acid. It was discovered in this invention that the removal of the hull substantially reduces the 1-octen-3-ol forming property of soybean compositions. Fungal lipoxygenases and hydroperoxide lyases form 10-hydroperoxides and 1-octen-3-ol, respectively (Wurzenberger and Grosch, 1984; Husson et al., 1998). It was reasoned in this invention that soybeans that produce lower amounts of 1-octen-3-ol, resist contamination of the soybean hull by fungus such as Phomopsis (Minor et al., 1995) and or contain components that inhibit the fungal lipoxygenases.

The organoleptic properties of soybean products depend on the contents of glycinins and β-conglycinins. The glycinins are more prone to retaining odors and to forming insoluble particles that adversely affect the sensory quality of soybean products. The present invention provides soybeans having greater than 30% of the protein as β-conglycinin and less than 25% of the proteins as glycinins and will produce less than 20 μg of total 2,4-decadienal plus hexanal plus hexanol per gram of ground seeds following oxidation under mild aqueous conditions. The same seeds may also produce less 8 μg of 1-octen-3-ol per gram of ground seeds under similar conditions. According to the present invention β-conglycinin refers to a protein trimer with a molecular weight mass of 150-200 kDa. Three major subunits of β-conglycinin are the α' (72 kDa), α(68 kDa), and β(52 kDa). The alpha-prime and alpha subunits contain two covalently bound carbohydrate moieties and the beta-subunit contains one. A review of the structure and properties of β-conglycinin and the other major storage protein, glycinin is given by Utsumi et al., (1997). One can use public germplasm such as "Moshidou Gong 503" to change the ratio of α to α' subunits of β-conglycinin using traditional breeding methods. The term β-conglycinin in this application includes these subunit variations. The seeds of the present invention having greater than 30% of the protein as β-conglycinin and or less than 25% of the protein as glycinins are provided that comprise less than 5,000 μg/g free arginine and less than 900 μg/g free asparagine. The term "free" refers to amino acids that are not bound with other molecules present in the soybeans or soybean seed flour and can be extracted and solubilized by 5% aqueous solution of trichloroacetic acid (TCA) at 4° C. overnight. The value of selecting soybeans comprising low levels of free amino acids for producing high quality soybean meats, soymilk, soy flour, soy protein concentrates and soy protein isolates had not previously been demonstrated.

The color of soy ingredients and foods made according to the invention may be improved by reducing the levels aldehydes formed (e.g. hexanal and 2,4 decadienal) because aldehydes react with amines to form brown pigments. Reduced levels of lipid oxidation products can also limit the oxidative bleaching of yellow pigments causing a final product color to be less white. The potential low bleaching problem is solved in this invention by selecting soybeans containing low levels of yellow pigment. The invention provides soybean compositions having yellow color measured as "b* value" of less than 30 and producing less than 20 μg of total 2,4-decadienal plus hexanal plus hexanol per gram of ground seeds following oxidation under mild aqueous conditions. The "b*" value as used herein to describe the color of soybean seed represents the CIE-L*a*b* Color Scale (CIE, Colorimetry, Publication 15.2, Second Edition, Vienna (1986) using Colorflex procedure) and relates to blueness (negative numbers) to yellowness (positive numbers) of soybeans or soybean flour, similarly "L*" value refers to lightness of soybeans or soybean flour on CIE-L*a*b* Color Scale. Soybeans or soybean flour in one embodiment of the invention will have L* value greater than 80.

The desired wild-type soybean, commercial cultivar, or hybrid thereof may be crossed by conventional plant breeding methods with a soybean plant having seeds with the low odor producing phenotype of the invention to create seeds comprising the low odor trait plus other desired traits (e.g., yield, high β-conglycinin composition, herbicide resistance). Hybrid progeny exhibiting the low odor trait and others desired phenotypes are selected. Breeding methods used in accordance with the present invention include, for example, methods described in Knowles and Briggs (1967) or any like methods known in the art. Specific methods for the selection and development new soybean varieties, for example, are disclosed in U.S. Pat. No. 6,653,534.

The invention also provides processed food for human consumption made from soybean compositions of the invention. Example of processed foods for human consumption may be made, for example, from a dehulled soy flour composition of the invention. Examples of these derivatives include but are not limited to, bars, beverages, meat and meat alternatives, soy yogurt, cheese alternatives, nutritional supplements.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Materials and Methods

This example describes an analytical method of the present invention. The purpose of this analytical method is to determine the odor-producing properties of different soybean lines.

The method determines selected odors by first initiating odor formation. Grinding the seed into fine flour and activating enzymes using water caused the odors to form. Studies on the rate of formation indicated that at room temperature the formation of the odors were mostly complete after about 20 minutes (Table 1). This time was important to successful quantitation of the odor compounds and assessment of the odor producing properties of different soybean lines. After 20 minutes deuterated surrogates of hex anal, hexanol and 2,4 decadienal were added to provide internal standards. The reaction was stopped by the addition of sodium sulfate which was immediately followed with the addition of 10% methanol:ether to extract the aldehydes, alcohols and ketones. The method was not restricted to the compounds listed. All other detectable aldehydes, ketones and alcohols can be quantified but not with the precision as the three using deuterated surrogates.

TABLE 1

Effect of time after mixing soybean flour with water (0.5 g flour 2 mL water, i.e. 1:4 ratio) on formation of flavor components. The pH of the suspensions for four different soybean lines (A-4, A-5, A-10 & A-14) was about 6.3.

| Time (minutes) | Hexanal (µg/g) | 2 x st dev. | 1-Octen-3-ol (µg/g) | 2 x st dev. | 2,4 Decadienal (ug/g) | 2 x st dev. | pH (A-4) | pH (A-5) | pH (A-10) | pH (A-14) |
|---|---|---|---|---|---|---|---|---|---|---|
| 0 | 1.3 | 2.6 | 0.8 | 0.4 | 0.4 | 0.4 | 6.4 | 6.4 | 6.3 | 6.3 |
| 5 | 11.8 | 0.2 | 2.9 | 0.4 | 6.9 | 0.7 | | | | |
| 10 | 11.4 | 1.4 | 3.7 | 0.7 | 6.5 | 0.6 | 6.3 | 6.3 | 6.3 | 6.3 |
| 20 | 14.0 | 0.8 | 5.8 | 0.6 | 7.8 | 0.9 | 6.3 | 6.3 | 6.3 | 6.3 |
| 40 | 15.7 | 1.9 | 7.8 | 0.5 | 8.6 | 2.3 | 6.3 | 6.3 | 6.3 | 6.3 |
| 240 | 17.0 | 4.2 | 8.9 | 1.8 | 9.9 | 1.7 | | | | |

The analytical time to determine these components in 175 samples takes 24 hours. This includes extraction and determination using gas chromatography/ mass spectrometry. The size of the sample for analysis was typically 0.5 grams (g) but can range from 0.2 g to 0.7 g. The range of an odor concentration on a wet weight bases was from 0.2 µg/g to 120 µg/g.

Soybean Meat Sample Preparation: Whole seed or soybean meats were collected as samples. Approximately 6 to 12 randomly selected seed or the equivalent weight as soybean meat pieces from a sample were ground in a ball mill at approximately 1200 revolution per minute (rpm) for 1 minute to produce a fine flour. Ball mill for grinding seeds is described in a U.S. Patent Pub. 2003/0146313 A1. Number of seeds or soybean meats was determined to obtain approximately 0.5 to 1.0 g of soybean flour at the end of grinding. Freshly ground soybean flour was used for further analysis.

Extraction of soybean flour: Freshly ground soybean flour was used for extraction of the key odors. Approximately 0.5 g (0.48 to 0.52 g) of soy flour was taken in a 20 milliliter (ml) vial (VWR TraceClean™ clear borosilicate Teflon lined closure vials) with a cap. De-ionized water (2 ml) was added to the flour in the vial before replacing the cap. Contents of the vial were mixed for approximately 30 seconds (sec) in a vortex mixer to ensure that all soybean flour was properly hydrated in the vial. Hydrated soybean flour was allowed to incubate under mild aqueous conditions, which are defined herein as incubation in water at room temperature (22° C.) for 20 minutes (min). After 20 min, 11±0.3 grams of anhydrous sodium sulfate was added in the vial followed by addition of 10 ml of 10% methanol:ether solution in the vial. 30 microliters of a standard surrogate (mixture of deuterated standards for Hexanal, hexanol and decadienal) spiking solution was further added in the vial before recapping and shaking it for 30-40 min on a reciprocating shaker at ~200 rpm. After 30-40 minutes 1 ml of methanol:ether extract was placed into a Autosampler vial (Autosampler vial for 7683 HP Autosampler. Vendor is VWR) for further analysis.

Analysis of Soybean Flour Extracts: Soybean flour extracts in methanol:ether extraction medium were further analyzed in a Gas Chromatograph Agilent 6890 (395 Agilent Technologies, Palo Alto Calif. 94306) equipped with Agilent 7683 series autosampler and Leco time of Flight mass spectrometer with LECO Chrom TOF software (LECO Corporation, St. Joseph, Mich. 49085). Gas chromatograph was also equipped with 10-meter DB-WAX or DB1701 gas chromatography column with film thickness of 0.4 or higher and ID 0.18 mm (Agilent Technologies). Methanol (methanol is EM Science methanol purge and trap grade) was procured from VWR (VWR International West Chester, Pa. 19380); Ethyl ether (ethyl ether anhydrous) was obtained from Mallinckrodt (Mallinckrodt, Hazelwood, Mo. 63042). 2,4 decadienal, 85% trans (15% cis), Hexanal 98%, Hexanol, 99%, 1 octen-3-ol 98%, 2 undecanone 99%, 2 nonenal 97%, and 2,4 nonadienal 99% were procured from Sigma-Aldrich Company (Saint Louis Mo. 63103). Deuterated $D_{12}$ Hexanal, $D_{13}$ Hexanol, and $D_2$ 2,4 decadienal were made in house as described by Lin et al. (1999). For analysis of samples 1 micro-liter (µl) of sample was injected through the injection port of the gas chromatography apparatus (gc). Parameter used for analyzing samples in chromatograph were as follows: Chromatograph Parameters Column: DB-Wax or DB 1701 capillary 10 m×0.18 mm, 0.4 mm Film Injection Volume: 1 ul Injection liner: Split/splitless liner.

Temperature Program: Initial 55° C. for 1 min 40° C. to 175° C. @ 40° C./min, hold 0 min 175° C. to 240° C. @ 35° C./min, hold 0 min Inlet temperature: 220° C. Injection mode: Pulsed splitless with 8 psi initial for 1.5 minutes Split ratio: 20:1 Carrier gas: Helium @ 1.8 mL/min constant flow.

LECO Time Of Flight Parameters Temperature interface: 250° C. Source Temperature: 200° C. Mass Spectrometer source temperature: 150° C. Scan parameters: 50 to 250 m/z at approx 50 scans per second.

Quality control of Analysis: For each batch of samples a method blank and a spike was run at the same time. The spike was made by splitting one of the samples to be analyzed into two portions. The sample should be as homogenous as possible. The second portion was spiked with a known amount of hexanal, 1 octen-3-ol and decadienal. This addition was made at the time of the addition of the deuterated compounds in extraction procedure as described above. The concentration of the spiked and unspiked compounds was determined as the % recovery by the following formula:

$$\% \text{ recovery} = 100 * \frac{(C_s)(wt_s) - (C_0)(wt_s)}{x_s}$$

Where:
  $C_s$=concentration of spiked sample in µg/(gm wet wt).
  $C_0$=concentration of the unspiked sample in µg/(gm wet wt).
  $Wt_s$=mass of sample spiked in gm.
  $X_s$=micrograms spiked into sample.

The method blank followed the extraction procedure without the addition of the soy flour.

Accuracy and Precision of Analysis: The accuracy and precision was determined by running a homogenous soy flour sample and spiking the sample with a known level of the three compounds hexanal, 1 octen-3-ol and 2,4 decadienal. Unspiked samples were also analyzed to determine the amounts of spiked compound recovery. Different spike levels can be used as a standard addition method to determine basis due to systematic errors. The average value along with the standard deviation was determined. The average value was compared to the known level of material added to give an estimate of the accuracy of the method. The standard deviation gives the precision of the measurement. Note it is important to understand that these approaches only measures the analytical variability since grinding over 40 seeds to make the homogenous soy flour averages out the seed variability. A larger variation may occur for the actual determination because of seed to seed variation. For hexanal the % recovery was 83.8%. For 1 octen-3-ol the % recovery was 93.6%. For 2,4 decadienal the % recovery was 99.3%. The hexanal was the least accurate based on the spike approach. This is believed to be because of the volatility of the hexanal and the fact that the method has low recoveries for hexanal. The octen-3-ol and 2,4 decadienal have higher degrees of accuracy using the spike approach. The precision as indicated by the % relative standard deviation of the recoveries was 5% for the hexanal and the octen-3-ol. For the 2,4 decadienal the precision as measured by the % relative standard deviation of the recovery values was 1.1%. Sample size was not found to have an effect from 0.2 to 0.9 grams for this homogenous sample but it may be a problem between samples. This was not tested. Thus sample size should be about 0.5 grams until sample size is known not to be a problem or the method is adjusted.

The detection range for all compounds is from 0.5 micrograms to 25 micrograms. Adding more standards to the standard curve can extend the range.

EXAMPLE 2

Identification and Selection of Low Odor Producing Soybeans

Potent odors were quantified in soymilk made from a control soybean (Vinton 81), a soybean lacking lipoxygenase-2 (QT-1) and a soybean lacking lipoxygenases 1,2 and 3 (IA2025). Soymilk was made from each soybean variety by soaking desired clean seeds in water in 1:5 ratio (1 gm weight:5 ml water at 25° centigrade (C) for about eight hours. After discarding soaking water, soybeans weighing twice the original weight were drained and blended with fresh distilled water (2× dry weight of soybeans) for five minutes. Additional distilled water (7× dry weight of soybeans) was blended into the slurry for about 2 minutes (min.) at 20° C. The slurry was simmered at 95° to 98° C. for 20 min. in a water bath and filtered through coarse woven cheesecloth and squeezed by hand to express as much soymilk as possible. The soymilk was pasteurized by simmering in a water bath at 85° to 90° C. for 10 minutes to reduce microbial contamination and stored at 4° C. before the extraction of odors for further analysis.

Odors were extracted from the soymilk samples. Soymilk was extracted with a 0.67 portion of Freon™ 113 for at least 30 minutes. After removal of the Freon™ 113 extract, the aqueous phase was further extracted with 0.67 portion of ethyl acetate. After the collection of ethyl acetate extract, the aqueous phase was discarded. Both Freon™ and ethyl acetate were filtered thru magnesium sulfate to remove as much water as possible and concentrated to 1 ml using Buchi 0.1 rotary evaporator. Freon extracts were evaporated under 48 kilopascal (kPa) and ethyl acetate under 86 kPa.

Potent odors produced in soymilks were quantified using GC-Olfactometry (Acree T. E, Analytical Chem. 69:170A-175A, 1997). GC-Olfactometery is gas chromatography with a sniffing port where potency of a chemical compound as an odorant is measured as a measurement of human response to odorants in air stream or puffs. Hewlett Packard 6890 gas chromatograph equipped with a 12 m×0.32 mm cross-linked methyl silicone fused silica capillary column (film thickness=0.33 μm) was used for CharmAnalysis™ (Acree, T. E.; Barnard, J; Cunningham D. G.; Food Chem. 14, 273-286, 1984). The effluent consisted of helium (2 ml/min) as the carrier gas and nitrogen as the make up gas (ca. 30 ml/min). The effluent was mixed with sniffing air (20 L/min) which was 99% laboratory air humidified to between 50% and 75% and passed through the sniffer via a 10 mm diameter silylated pyrax tube. The GCMS oven was programmed to start increasing its temperature three mins from the initial temperature of 35° C. to 225° C. at 6° C./min. Further details of the method for CharmAnalyis™ in soybean milk can be found in Ph.D. Dissertation presented to the faculty of Graduate School of Cornell University by Yu-Wen Feng.

Both soybeans lacking lipoxygenase-2 (IA2025, QT-1) produced lower levels of hexanal than the control (Table 2). The soybean lacking all three lipoxygenases (IA2025) produced the highest levels of 2,4 decadienal and 1-octen-3-one, while the soybean lacking lipoxygenase 2 (variety QT-1) had the lowest levels of all five potent odors (Table 2). It was apparent from the results that unknown compositional factors other than lipoxygenase-2 were involved in controlling lipid oxidation in soybeans. The soybean variety QT-1, was identified as a useful variety for creating commercial low odor soybean varieties comprising or not comprising lipoxygenase-2. The method of example 1 was developed to identify progeny of QT-1 and other soybean lines that produce low amounts of 2,4 decadienal, hexanal, hexanol and 1-octen-3-ol.

TABLE 2

Charm value of odors present in soymilk prepared from three varieties of soybeans. The proprietary Monsanto line produced lower levels of off-flavors than a triple lipoxygenase-null (IA2025) and tofu soybean(Vinton 81).

| Soybean Lines | 1-octen-3-one | 2,4 decadienal | E,Z-2,6 nondienal | E-2 nonenal | Hexanal |
|---|---|---|---|---|---|
| Low odor line QT-1 | 3 | 25 | 11 | 67 | 69 |
| IA2025 | 182 | 208 | 168 | 165 | 73 |
| Vinton 81 | 65 | 71 | 186 | 165 | 224 |

Table 3 describes soybean crosses that were used to develop the progeny for describing the invention. Standard methods of plant breeding were used to generate these lines.

TABLE 3

Soybean crosses used to develop progeny used to describe the soybeans and methods of the invention.

| Crosses | Cross type |
|---|---|
| MonQT-1/A346E> | A |
| A22 47/6P24S | B |
| A2533/IA2027 | C |
| IA2 032/A3469 | D |
| CP3469/1A2025 | E |

EXAMPLE 3

Demonstration of Year-to-Year and Location-to-Location Consistency of Low Odor-Producing, Low Color and Low Free Amino Acid Characteristics in Soybean Lines Selected According to the Invention For color evaluation whole seeds were collected as samples. Desired number of selected seed from a sample was ground in a Mega-Grinder at an rpm of 1200 for 1 minute to produce a finely ground soybean flour. Mega-Grinder for grinding seeds is described in a U.S. Patent Pub. 2003/0146313 A1. Freshly ground soybean flour was used for further analysis.

ColorFlex Spectrocolorimeter Model 45/0 color measuring system made by Hunter labs (Hunter Associates Laboratory Inc, Reston Va., USA) was used for measuring color of soybean flour by standard operation procedure suggested by the manufacturer. The colors were measured on CIE-L*a*b* color scale (CIE, Colorimetry, Publication 15.2, Second Edition, Vienna, 1986) using ColorFlex procedure. International Commission on Illumination—abbreviated as CIE from its French title Commission Internationale de l'Eclairage—is an organization devoted to international cooperation and exchange of information among its member countries on all matters relating to the science and art of lighting. The L* value relates to the lightness of the soybean flour while the b* value relates to the blue (negative numbers) to yellowness (positive numbers) of the soybean flour. Color values of Soybean Flour made from different lines are shown on Tables 4 and 5.

Free amino acids: Unground samples were stored in a temperature/humidity controlled, secured (APHIS approved) room. Samples were ground using the CAT Mega-Grinder to create soy flour and stored at 4° C. in seed storage room. Soy flour was extracted with 5% TCA at 4° C. overnight, centrifuged and extracts were stored at −80° C. Extracts were filtered, diluted if necessary and analyzed for free amino acids by the OPA method. The OPA method uses o-phthaldialdehyde (OPA) to derivatize samples before injection onto a C18, reverse phase HPLC column. The derivatized, primary amino acids are efficiently separated by R-group and quantitatively detected by a sensitive fluorometer. The relative standard deviation for this method is ~3%.

Lipoxygenase activity: Samples were ground using a Mega-Grinder. Each freshly ground sample was weighed out in triplicate (5 mg±1) and placed into a specific well of a 2-ml 96-well extraction plate. Samples were extracted with 0.1M $K_2HPO_4$ (pH 7.0 or pH 9.) for 1 hour at room temperature. After centrifugation, supernatant obtained was used to measure the consumption of linoleic acid (substrate) using a spectrophotometer followed by determination of total protein per sample using Bio Rad Protein Dye. Lipoxygenase unit was calculated by using the absorbance changes at 230 nm during a 1-minute reaction and using the extinction coefficient ($\epsilon=23{,}000$ $M^{-1}cm^{-1}$). The concentration of substrate consumed during the reaction was calculated by substituting each value into the equation $A=\epsilon bC$. One unit of lipoxygenase was defined as the µmoles of substrate consumed per min and mg total extracted protein. By using reagent solutions prepared at pH 7.0 or pH 9.0, this assay allows one to measure the levels (Units of enzyme) of lipoxygenase-2/-3 or lipoxygenase-1, respectively. Lipoxygenase unit results are given as LOX Units pH 7.0 for Lipoxygenase-2 and 3 activities and as a LOX Units pH 9.0 for Lipoxygenase-1 activity.

Results: Soybean odor characteristics persisted when grown in multiple locations (Table 4) and multiple years (Tables 4 and 5). Soybeans lines that produced low levels of hexanal, hexanol and 2,4 decadienal and 1-octen-3-ol in the odor assay (described in Example 1) were consistently different from lines that produced high levels (Table 4). The soybean lines in Table 4 were sorted in order of the levels of hexanal+hexanol+2,4 decadienal that the lines produced. For example line A-1 at the top of the table produced 18.21+/−4.21 µg/g of the three odors in contrast with line A-18 at the bottom of the table that produced 65.74+/−21.97 µg/g of the three odors. The amounts of hexanal plus hexanol produced by the soybeans from the same cross (e.g., cross A) correlated with the amounts of 2,4 decadienal produced (Table 6, $R^2=0.85$) suggesting similar mechanisms and control by genetic and compositional variations. The levels of 1-octen-3-ol produced were independent of hexanal, hexanol and 2,4 decadienal (Table 6, $R^2=0.01$) suggesting a different mechanism of formation and control. Soybeans lines grown in 2-3 locations that produce low levels of 1-octen-3-ol were consistently different from lines than produced high levels of 1-octen-3-ol. For example, line A-18 produced 4.70+/−0.88 µg/g 1-octen-3-ol and line A-12 produced 14.67+/−2.37 µg/g 1-octen-3-ol. One can select lines that have a combination of genetic compositions that produce lower levels of 1-octen-3-ol and lower levels of 2,4 decadienal plus hexanal plus hexanol (e.g., line A-6).

Table 4 A & B: Color and odors produced by ground soybeans made from the progeny of crosses A, B, C, D and E as shown on Table 3. Values are the mean and standard deviation (Stdev) for each line grown in two or three locations in 2002 (Ames, Iowa; Oxford, Ind.; Gladbrook, Iowa). Progeny of cross B listed had low linolenic acid content of 2.9+/−0.4% of total fatty acids. All line shave yellow hilum. Ground soybeans had moisture content of 8%. Color values are L* (lightness), a* (green-red), and b* (blue-yellow). Abbreviations: Stdev=standard deviation.

TABLE 4 A.1

| Cross Type | Hexanal (µg/g) | Hexanol (µg/g) | Hexanal + Hexanol (µg/g) | 1-octen-3-ol (µg/g) | 2,4 decadienal (µg/g) | 2,4 Decadienal + Hexanal + Hexanol (µg/g) | Hexanal (µg/g) (Stdev) | Hexanol (µg/g) (Stdev) | Hexanal + Hexanol (µg/g) (Stdev) | 1-octen-3-ol (µg/g) (Stdev) | 2,4 Decadienal (µg/g) (Stdev) | 2,4 Decadienal + Hexanal + Hexanol (Stdev) |
|---|---|---|---|---|---|---|---|---|---|---|---|---|
| C 1, L-null | 9.78 | 1.06 | 10.84 | 10.79 | 6.23 | 17.07 | 3.36 | 0.93 | 4.29 | 0.34 | 0.64 | 4.93 |
| A-1 | 9.80 | 1.89 | 11.68 | 9.14 | 6.53 | 18.21 | 1.35 | 1.04 | 2.38 | 0.14 | 2.16 | 4.54 |
| B-1 | 9.88 | 0.34 | 10.22 | 10.03 | 8.52 | 18.75 | 3.93 | 0.48 | 4.42 | 3.39 | 0.06 | 4.48 |
| D-1, L-null | 12.59 | 0.92 | 13.51 | 13.51 | 5.24 | 18.75 | 1.89 | 0.83 | 2.16 | 3.11 | 2.46 | 4.58 |
| A-2 | 11.86 | 1.25 | 13.11 | 8.59 | 6.55 | 19.66 | 2.15 | 1.09 | 3.23 | 2.90 | 0.63 | 2.64 |
| B-2 | 11.99 | 1.78 | 13.76 | 8.19 | 6.91 | 20.67 | 4.07 | 1.11 | 5.18 | 2.98 | 1.37 | 6.55 |
| A-3 | 12.60 | 1.53 | 14.12 | 10.87 | 7.29 | 21.41 | 3.23 | 0.23 | 3.45 | 3.48 | 2.09 | 5.34 |
| A-4 | 14.76 | 2.30 | 17.05 | 9.29 | 6.32 | 23.38 | 2.71 | 0.23 | 2.94 | 2.16 | 1.29 | 4.01 |

TABLE 4 A.1-continued

| Cross Type | Hexanal (µg/g) | Hexanol (µg/g) | Hexanal + Hexanol (µg/g) | 1-octen-3-ol (µg/g) | 2,4 decadienal (µg/g) | 2,4 Decadienal + Hexanal + Hexanol (µg/g) | Hexanal (µg/g) (Stdev) | Hexanol (µg/g) (Stdev) | Hexanal + Hexanol (µg/g) (Stdev) | 1-octen-3-ol (µg/g) (Stdev) | 2,4 Decadienal (µg/g) (Stdev) | 2,4 Decadienal + Hexanal + Hexanol (Stdev) |
|---|---|---|---|---|---|---|---|---|---|---|---|---|
| A-5 | 14.95 | 1.38 | 16.33 | 9.08 | 7.65 | 23.98 | 4.94 | 0.17 | 5.08 | 1.02 | 4.55 | 9.55 |
| A-6 | 17.5S | 3.21 | 20.79 | 4.63 | 8.97 | 29.75 | 1.26 | 1.36 | 2.62 | 2.90 | 5.38 | 2.76 |
| A-7 | 19.3S | 3.35 | 22.73 | 7.71 | 8.39 | 31.12 | 3.03 | 1.76 | 3.49 | 1.54 | 2.69 | 3.73 |
| A-8 | 23.69 | 2.73 | 26.42 | 9.14 | 11.51 | 37.93 | 10.64 | 0.69 | 10.90 | 3.53 | 4.64 | 15.49 |
| A-9 | 25.45 | 3.41 | 28.86 | 10.12 | 10.53 | 39.39 | 6.71 | 0.52 | 6.25 | 0.93 | 1.70 | 7.60 |
| A-10 | 27.14 | 3.11 | 30.25 | 10.24 | 9.92 | 40.17 | 4.99 | 2.04 | 6.19 | 1.31 | 2.73 | 7.86 |

TABLE 4 A.2

| Cross Type | Hexanal (µg/g) | Hexanol (µg/g) | Hexanal + Hexanol (µg/g) | 1-octen-3-ol (µg/g) | 2,4 decadienal (µg/g) | 2,4 Decadienal + Hexanal + Hexanol (µg/g) | Hexanal (µg/g) (Stdev) | Hexanol (µg/g) (Stdev) | Hexanal + Hexanol (µg/g) (Stdev) | 1-octen-3-ol (µg/g) (Stdev) | 2,4 Decadienal (Mg'g) (Stdev) | Decadienal + Hexanal + Hexanol (µg/g) (Stdev) |
|---|---|---|---|---|---|---|---|---|---|---|---|---|
| A-11 | 31.27 | 4.05 | 35.32 | 8.71 | 11.62 | 46.94 | 11.65 | 1.21 | 11.65 | 2.18 | 5.95 | 17.16 |
| A-12 | 32.72 | 3.64 | 36.36 | 14.67 | 15.18 | 51.54 | 6.84 | 0.08 | 6.91 | 2.35 | 1.35 | 5.56 |
| A-13 | 35.16 | 4.30 | 39.46 | 10.03 | 12.33 | 51.78 | 8.20 | 0.99 | 9.20 | 3.74 | 2.74 | 11.94 |
| B-3 | 35.16 | 3.66 | 38.82 | 7.18 | 15.57 | 54.39 | 7.59 | 0.45 | 8.04 | 1.03 | 2.93 | 10.97 |
| E | 34.26 | 4.41 | 38.67 | 5.35 | 16.27 | 54.94 | 10.47 | 0.24 | 10.23 | 0.88 | 5.00 | 15.22 |
| A-14 | 35.24 | 2.23 | 37.47 | 7.06 | 18.94 | 56.41 | 10.58 | 1.72 | 8.85 | 0.05 | 10.16 | 19.02 |
| A-15 | 40.01 | 4.12 | 44.14 | 8.25 | 14.89 | 59.02 | 0.81 | 1.13 | 1.86 | 1.91 | 2.39 | 4.20 |
| A-16 | 37.88 | 5.66 | 43.53 | 8.17 | 16.80 | 60.33 | 13.20 | 2.33 | 14.11 | 3.43 | 4.61 | 16.31 |
| D-3 | 49.52 | 2.26 | 52.3S | 11.40 | 10.69 | 63.07 | 15.72 | 3.94 | 18.82 | 0.86 | 7.14 | 25.31 |
| B-4 | 41.26 | 4.04 | 45.30 | 6.90 | 18.02 | 63.32 | 12.25 | 0.33 | 12.58 | 1.27 | 7.67 | 20.25 |
| B-5 | 37.99 | 7.22 | 45.21 | 9.04 | 18.51 | 63.72 | 18.14 | 1.04 | 19.17 | 0.01 | 7.55 | 26.72 |
| A-17 | 42.44 | 4.72 | 47.16 | 9.32 | 16.99 | 64.15 | 5.64 | 1.02 | 5.38 | 2.59 | 6.57 | 11.78 |
| D-2 | 43.54 | 10.71 | 54.26 | 7.62 | 10.08 | 64.34 | 14.71 | 1.41 | 13.30 | 2.41 | 4.44 | 17.74 |
| B-6 | 40.64 | 4.97 | 45.60 | 9.96 | 18.82 | 64.42 | 5.56 | 2.45 | 7.07 | 1.06 | 3.56 | 10.62 |
| A-18 | 42.56 | 5.46 | 48.01 | 4.70 | 17.72 | 65.74 | 11.59 | 2.08 | 13.50 | 0.88 | 8.51 | 21.97 |

TABLE 4 B1

| Cross Type | Free Arg (µg/g) | Free Asn (µg/g) | Free Arg Asn (µg/g) | Free Are. (Stdev) | Free Asn (Stdev) | L* | a* | b* | L* (Stdev) | a* (Stdev) b* | (Stdev) | Lipoxygenase activity pH 7 | Lipoxygenase activity pH 7 Stdev |
|---|---|---|---|---|---|---|---|---|---|---|---|---|---|
| C-1, L-null | 845 | 185 | 1030 | 535 | 9 | 79.77 | 1.49 | 30.38 | 1.21 | 0.9 | 2.6 | 0.23 | 0.58 |
| A-1 | 1824 | 331 | 2155 | 1241 | 39 | 84.35 | 0.03 | 25.35 | 0.9 | 0.15 | 1.25 | 0.14 | 0.94 |
| B-1 | 968 | 95 | 1063 | 541 | 63 | 80.23 | 0.53 | 28.38 | 0.39 | 0.26 | 2.49 | | |
| D-1, L-null | 1105 | 91 | 1196 | 89 | 2 | 82.95 | 0.54 | 25.78 | 3.02 | 0.47 | 4.47 | | |
| A-2 | 1621 | 321 | 1941 | 278 | 155 | 85.42 | 0.18 | 22.16 | 0.94 | 0.03 | 1.39 | | |
| B-2 | 979 | 78 | 1058 | 865 | 32 | 81.7 | 0.22 | 28.7 | 1.5 | 0.23 | 2.54 | | |
| A-3 | 3157 | 420 | 3578 | 278 | 119 | 84.84 | 0.27 | 23.28 | 0.16 | 0.21 | 1.44 | | |
| A-4 | 1666 | 179 | 1845 | 687 | 104 | 85.73 | 0.01 | 22.21 | 0.68 | 0.04 | 1.26 | 1.69 | 0.31 |
| A-5 | I860 | 184 | 2044 | 216 | 3 | 84.95 | 0.05 | 24.12 | 1.07 | 0.22 | 1.65 | 1.02 | 0.16 |
| A-6 | 1144 | 183 | 1327 | 771 | 14 | 82.77 | 0.09 | 27.35 | 0.77 | 0.48 | 2.85 | | |
| A-7 | 2831 | 487 | 3318 | 496 | 137 | 85.06 | −0.18 | 23.4 | 2.21 | 0.17 | 4.01 | | |
| A-8 | 1657 | 221 | 1878 | 181 | 46 | 84.75 | 0.18 | 24.59 | 1.78 | 0.22 | 2.78 | | |
| A-9 | 2458 | 541 | 2998 | 264 | 51 | 83.31 | 0.36 | 25.51 | 3.72 | 0.67 | 4.73 | | |
| A-10 | 2843 | 461 | 3304 | 612 | 170 | 83.82 | 0.3 | 24.54 | 3.65 | 0.59 | 4.14 | | |

TABLE 4 B2

| Cross Type | Free Arg (µg/g) | Free Asn (µg/g) | Free Arg + Asn (µg/g) | Free Arg (Stdev) | Free Asn (Stdev) | L* | a+ | b* | L* (Stdev) | a* (Stdev) | b* (Stdev) | Lipoxygenase activity pH 7 | Lipoxygenase activity pH 7 Stdev |
|---|---|---|---|---|---|---|---|---|---|---|---|---|---|
| A-11 | 1921 | 334 | 2255 | 519 | 103 | 83.59 | 0.32 | 25.29 | 3.97 | 0.67 | 5.72 | | |
| A-12 | 956 | 139 | 1095 | 540 | 10 | 83.42 | 0.11 | 26.67 | 1.71 | 0.22 | 2.79 | | |
| A-13 | 654 | 76 | 729 | 460 | 11 | 83.52 | −0.03 | 25.77 | 2.74 | 0.23 | 5.08 | | |
| B-3 | 1892 | 263 | 2154 | 1186 | 26 | 80.89 | 0.05 | 27.91 | 1.63 | 0.35 | 2.95 | | |
| E | 911 | 85 | 996 | 678 | 4 | 83.47 | 0.64 | 27.86 | 0.69 | 0.38 | 2.07 | | |

TABLE 4 B2-continued

| Cross Type | Free Arg (μg/g) | Free Asn (μg/g) | Free Arg + Asn (μg/g) | Free Arg (Stdev) | Free Asn (Stdev) | L* | a+ | b* | L* (Stdev) | a* (Stdev) | b* (Stdev) | Lipoxygenase activity pH 7 | Lipoxygenase activity pH 7 Stdev |
|---|---|---|---|---|---|---|---|---|---|---|---|---|---|
| A-14 | 1554 | 311 | 1865 | 732 | 66 | 84.24 | −0.12 | 25.17 | 0.93 | 0.09 | 1.74 | | |
| A-15 | 1847 | 292 | 2138 | 1045 | 217 | 83.68 | 0.28 | 25.01 | 3.41 | 0.63 | 4.15 | | |
| A-16 | 1860 | 305 | 2165 | 513 | 148 | 84.3 | 0.1 | 25.1 | 2.64 | 0.39 | 3.16 | 1.71 | 0.94 |
| D-3 | 1280 | 188 | 1468 | 274 | 52 | 83.47 | 0.56 | 23.91 | 3.58 | 0.62 | 4.02 | | |
| B-4 | 992 | 127 | 1119 | 637 | 3 | 83.41 | 0.04 | 27.16 | 0.79 | 0.12 | 2.99 | | |
| B-5 | 976 | 106 | 1081 | 514 | 8 | 82.75 | 0.11 | 28.39 | 0.44 | 0.21 | 2.13 | | |
| A-17 | 1618 | 241 | 1859 | 760 | 107 | 85.61 | −0.04 | 21.93 | 1.18 | 0.11 | 2.68 | | |
| D-2 | 1215 | 82 | 1298 | 758 | 6 | 82.76 | 0.57 | 28.69 | 0.59 | 0.32 | 0.19 | | |
| B-6 | 1430 | 157 | 1587 | 337 | 81 | 84.97 | 0.24 | 24.3 | 1.03 | 0.17 | 2.1 | | |
| A-18 | 2250 | 452 | 2702 | 281 | 128 | 85.25 | 0.12 | 23.48 | 1.15 | 0.18 | 0.75 | | |

Table 5 A &, B: Characteristics of soybean flour made from commercial commodity soybeans (controls) and the progeny of crosses A, B, C, D and E, grown in 2001. Ground soybeans had moisture content of 7%. Order of the lines is the same as in Table 4. Progeny of cross B listed had low linolenic acid trait (2.9+/0.4% of total fatty acids). Two progeny lacked one or more lipoxygenases, the others contained all three lipoxygenases designated as L1, L2, and L3. Lipoxygenase activities have units of micromoles of substrate consumed per mg of substrate. Color values are L* (lightness), a* (green-red), and b* (blue-yellow). Abbreviations: Stdev=standard deviation.

TABLE 5 A

| Cross Type | 2A Decadienal + Hexanal + Hexanol (μg/g) | 2,4 decadienal (μg/g) | Hexanal + Hexanol (μg/g) | 1-octen-3-oll (μg/g) | L* | a* | b* | Lipoxygenase activity pH 7 | Lipoxygenase activity, pH 9 | Free Arginine (μg/g) | Free Asparagine (μg/g) | Free Arg + Asn (μg/g) |
|---|---|---|---|---|---|---|---|---|---|---|---|---|
| C-1, L-null | 17.05 | 4.96 | 12.09 | 16.50 | 80.37 | 1.17 | 30.84 | −0.092 | 0.297 | 314 | 39 | 353 |
| A-1 | 17.96 | 3.04 | 14.92 | 14.20 | 83.36 | 0.05 | 28.05 | 4.015 | 6.687 | 866 | 69 | 935 |
| B-1 | 24.80 | 5.16 | 19.64 | 9.90 | 81.71 | 0.84 | 28.71 | 3.462 | 7.072 | 1037 | 59 | 1096 |
| D-1, L-null | 12.37 | 3.60 | 8.77 | 4.40 | 83.15 | 0.14 | 26.58 | 1.548 | 1.479 | 1124 | 82 | 1206 |
| A-2 | 17.44 | 4.00 | 13.44 | 8.70 | 83.42 | 0.17 | 26.40 | 2.860 | 15.800 | 2068 | 138 | 2206 |
| B-2 | 27.10 | 5.38 | 21.72 | 9.90 | 81.52 | 0.21 | 28.59 | 3.591 | 4.592 | 558 | 47 | 605 |
| A-3 | 20.58 | 4.42 | 16.16 | 9.30 | 84.25 | −0.19 | 26.43 | 2.683 | 6.412 | 4662 | 240 | 4902 |
| A-4 | 16.90 | 1.60 | 15.3 | 5.30 | 83.98 | −0.18 | 26.09 | 4.400 | 4.752 | 3884 | 190 | 4074 |
| A-5 | 15.73 | 2.30 | 13.43 | 4.90 | 82.53 | 0.11 | 29.00 | 4.681 | 5.624 | 2818 | 163 | 2981 |
| A-6 | 19.62 | 3.85 | 15.77 | 8.60 | 83.09 | 0.17 | 28.98 | 2.664 | 5.949 | 687 | 58 | 745 |
| A-7 | 21.96 | 4.20 | 17.76 | 4.80 | 83.53 | −0.33 | 26.13 | 4.515 | 6.257 | 2722 | 269 | 2992 |
| A-8 | 16.81 | 4.30 | 12.51 | 6.70 | 82.64 | 0.26 | 27.86 | 3.884 | 4.278 | 2126 | 108 | 2233 |
| A-9 | 21.95 | 6.80 | 15.15 | 5.90 | 82.84 | 0.01 | 28.64 | 5.247 | 4.090 | 2594 | 275 | 2868 |
| A-10 | 39.30 | 10.40 | 28.9 | 4.50 | 83.99 | −0.33 | 27.35 | 5.520 | 4.901 | 4009 | 267 | 4276 |
| A-11 | 27.46 | 6.30 | 21.16 | 4.30 | 81.88 | 0.54 | 29.37 | 4.748 | 5.681 | 1641 | 139 | 1780 |
| A-12 | 42.10 | 7.46 | 34.64 | 17.30 | 83.60 | −0.25 | 28.60 | 4.010 | 4.049 | 739 | 79 | 817 |
| A-13 | 34.05 | 8.58 | 25.47 | 16.60 | 82.80 | −0.11 | 29.21 | 4.983 | 5.377 | 547 | 42 | 589 |
| B-3 | 31.06 | 7.43 | 23.63 | 6.30 | 82.99 | 0.18 | 28.84 | 4.304 | 4.132 | 1761 | 135 | 1896 |
| E | 33.98 | 8.33 | 25.65 | 9.80 | 83.83 | 0.29 | 29.71 | 4.444 | 4.608 | 1310 | 90 | 1400 |
| A-14 | 41.75 | 9.81 | 31.94 | 11.20 | 82.98 | −0.16 | 29.00 | 4.208 | 4.459 | 1025 | 86 | 1111 |

TABLE 5 B

| Cross Type | 2,4 Decadienal + Hexanal + Hexanol | 2,4 decadienal (μg/g) | Hexanal + Hexanol (μg/g) | 1-octen-3-ol (μg/g) | L* | a* | b* | Lipoxygenase activity pH 7 | Lipoxygenase activity, pH 9 | Free Arginine (μg/g) | Free Asparagine (μg/g) | Free Arg + Asn (ug/g) |
|---|---|---|---|---|---|---|---|---|---|---|---|---|
| A-15 | 24.86 | 5.70 | 19.16 | 3.00 | 83.98 | −0.16 | 26.22 | 4.236 | 4.925 | 2634 | 207 | 2841 |
| A-16 | 31.99 | 9.70 | 22.29 | 5.50 | 82.58 | 0.40 | 29.04 | 5.659 | 6.237 | 1493 | 132 | 1625 |
| D-3 | 40.16 | 5.80 | 34.36 | 5.20 | 84.08 | 0.20 | 27.30 | 7.354 | 6.773 | 1561 | 152 | 1713 |
| B-4 | 30.70 | 5.79 | 24.91 | 7.90 | 82.94 | 0.24 | 29.64 | 4.724 | 4.675 | 669 | 61 | 736 |
| B-5 | 38.59 | 10.05 | 28.54 | 13.80 | 82.76 | −0.02 | 29.28 | 3.485 | 4.822 | 3060 | 239 | 3300 |
| A-17 | 35.38 | 8.90 | 26.48 | 6.00 | 84.50 | 0.53 | 25.86 | 5.253 | 4.888 | 993 | 73 | 1066 |
| D-2 | 43.55 | 5.89 | 37.66 | 8.60 | 82.75 | −0.37 | 30.70 | 5.435 | 4.848 | 1724 | 114 | 1838 |
| B-6 | 44.02 | 10.70 | 33.32 | 10.60 | 84.43 | −0.31 | 26.47 | 5.334 | 5.708 | 4594 | 377 | 4971 |
| A-18 | 27.88 | 6.70 | 21.18 | 4.10 | 84.71 | 0.06 | 27.35 | 4.604 | 4.263 | 3378 | 185 | 3564 |

TABLE 5 B-continued

| Cross Type | 2,4 Decadienal + Hexanal + Hexanol | 2,4 decadienal (μg/g) | Hexanal + Hexanol (μg/g) | 1-octen-3-ol (μg/g) | L* | a* | b* | Lipoxygenase activity pH 7 | Lipoxygenase activity, pH 9 | Free Arginine (μg/g) | Free Asparagine (μg/g) | Free Arg + Asn (ug/g) |
|---|---|---|---|---|---|---|---|---|---|---|---|---|
| Control 1 | 25.80 | 6.6 | 19.2 | 6.9 | 82.20 | 0.28 | 29.57 | 6.486 | 4.367 | 1078 | 88 | 1166 |
| Control 2 | 28.10 | 6.7 | 21.4 | 12.3 | 79.88 | 0.64 | 29.16 | 3.901 | 6.000 | 619 | 156 | 774 |
| Control 3 | 39.10 | 7.4 | 31.7 | 6 | 80.82 | 0.79 | 32.16 | 7.025 | 5.737 | 674 | 61 | 735 |
| Control 4 | 23.70 | 7.4 | 16.3 | 5.4 | 81.53 | 0.39 | 30.89 | 3.220 | 3.575 | 1167 | 66 | 1233 |
| Control 5 | 27.50 | 7.4 | 20.1 | 4.6 | 81.06 | 1.18 | 31.16 | 4.847 | 6.234 | 961 | 203 | 1164 |
| Control 6 | 30.70 | 8.4 | 22.3 | 3.1 | 81.64 | 0.37 | 27.67 | 4.845 | 5.015 | 1002 | 81 | 1083 |
| Control 7 | 29.40 | 8.5 | 20.9 | 6.7 | 80.35 | 0.22 | 28.51 | 3.748 | 4.885 | 1177 | 168 | 1345 |
| Control 8 | 28.50 | 9 | 19.5 | 10.4 | 79.49 | 1.14 | 33.37 | 7.119 | 6.388 | 360 | 54 | 414 |
| Control 9 | 27.90 | 9.6 | 18.3 | 8.4 | 82.45 | 0.62 | 27.88 | 3.181 | 5.730 | 1209 | 93 | 1302 |
| Control 10 | 25.80 | 9.7 | 16.1 | 9.9 | 80.70 | 0.90 | 31.03 | 5.768 | 5.715 | 970 | 117 | 1087 |
| Control 11 | 26.60 | 10.1 | 16.5 | 8.3 | 80.41 | 0.07 | 29.02 | 5.715 | 4.670 | 1214 | 200 | 1415 |
| Control 12 | 34.00 | 11.6 | 22.4 | 6 | 82.71 | 0.22 | 30.63 | 4.142 | 4.585 | 1674 | 125 | 1798 |
| Control 13 | 28.30 | 13.6 | 14.7 | 14.8 | 80.79 | 1.27 | 32.83 | 3.181 | 5.730 | 1358 | 303 | 1661 |

TABLE 6

Linear relations as determined by R-squared values, between odors produced from soybean progeny harvests m2001 & 2002. Linear regressions were calculated from data in Tables 4 and 5. Abbreviations: H + H = hexanal + hexanol; D = 2,4 decadienal; O = 1-octen-3-ol; DHH = 2,4 decadienal + hex anal + hexanol.

| Cross Type A (2002) | H + H | D | DHH | O |
|---|---|---|---|---|
| H + H | 1.00 | 0.85 | 0.99 | 0.01 |
| D | | 1.00 | 0.91 | 0.02 |
| DHH | | | 1.00 | 0.01 |
| O | | | | 1.00 |
| All Crosses (01 & 02) | H + H (02) | D (02) | DHH (02) | O (02) |
| H + H (01) | 0.56 | | | |
| D (01) | | 0.59 | | |
| DHH (01) | | | 0.62 | |
| O (01) | | | | 0.07 |

It was possible to develop good yielding low odor-producing, low color varieties for the first time using the methods and soybeans of this invention. For example, lines A-1, A-4 and A-6 yielded 90, 90.5 and 104% of that of commercial checks.

There was little or no relationship between lipoxygenase activities at pH 7 and 9 and the formation of 2,4 decadienal+hexanal+hexanol from hydrated soybean flour (R-squared values <0.35, Table 7). Soybeans that produced significant lipoxygenase activities at pH 7 and 9 (line A-1) had similar odor properties as a line that lacked lipoxygenase activities (Line C-1) (Table 5). Commercially available soybean lacking lipoxygenases 1, 2 and 3 (IA2032 from 1999 harvest) was also tested for lipoxygenase activity and odor formation. No lipoxygenase activities were found at pH 7 and 9 for the triple lipoxygenase-null soybean flour, yet significant levels of hexanal (23.3 μg/g), hexanol (14.9 μg/g), and 2,4 decadienal (5.8 μg/g) were formed in the odor assay of the invention. Following experiments using lipoxygenase inhibitors, it was concluded that at least one other lipoxygenase was active in this soybean composition.

Protein ingredients that are light in color are valued by the food industry, especially for dairy type products. Soybeans were grown in 2-3 locations to determine if low color soybeans could be selected. It was discovered that low color soybeans could be selected as determined from the b* value of ground soybeans (high b* value indicates more yellow, less blue; Table 4). For example, soybean A-2 had a b* value of 22.16+/−1.39 and soybean A-6 had a b* value of 27.35+/−2.85 (Table 4). A correlation existed between the b* value of soybean lines grown in 2001 and 2002 (R-squared=0.7; Table 7).

TABLE 7

Linear relations as determined by R-squared values for odor, free amino acid, and color produced from soybean progeny harvested in 2001 and 2002. Linear regressions were calculated from data in Tables 4 and 5. Free ammo acid correlations with 2002 data were made without three outliers (A-4, B-5 and B-6).

| | DHH (01) | Free Arg (01) | Free Asn (01) | Free Arg + Free Asn (01) | a* (02) | b + (02) | L* (02) | L* (01) |
|---|---|---|---|---|---|---|---|---|
| lox activity pH 7(01) | 0.34 | | | 0.01 | | | | |
| lox activity pH 9 (01) | 0.00 | | | 0.10 | | | | |
| DHH (01) | | | | 0.01 | | | | |
| O (01) | | | | 0.15 | | | | |
| a* (01) | | | | | 0.29 | | | |
| b* (01) | 0.00 | | | 0.28 | | 0.65 | | 0.48 |
| L ± (01) | | | | | | | 0.50 | |
| b* (02) | | | | | | | | 0.79 |

TABLE 7-continued

Linear relations as determined by R-squared values for odor, free amino acid, and color produced from soybean progeny harvested in 2001 and 2002. Linear regressions were calculated from data in Tables 4 and 5. Free ammo acid correlations with 2002 data were made without three outliers (A-4, B-5 and B-6).

| | DHH (01) | Free Arg (01) | Free Asn (01) | Free Arg + Free Asn (01) | a* (02) | b + (02) | L* (02) | L* (01) |
|---|---|---|---|---|---|---|---|---|
| Free Arg (01) | | | 0.81 | | | | | |
| Free Arg (02) | | 0.77 | | | | | | |
| Free Arg (02) | | | 0.66 | | | | | |
| Free Arg + Asn (02) | | | | 0.75 | | | | |

Environmental factors in addition to genetics affect compositions that influence the odor-producing properties of soybeans. Environmental effects were evident by comparing the odor-producing properties of soybean lines grown in two seasons, 2001 and 2002. The range of 2,4 decadienal+hexanal+hexanol for lines created were 12-44 µg/g in 2001 and 17-65 µg/g in 2002 (Tables 4, 5). The 1-octen-3-ol producing properties of soybeans appeared to be most sensitive to environmental factors as evidenced by the lack of correlation between 1-octen-3-ol produced by the same lines grown in 2001 and 2002 (R-squared=0.07, Table 6). In contrast the levels of 2,4 decadienal+hexanal+hexanol produced by the soybean lines in 2001 and 2002 correlated ($R^2$=0.62, Table 6).

The amounts of free arginine (Arg) and asparagine (Asp) in soybean progeny were determined. Free arginine and asparagine amounts correlated ($R^2$=0.81, Table 7) and the total arginine plus asparagine ranged from 353 to 3300 µg/g (2001) (Table 5). The free arginine+asparagine in the soybeans did not relate to the selected odor or color properties of the soybean (R-squared <0.3, Table 7), so it is necessary to assay for free amino acids to select lines that have combinations of low 2,4 decadienal, low color and low free amino acids. The feasibility of selecting low free amino acid soybean lines was supported by the good correlation between free arginine+ asparagine in lines harvested in two different years (R-squared=0.8; Table 7).

EXAMPLE 4

Combination of Low Odor Producing Property with High β-Conglycinin Composition and Low Free Arginine and Asparagine Compositions and Low Color Property The source of the high β-conglycinin trait was a mutated soybean lacking glycinins and containing about 55% of the total protein as β-conglycinins (U.S. Pat. No. 6,171,640). A lipoxygenase assay was not useful for selecting low odor-producing lines as described above. Soybeans were created that had protein, fat and amino acid profiles that were within the normal ranges for commodity soybeans.

Quantitation of soybean protein subunits: About 8 seeds were ground using a Mega Grinder (U.S. Patent Pub. 2003/ 0146313 A1). For each sample, ~30 mg of the flour was extracted in 1.0 mL Laemmli SDS Buffer pH 6.8 with 0.1M DTT on a nutator or multiplate vortexer for 45 60 minutes. Tubes were centrifuged 3-5 min. A portion of the supernatant was transferred to microcentrifuge tubes and diluted with the above buffer to yield 1.2 1.5 µg/µL total protein. The samples were boiled for 3 min, cooled and centrifuged. Pre-cast 10-20% gradient Tris-HCl-Criterion gels were loaded with 15-20 µg protein of each sample. The gels were electrophoresed at 180-200V, in 1×Tris-Glycine-SDS Run Buffer, until the tracking dye reached the bottom of the gel, about 1.2 hours. The gels were fixed for 30-60 minutes in 40% methanol/10% acetic acid, and stained with Colloidal Coomassie Blue G-250; minimum overnight or up to 3 days. To remove the background, the gels were destained with deionized water. The gels were imaged using the GS 800 Calibrated Densitometer. Quantitation was performed using Bio-Rad Quantity One Software. The software is used to determine the relative quantity of each band in the sample lane. The % glycinin subunits and % beta conglycinin subunits were reported as the relative percent of the total protein in the lane.

Total amino acid analysis: The sample was assayed by three methods to obtain the full profile. Tryptophan required a base hydrolysis with sodium hydroxide. The sulfur containing amino acids required an oxidation with performic acid prior to hydrolysis with hydrochloric acid. Analysis of the samples for the remaining amino acids was accomplished through direct acid hydrolysis with hydrochloric acid. Once hydrolyzed, the individual amino acids were then quantitated using an automated amino acid analyzer (Official Methods of Analysis of AOAC INTERNATIONAL, 2000).

Ash: The sample was placed in an electric furnace at 550° C. and ignited to drive off all volatile organic matter. The nonvolatile matter remaining was quantitated gravimetrically and calculated to determine percent ash. Official Methods of Analysis of AOAC INTERNATIONAL, (2000).

Carbohydrates: The total carbohydrate level was calculated by difference using the fresh weight-derived data and the following equation: % carbohydrates=100%- (% protein+% fat+% moisture+% ash). United States Department of Agriculture (1973).

Fat by Soxhlet Extraction: The sample was weighed into a cellulose thimble containing sand or sodium sulfate and dried to remove excess moisture. Pentane was dripped through the sample to remove the fat. The extract was then evaporated, dried, and weighed. Official Methods of Analysis of AOAC INTERNATIONAL (2000).

Moisture: The sample was dried in a vacuum oven at approximately 100° C. to a constant weight. The moisture weight loss was determined and converted to percent moisture.

Protein: Nitrogenous compounds in the sample were reduced in the presence of boiling sulfuric acid and a mercury catalyst mixture to form ammonia. The acid digest was made alkaline. The ammonia was distilled and then titrated with a standard acid. The percent nitrogen was calculated and converted to protein using the factor 6.25. Official Methods of Analysis of AOAC INTERNATIONAL (2000). Bradstreet, (1965). Kalthoff and Sandell (1948).

Results: A population of high β-conglycinin soybeans lines selected from a cross with a soybean containing the low odor producing trait exhibited a wide variation of odor-producing properties as measured by formation of hexanal, hexanol, 2,4 decadienal and 1-octen-3-ol (Table 8). Commodity soybeans contained about 22% of total protein as β-conglycinins and about 38% glycinins, compared to the soybeans in Table 8 that had greater than 30% of the protein as β-conglycinins and less than 25% of the proteins as glycinins. Soybeans were created having greater than 30% of the total protein as β-conglycinins that produced less than 20 μg/g total of hexanal plus hexanol and 2,4 decadienal in the odor assay of example 1, and also comprise low levels of free asparagine and free arginine (Table 8). For example, 20 high β-conglycinin lines were created by the invention that produced less than 20 μg/g of the total of 2,4 decadienal plus hexanal plus hexanol and a total of free arginine plus asparagine between 360 and 2,840 μg/g of ground soybeans (Table 8). The free asparagine of these lines was between 35 and 1,000 μg/g and the free arginine of these lines was between 500 and 2400 μg/g of ground soybeans.

Table 8 A and B: Characteristics of high beta-conglycinin soybean progeny harvested in the United States. Soybeans having greater than 30% of the protein as beta-conglycinins and less than 2:5% of the protein as glycinins were created that also produce less than 20 fig/g 2,4 decadienal plus hexanal plus hexanol per gram of soybean flour in the odor assay of example 1. A lipoxygenase activity assay was not useful for identifying the low odor producing lines.

TABLE 8A

| Sample ID | beta-conglycinin (% of total protein) | hexanal (μg/g) | hexanol (μg/g) | octen-3-ol (μg/g) | decadienal (μg/g) | Hexanal + Hexanol (μg/g) | Hexanal + Hexanol + 2,4 decadienal (μg/g) | Lipox. activity, pH 7 | Lipox. activity, pH 9 | Asn (μg/g) | Arg (μg/g) | Arg + Asn (μg/g) |
|---|---|---|---|---|---|---|---|---|---|---|---|---|
| HiBCSoy52 | 38.4 | 5.4 | 4.3 | 1.5 | 3.2 | 9.7 | 12.9 | 7.734 | 5.731 | 2024 | 4421 | 6445 |
| HiBCSoy70 | 39.5 | 6.1 | 5.3 | 6.1 | 2.8 | 11.4 | 14.2 | 6.483 | 11.347 | 771 | 2020 | 2791 |
| HiBCSoy41 | 43.2 | 5.6 | 6.1 | 9.1 | 2.8 | 11.7 | 14.5 | 8.626 | 8.499 | 72 | 994 | 1066 |
| HiBCSoy65 | 39.2 | 6.2 | 5.4 | 5.4 | 3.2 | 11.6 | 14.8 | 8.393 | 13.535 | 1939 | 5064 | 7003 |
| HiBCSoy35 | 42.0 | 6.2 | 5.3 | 8.5 | 3.9 | 11.6 | 15.5 | 6.935 | 9.623 | 171 | 757 | 928 |
| HiBCSoy67 | 40.4 | 6.7 | 5.5 | 2.6 | 3.4 | 12.2 | 15.6 | 7.019 | 8.377 | 1376 | 3323 | 4699 |
| HiBCSoy34 | 40.6 | 5.2 | 7.8 | 7.4 | 3.0 | 13.0 | 16.0 | 7.279 | 10.633 | 311 | 1382 | 1693 |
| HiBCSoy64 | 39.3 | 7.0 | 6.2 | 3.3 | 2.7 | 13.3 | 16.0 | 6.622 | 8.044 | 1723 | 3241 | 4964 |
| HiBCSoy62 | 41.1 | 6.9 | 6.7 | 1.1 | 2.7 | 13.6 | 16.2 | 5.697 | 10.358 | 2882 | 3938 | 6820 |
| HiBCSoy68 | 40.5 | 7.8 | 5.8 | 2.3 | 2.9 | 13.6 | 16.5 | 8.006 | 6.584 | 303 | 1655 | 1958 |
| HiBCSoy61 | 30.3 | 9.6 | 4.7 | 4.1 | 2.3 | 14.4 | 16.6 | 6.709 | 6.110 | 372 | 1664 | 2036 |
| HiBCSoy69 | 39.9 | 7.7 | 5.0 | 3.5 | 4.0 | 12.7 | 16.7 | 7.836 | 7.668 | 1393 | 4151 | 5544 |
| HiBCSoy48 | 44.5 | 7.1 | 6.4 | 2.2 | 3.3 | 13.5 | 16.8 | 7.601 | 3.783 | 99 | 1496 | 1595 |
| HiBCSoy40 | 45.0 | 5.7 | 6.7 | 6.9 | 4.4 | 12.4 | 16.9 | 7.893 | 8.897 | 956 | 1878 | 2834 |
| HiBCSoy11 | 48.2 | 7.5 | 4.0 | 8.0 | 5.6 | 11.5 | 17.1 | 6.447 | 13.771 | 107 | 1680 | 1787 |
| HiBCSoy42 | 38.6 | 7.4 | 6.0 | 6.0 | 3.7 | 13.4 | 17.1 | 6.825 | 11.446 | 77 | 289 | 366 |
| HiBCSoy53 | 40.0 | 6.9 | 6.7 | 4.2 | 4.2 | 13.6 | 17.9 | 6.649 | 6.849 | 1154 | 2489 | 3643 |
| HiBCSoy5 | 46.5 | 8.0 | 6.2 | 5.2 | 3.9 | 14.3 | 18.2 | 5.882 | 5.793 | 305 | 3109 | 3414 |
| HiBCSoy36 | 40.6 | 8.0 | 5.0 | 10.4 | 5.2 | 13.1 | 18.3 | 9.259 | 9.062 | 38 | 536 | 574 |
| HiBCSoy3 | 46.8 | 6.7 | 6.3 | 5.0 | 5.6 | 13.0 | 18.6 | 7.790 | 12.639 | 89 | 817 | 906 |
| HiBCSoy4 | 44.9 | 7.4 | 6.7 | 8.6 | 4.6 | 14.1 | 18.6 | 6.929 | 8.660 | 723 | 3448 | 4171 |
| HiBCSoy46 | 42.4 | 6.7 | 8.5 | 9.4 | 3.5 | 15.1 | 18.7 | 6.978 | 3.850 | 67 | 1114 | 1181 |
| HiBCSoy26 | 44.7 | 7.8 | 7.6 | 14.4 | 3.4 | 15.3 | 18.8 | 6.148 | 6.667 | 225 | 863 | 1088 |
| HiBCSoy18 | 44.8 | 9.3 | 4.6 | 7.6 | 5.0 | 13.9 | 18.9 | 9.482 | 7.439 | 121 | 504 | 625 |
| HiBCSoy6 | 45.9 | 8.0 | 6.8 | 10.6 | 4.4 | 14.8 | 19.1 | 8.298 | 7.876 | 105 | 1149 | 1254 |
| HiBCSoy17 | 43.7 | 7.7 | 5.7 | 12.6 | 5.8 | 13.3 | 19.1 | 9.689 | 6.337 | 298 | 2363 | 2661 |
| HiBCSoy44 | 31.7 | 7.6 | 7.2 | 7.2 | 4.7 | 14.8 | 19.4 | 8.909 | 6.160 | 125 | 569 | 694 |
| HiBCSoy63 | 33.5 | 10.3 | 6.7 | 1.9 | 2.7 | 16.9 | 19.6 | 6.177 | 10.239 | 677 | 1473 | 2150 |
| HiBCSoy57 | 36.9 | 8.3 | 5.8 | 6.0 | 5.6 | 14.0 | 19.6 | 8.831 | 13.258 | 1329 | 3515 | 4844 |
| HiBCSoy16 | 44.3 | 8.5 | 6.1 | 10.8 | 5.3 | 14.6 | 19.9 | 8.326 | 6.447 | 95 | 863 | 958 |
| HiBCSoy24 | 43.7 | 6.5 | 9.3 | 6.2 | 4.2 | 15.8 | 20.0 | 7.293 | 9.330 | 1083 | 1909 | 2992 |
| HiBCSoy58 | 36.4 | 7.7 | 7.3 | 3.2 | 5.0 | 15.1 | 20.1 | 8.078 | 14.134 | 1519 | 4252 | 5771 |
| HiBCSoy39 | 41.7 | 7.2 | 6.5 | 4.5 | 6.3 | 13.7 | 20.1 | 9.084 | 5.718 | 95 | 400 | 495 |
| HiBCSoy66 | 39.2 | 8.8 | 7.4 | 2.6 | 4.2 | 16.2 | 20.4 | 6.122 | 9.155 | 2573 | 4163 | 6736 |
| HiBCSoy38 | 37.6 | 7.9 | 5.7 | 5.3 | 7.0 | 13.6 | 20.6 | 9.356 | 9.776 | 71 | 592 | 663 |
| HiBCSoy59 | 37.2 | 9.6 | 5.2 | 5.0 | 5.8 | 14.8 | 20.6 | 10.126 | 8.492 | 271 | 1837 | 2108 |
| HiBCSoy37 | 36.8 | 9.1 | 6.7 | 4.2 | 4.9 | 15.8 | 20.7 | 8.990 | 6.942 | 276 | 572 | 848 |
| HiBCSoy2 | 45.9 | 11.5 | 5.2 | 3.1 | 5.0 | 16.7 | 21.8 | 8.604 | 8.144 | 103 | 1116 | 1219 |
| HiBCSoy60 | 40.1 | 9.6 | 6.1 | 7.8 | 6.1 | 15.7 | 21.8 | 7.463 | 7.468 | 1671 | 4330 | 6001 |
| HiBCSoy43 | 37.3 | 7.9 | 9.7 | 6.2 | 4.6 | 17.6 | 22.1 | 5.111 | 6.575 | 209 | 1083 | 1292 |
| HiBCSoy25 | 44.2 | 10.0 | 8.5 | 8.3 | 3.9 | 18.4 | 22.3 | 6.642 | 7.495 | 686 | 1666 | 2352 |
| HiBCSoy50 | 46.3 | 8.8 | 6.0 | 6.2 | 7.6 | 14.8 | 22.3 | 7.072 | 6.590 | 115 | 1339 | 1454 |
| HiBCSoy13 | 45.4 | 11.4 | 5.3 | 2.8 | 5.9 | 16.7 | 22.6 | 7.421 | 8.778 | 508 | 2290 | 2798 |
| HiBCSoy55 | 37.8 | 9.2 | 7.8 | 4.5 | 6.1 | 17.1 | 23.1 | 6.848 | 6.503 | 1705 | 4929 | 6634 |
| HiBCSoy54 | 31.2 | 9.9 | 6.4 | 2.8 | 6.9 | 16.3 | 23.2 | 5.994 | 5.363 | 752 | 1569 | 2321 |
| HiBCSoy19 | 44.3 | 12.5 | 5.7 | 9.3 | 5.1 | 18.2 | 23.3 | 9.434 | 11.218 | 108 | 1257 | 1365 |
| HiBCSoy14 | 46.1 | 8.8 | 6.5 | 8.6 | 8.2 | 15.3 | 23.5 | 7.974 | 7.297 | 181 | 1334 | 1515 |
| HiBCSoy20 | 41.4 | 10.2 | 8.9 | 10.4 | 4.6 | 19.1 | 23.7 | 6.392 | 10.686 | 1007 | 2329 | 3336 |
| HiBCSoy45 | 45.7 | 9.1 | 9.3 | 3.8 | 5.5 | 18.4 | 23.9 | 7.637 | 15.149 | 169 | 744 | 913 |
| HiBCSoy12 | 48.6 | 10.8 | 7.6 | 4.9 | 6.1 | 18.4 | 24.5 | 9.695 | 10.837 | 92 | 455 | 547 |
| HiBCSoy31 | 42.0 | 12.5 | 6.9 | 11.0 | 5.4 | 19.4 | 24.8 | 12.072 | 6.823 | 66 | 1162 | 1228 |

TABLE 8A-continued

| Sample ID | beta-conglycinin (% of total protein) | hexanal (μg/g) | hexanol (μg/g) | octen-3-ol (μg/g) | decadienal (μg/g) | Hexanal + Hexanol (μg/g) | Hexanal + Hexanol + 2,4 decadienal (μg/g) | Lipox. activity, pH 7 | Lipox. activity, pH 9 | Asn (μg/g) | Arg (μg/g) | Arg + Asn (μg/g) |
|---|---|---|---|---|---|---|---|---|---|---|---|---|
| HiBCSoy7 | 46.5 | 12.5 | 6.0 | 3.8 | 6.5 | 18.5 | 25.0 | 8.042 | 9.921 | 476 | 1641 | 2117 |
| HiBCSoy1 | 45.1 | 12.3 | 6.7 | 6.2 | 6.5 | 19.0 | 25.6 | 8.351 | 7.376 | 187 | 1423 | 1610 |
| HiBCSoy29 | 38.8 | 4.0 | 10.1 | 8.4 | 11.6 | 14.1 | 25.7 | 8.944 | 5.006 | 136 | 818 | 954 |
| HiBCSoy8 | 48.7 | 11.6 | 8.6 | 8.2 | 5.6 | 20.2 | 25.8 | 6.888 | 8.407 | 321 | 2612 | 2933 |
| HiBCSoy56 | 36.4 | 11.5 | 7.7 | 7.5 | 6.9 | 19.2 | 26.1 | 7.312 | 8.601 | 1155 | 2602 | 3757 |
| HiBCSoy51 | 40.4 | 11.5 | 6.0 | 4.2 | 8.7 | 17.5 | 26.2 | 7.622 | 10.635 | 1695 | 3701 | 5396 |
| HiBCSoy47 | 38.1 | 10.0 | 11.6 | 6.4 | 4.8 | 21.6 | 26.4 | 6.974 | 4.039 | 92 | 1013 | 1105 |
| HiBCSoy30 | 36.6 | 9.9 | 11.6 | 3.0 | 5.1 | 21.4 | 26.6 | 11.349 | 4.735 | 158 | 812 | 970 |
| HiBCSoy27 | 38.6 | 11.0 | 12.1 | 8.0 | 4.1 | 23.1 | 27.2 | 7.118 | 4.131 | 633 | 1082 | 1715 |
| HiBCSoy28 | 38.8 | 12.7 | 9.6 | 6.9 | 6.3 | 22.2 | 28.6 | 4.762 | 5.822 | 2575 | 3204 | 5779 |
| HiBCSoy15 | 45.8 | 15.5 | 6.6 | 2.2 | 6.6 | 22.1 | 28.6 | 9.056 | 9.945 | 129 | 620 | 749 |
| HiBCSoy23 | 43.7 | 13.0 | 10.2 | 10.0 | 6.1 | 23.2 | 29.4 | 6.681 | 5.207 | 1136 | 2578 | 3714 |
| HiBCSoy22 | 29.7 | 9.3 | 11.0 | 8.9 | 9.5 | 20.4 | 29.9 | 6.645 | 8.996 | 192 | 844 | 1036 |
| HiBCSoy33 | 41.3 | 16.7 | 7.6 | 6.0 | 7.8 | 24.2 | 32.0 | 8.162 | 9.203 | 576 | 2919 | 3495 |
| HiBCSoy10 | 44.3 | 15.6 | 8.2 | 5.6 | 8.2 | 23.8 | 32.0 | 8.624 | 11.794 | 106 | 1108 | 1214 |
| HiBCSoy21 | 35.7 | 14.5 | 12.0 | 10.8 | 6.1 | 26.5 | 32.6 | 8.634 | 11.921 | 99 | 581 | 680 |
| HiBCSoy9 | 46.9 | 16.6 | 8.7 | 5.9 | 8.7 | 25.2 | 33.9 | 6.976 | 6.340 | 155 | 1430 | 1585 |

TABLE 8B

| Sample ID | Protein (%, dry basis) | A1a, A1b, A2, A4 glycinins (% of total protein) | A3 glycinin | B1a, B1b, B2, B3, B4 glycinins | alpha beta-conglycinin | alpha-prime beta-conglycinin | beta beta-conglycinin | Total beta-conglycinins | Total Glycinins |
|---|---|---|---|---|---|---|---|---|---|
| HiBCSoy52 | 42.76 | 4.872 | 4.784 | 9.097 | 20.849 | 12.381 | 5.123 | 38.353 | 18.753 |
| HiBCSoy70 | 41.78 | 4.179 | 3.563 | 7.039 | 22.621 | 11.596 | 5.262 | 39.479 | 14.781 |
| HiBCSoy41 | 40.49 |  | 5.784 | 1.555 | 23.558 | 14.185 | 5.502 | 43.245 | 7.339 |
| HiBCSoy65 | 43.82 | 4.759 | 5.007 | 7.737 | 22.044 | 12.875 | 4.263 | 39.182 | 17.503 |
| HiBCSoy35 | 40.56 | 2.312 | 4.538 | 4.913 | 22.903 | 12.727 | 6.415 | 42.045 | 11.763 |
| HiBCSoy67 | 42.46 | 4.167 | 3.608 | 8.694 | 23.331 | 11.983 | 5.038 | 40.352 | 16.469 |
| HiBCSoy34 | 41.31 | 3.352 | 4.615 | 4.318 | 22.04 | 12.555 | 5.961 | 40.556 | 12.285 |
| HiBCSoy64 | 43.10 | 4.949 | 5.047 | 7.773 | 21.646 | 12.79 | 4.858 | 39.294 | 17.769 |
| HiBCSoy62 | 44.64 | 4.891 | 5.045 | 6.098 | 22.73 | 12.045 | 6.309 | 41.084 | 16.034 |
| HiBCSoy68 | 42.56 | 3.849 | 3.209 | 7.343 | 22.829 | 11.403 | 6.297 | 40.529 | 14.401 |
| HiBCSoy61 | 38.94 | 4.274 | 4.172 | 10.014 | 17.347 | 9.747 | 3.206 | 30.3 | 18.46 |
| HiBCSoy69 | 42.64 | 4.468 | 3.81 | 8.614 | 22.386 | 11.791 | 5.713 | 39.89 | 16.892 |
| HiBCSoy48 | 39.72 |  | 6.168 | 2.907 | 24.062 | 15.07 | 5.414 | 44.546 | 9.075 |
| HiBCSoy40 | 41.18 |  | 6.068 | 1.264 | 23.629 | 14.878 | 6.525 | 45.032 | 7.332 |
| HiBCSoy11 | 44.68 |  | 6.886 | 3.09 | 24.802 | 13.863 | 9.552 | 48.217 | 9.976 |
| HiBCSoy42 | 38.13 | 1.822 | 4.93 | 3.401 | 20.961 | 11.577 | 6.06 | 38.598 | 10.153 |
| HiBCSoy53 | 43.66 | 4.782 | 4.783 | 8.585 | 22.103 | 12.521 | 5.373 | 39.997 | 18.15 |
| HiBCSoy5 | 45.03 |  | 5.869 | 2.944 | 24.794 | 13.653 | 8.089 | 46.536 | 8.813 |
| HiBCSoy36 | 38.50 | 2.463 | 4.221 | 3.665 | 22.435 | 11.65 | 6.532 | 40.617 | 10.349 |
| HiBCSoy3 | 42.55 |  | 6.308 | 3.171 | 25.442 | 14.402 | 6.927 | 46.771 | 9.479 |
| HiBCSoy4 | 43.56 |  | 5.449 | 2.765 | 23.395 | 14.297 | 7.2 | 44.892 | 8.214 |
| HiBCSoy46 | 39.89 |  | 6.149 | 1.453 | 23.323 | 14.892 | 4.155 | 42.37 | 7.602 |
| HiBCSoy26 | 41.21 |  | 5.742 | 2.31 | 23.643 | 14.391 | 6.636 | 44.67 | 8.052 |
| HiBCSoy18 | 40.14 |  | 5.385 | 1.875 | 23.836 | 14.999 | 5.934 | 44.769 | 7.26 |
| HiBCSoy6 | 42.40 |  | 5.598 | 2.769 | 24.62 | 13.114 | 8.123 | 45.857 | 8.367 |
| HiBCSoy17 | 39.74 |  | 5.788 | 2.281 | 22.884 | 13.984 | 6.816 | 43.684 | 8.069 |
| HiBCSoy44 | 39.01 | 4.766 | 4.241 | 8.322 | 17.716 | 9.373 | 4.63 | 31.719 | 17.329 |
| HiBCSoy63 | 41.95 | 3.372 | 3.558 | 11.179 | 17.431 | 10.613 | 5.467 | 33.511 | 18.109 |
| HiBCSoy57 | 43.94 | 5.167 | 5.105 | 8.459 | 21.038 | 11.288 | 4.558 | 36.884 | 18.731 |
| HiBCSoy16 | 40.83 |  | 5.284 | 2.94 | 23.351 | 14.266 | 6.694 | 44.311 | 8.224 |
| HiBCSoy24 | 43.66 | 2.799 | 4.931 | 5.949 | 23.351 | 13.832 | 6.508 | 43.691 | 13.679 |
| HiBCSoy58 | 43.60 | 5.132 | 4.262 | 8.898 | 21.14 | 11.418 | 3.834 | 36.392 | 18.292 |
| HiBCSoy39 | 37.61 | 2.666 | 5.814 | 5.48 | 21.436 | 13.648 | 6.63 | 41.714 | 13.96 |
| HiBCSoy66 | 44.77 | 5.063 | 4.755 | 9.443 | 21.266 | 12.448 | 5.5 | 39.214 | 19.261 |
| HiBCSoy38 | 38.42 | 3.923 | 3.871 | 5.194 | 20.716 | 11.702 | 5.154 | 37.572 | 12.988 |
| HiBCSoy59 | 40.54 | 4.696 | 4.26 | 7.023 | 21.554 | 12.26 | 3.384 | 37.198 | 15.979 |
| HiBCSoy37 | 38.99 | 4.581 | 4.392 | 6.76 | 19.84 | 10.994 | 5.954 | 36.788 | 15.733 |
| HiBCSoy2 | 41.47 |  | 5.872 | 2.553 | 25.298 | 13.934 | 6.684 | 45.916 | 8.425 |
| HiBCSoy60 | 43.40 | 5.019 | 4.688 | 7.532 | 22.035 | 12.045 | 5.976 | 40.056 | 17.239 |
| HiBCSoy43 | 43.12 | 4.856 | 4.538 | 7.757 | 20.84 | 12.396 | 4.097 | 37.333 | 17.151 |
| HiBCSoy25 | 42.23 |  | 5.976 | 3.074 | 23.404 | 14.578 | 6.257 | 44.239 | 9.05 |
| HiBCSoy50 | 41.44 |  | 6.019 | 1.903 | 25.113 | 16.165 | 4.972 | 46.25 | 7.922 |
| HiBCSoy13 | 45.51 |  | 5.732 | 2.562 | 24.536 | 13.744 | 7.135 | 45.415 | 8.294 |
| HiBCSoy55 | 43.70 | 5.036 | 4.671 | 8.171 | 20.641 | 12.032 | 5.142 | 37.815 | 17.878 |

TABLE 8B-continued

| Sample ID | Protein (%, dry basis) | A1a, A1b, A2, A4 glycinins (% of total protein) | A3 glycinin | B1a, B1b, B2, B3, B4 glycinins | alpha beta-conglycinin | alpha-prime beta-conglycinin | beta beta-conglycinin | Total beta-conglycinins | Total Glycinins |
|---|---|---|---|---|---|---|---|---|---|
| HiBCSoy54 | 42.39 | 3.604 | 3.3 | 12.991 | 16.118 | 10.006 | 5.063 | 31.187 | 19.895 |
| HiBCSoy19 | 41.60 | | 6.109 | 2.67 | 22.8 | 14.199 | 7.284 | 44.283 | 8.779 |
| HiBCSoy14 | 42.22 | | 5.431 | 2.557 | 24.628 | 14.439 | 7.002 | 46.069 | 7.988 |
| HiBCSoy20 | 41.04 | 1.577 | 4.913 | 4.422 | 21.592 | 13.422 | 6.411 | 41.425 | 10.912 |
| HiBCSoy45 | 40.13 | | 5.347 | 2.737 | 24.384 | 14.056 | 7.308 | 45.748 | 8.084 |
| HiBCSoy12 | 39.59 | | 5.842 | 3.582 | 26.33 | 15.218 | 7.082 | 48.63 | 9.424 |
| HiBCSoy31 | 40.25 | 1.7 | 4.33 | 2.41 | 22.579 | 13.279 | 6.133 | 41.991 | 8.44 |
| HiBCSoy7 | 42.12 | | 5.905 | 2.788 | 25.149 | 13.985 | 7.401 | 46.535 | 8.693 |
| HiBCSoy1 | 40.11 | | 5.451 | 2.366 | 23.373 | 13.84 | 7.865 | 45.078 | 7.817 |
| HiBCSoy29 | 40.01 | 3.919 | 3.571 | 6.9 | 20.207 | 13.234 | 5.345 | 38.786 | 14.39 |
| HiBCSoy8 | 46.86 | | 6.055 | 3.495 | 25.584 | 14.699 | 8.464 | 48.747 | 9.55 |
| HiBCSoy56 | 42.14 | 4.915 | 4.981 | 8.294 | 21.474 | 12.173 | 2.736 | 36.383 | 18.19 |
| HiBCSoy51 | 42.24 | 4.303 | 4.695 | 7.503 | 22.456 | 13.402 | 4.535 | 40.393 | 16.501 |
| HiBCSoy47 | 39.32 | | 5.83 | 1.61 | 20.486 | 11.803 | 5.835 | 38.124 | 7.44 |
| HiBCSoy30 | 43.28 | 4.796 | 4.07 | 8.302 | 19.29 | 11.788 | 5.555 | 36.633 | 17.168 |
| HiBCSoy27 | 43.71 | 4.651 | 4.769 | 7.697 | 20.396 | 12.062 | 6.173 | 38.631 | 17.117 |
| HiBCSoy28 | 44.14 | 5.017 | 4.986 | 8.742 | 20.351 | 12.578 | 5.915 | 38.844 | 18.745 |
| HiBCSoy15 | 42.65 | | 6.124 | 2.44 | 23.224 | 14.71 | 7.892 | 45.826 | 8.564 |
| HiBCSoy23 | 41.51 | 2.38 | 5.072 | 5.094 | 23.148 | 13.627 | 6.932 | 43.707 | 12.546 |
| HiBCSoy22 | 42.24 | 5.253 | 4.672 | 9.326 | 14.996 | 9.178 | 5.509 | 29.683 | 19.251 |
| HiBCSoy33 | 41.71 | 2.126 | 5.273 | 4.404 | 22.994 | 13.025 | 5.292 | 41.311 | 11.803 |
| HiBCSoy10 | 41.40 | | 5.364 | 2.383 | 23.984 | 15.345 | 4.929 | 44.258 | 7.747 |
| HiBCSoy21 | 39.50 | 3.867 | 3.566 | 6.852 | 18.347 | 11.398 | 5.944 | 35.689 | 14.285 |
| HiBCSoy9 | 42.92 | | 6.2 | 2.45 | 24.453 | 14.776 | 7.647 | 46.876 | 8.65 |

Lipoxygenase activities varied significantly for high β-conglycinin soybean samples. There was no relation between lipoxygenase activities at pH 7 and at pH 9 and the total amounts of 2,4 decadienal plus hexanal plus hexanol produced from the same soybean flour ($R^2$ values <0.02).

An additional experiment was conducted to demonstrate that soybeans having greater than 30% β-conglycinin and less than 25% glycinins can be selected that have low color and an amino acid composition that is within the range of commodity soybeans. Four high β-conglycinin soybeans that also contained Roundup Ready® trait, were selected that yielded the same or better than the average of commercial checks in three locations. These soybeans had the low color trait as illustrated by an average b* of about 22 and an average L* of about 85 (Table 9). The amino acid compositions (Table 9) fell within the ranges for commodity soybeans (Table 10) as published in the International Life Sciences Institute Crop Composition Database (Version 1.0, accessed Mar. 22, 2004). The average amino acid compositions of three high β-conglycinin soybean lines (Table 9) were compared to the average soybean composition in the ILSI database (Table 10). Four amino acids (arginine, lysine, histidine and serine) of the high β-conglycinin lines were between 10 and 15% different from the average composition of commodity soybeans but were still within the range of commodity soybean compositions.

It is also anticipated that the organoleptic properties of high β-conglycinin soybeans will be further improved by crossing with low linolenic, mid-oleic soybeans. The low linolenic, mid-oleic soybeans were created at Monsanto using traditional breeding and comprise a linolenic content of about 2%, the linoleic content of about 25% and the oleic acid content of about 59% of the total fatty acids.

TABLE 9

Composition, color and odor properties of soybeans grown in three locations in 2003. All had Roundup Ready ® trait and dark hilum.

| | HBC-360 average | stdev | HBC-350 average | stdev | HBC-390 average | stdev |
|---|---|---|---|---|---|---|
| Beta-conglycinins (% of total protein) | 37.4 | 1.5 | 37.0 | 0.3 | 37.9 | 1.0 |
| Glycinins (% of total protein) | 15.4 | 0.8 | 15.2 | 1.3 | 17.1 | 0.5 |
| Free Asn (ppm) | 307 | 224 | 183 | 124 | 535 | 309 |
| Free Arg (ppm) | 2825 | 1211 | 2050 | 829 | 2791 | 674 |
| Color | | | | | | |
| b* | 22.0 | 1.6 | 23.3 | 1.9 | 22.7 | 0.6 |
| L* | 85.4 | 0.4 | 85.6 | 0.7 | 84.8 | 0.1 |
| Odor | | | | | | |
| hexanal + hexanol + 2,4 decadienal (µg/g soybean) Proximate (g/100 g soybean) | 25.1 | 1.2 | 53.7 | 17.0 | 29.4 | 1.0 |
| Moisture | 5.91 | 0.06 | 5.855 | 0.09 | 5.97 | 0.11 |
| Protein | 37.40 | 1.15 | 36.05 | 0.49 | 37.87 | 1.62 |

TABLE 9-continued

Composition, color and odor properties of soybeans grown in three locations in 2003. All had Roundup Ready ® trait and dark hilum.

| | | | | | | | | |
|---|---|---|---|---|---|---|---|---|
| Total Fat | 17.53 | 0.25 | | 18.2 | 0.42 | | 16.27 | 0.15 |
| Ash | 4.41 | 0.28 | | 4.45 | 0.18 | | 4.36 | 0.14 |
| Carbohydrates | 34.77 | 0.80 | | 35.45 | 0.21 | | 35.57 | 1.59 |

| Amino Acids | mg/g soybean | | mg/g protein | mg/g soybean | | mg/g protein | mg/g soybean | | mg/g protein |
|---|---|---|---|---|---|---|---|---|---|
| Aspartic Acid | 39.90 | 0.95 | 106.68 | 40.05 | 0.35 | 111.10 | 42.50 | 1.01 | 112.24 |
| Threonine | 12.70 | 0.60 | 33.96 | 12.3 | 1.70 | 34.12 | 12.37 | 0.21 | 32.66 |
| Serine | 19.70 | 0.72 | 52.67 | 20.25 | 1.20 | 56.17 | 21.40 | 0.46 | 56.51 |
| Glutamic Acid | 62.67 | 1.79 | 167.56 | 62.7 | 0.42 | 173.93 | 67.13 | 1.16 | 177.29 |
| Proline | 18.33 | 0.38 | 49.02 | 18.35 | 0.07 | 50.90 | 18.67 | 0.49 | 49.30 |
| Glycine | 15.27 | 0.32 | 40.82 | 15.2 | 0.00 | 42.16 | 15.80 | 0.26 | 41.73 |
| Alanine | 15.57 | 0.32 | 41.62 | 15.6 | 0.00 | 43.27 | 15.90 | 0.20 | 41.99 |
| Cystine | 5.31 | 0.34 | 14.21 | 5.915 | 0.06 | 16.41 | 5.81 | 0.33 | 15.33 |
| Valine | 17.13 | 0.72 | 45.81 | 17.1 | 0.14 | 47.43 | 17.63 | 0.25 | 46.57 |
| Methionine | 4.45 | 0.47 | 11.89 | 4.85 | 0.06 | 13.45 | 4.83 | 0.11 | 12.75 |
| Isoleucine | 16.33 | 0.55 | 43.67 | 16.4 | 0.14 | 45.49 | 16.67 | 0.25 | 44.01 |
| Leucine | 27.80 | 0.78 | 74.33 | 27.95 | 0.07 | 77.53 | 28.93 | 0.25 | 76.41 |
| Tyrosine | 12.33 | 0.15 | 32.98 | 12.55 | 0.07 | 34.81 | 12.90 | 0.53 | 34.07 |
| Phenylalanine | 18.37 | 0.61 | 49.11 | 18.4 | 0.00 | 51.04 | 18.83 | 0.31 | 49.74 |
| Histidine | 10.53 | 0.35 | 28.16 | 10.5 | 0.14 | 29.13 | 11.17 | 0.31 | 29.49 |
| Lysine | 25.07 | 0.93 | 67.02 | 24.85 | 0.07 | 68.93 | 26.13 | 0.80 | 69.01 |
| Arginine | 27.03 | 1.45 | 72.28 | 26.45 | 0.49 | 73.37 | 30.17 | 1.75 | 79.67 |
| Tryptophan | 3.96 | 0.11 | 10.58 | 3.945 | 0.02 | 10.94 | 4.20 | 0.17 | 11.08 |
| Met + Cys | | | 26.10 | | | 29.86 | | | 28.08 |

TABLE 10

Comparison of the average composition of three high beta-conglycinin soybeans with the average soybean composition in the International Life Sciences Institute Crop Composition Database (Version 1.0). Selection criteria used for obtaining the data: crop type, soybeans-Glycine max, tissue type: seed, crop year, all, country, all, state, all. Abbreviations: FW = soybean flour weight. DW = dry weight

| Analyte | Min.imum | Maximum | Avg. | n | Units | Average HBC soybeans (mg/g FW) | Difference from ILSI average (%) |
|---|---|---|---|---|---|---|---|
| Amino_Acids - Alanine | 13.6 | 17.2 | 15.35 | 187 | mg/g FW | 15.7 | 2.2 |
| Amino_Acids - Arginine | 20.9 | 31.3 | 25.31 | 187 | mg/g FW | 27.9 | 10.2 |
| Amino_Acids - Aspartic Acid | 33.9 | 46.6 | 40.16 | 187 | mg/g FW | 40.8 | 1.6 |
| Amino_Acids - Cystine/Cysteine | 3.43 | 7.29 | 5.26 | 187 | mg/g FW | 5.7 | 8.0 |
| Amino_Acids - Glutamic Acid | 52.8 | 74 | 63.24 | 187 | mg/g FW | 64.2 | 1.5 |
| Amino_Acids - Glycine | 13.1 | 17.4 | 15.03 | 187 | mg/g FW | 15.4 | 2.6 |
| Amino_Acids - Histidine | 8.07 | 10.8 | 9.32 | 187 | mg/g FW | 10.7 | 15.2 |
| Amino_Acids - Isoleucine | 13.3 | 19 | 16.19 | 187 | mg/g FW | 16.5 | 1.7 |
| Amino_Acids - Leucine | 23.1 | 31.5 | 27.04 | 187 | mg/g FW | 28.2 | 4.4 |
| Amino_Acids - Lysine | 20 | 26.6 | 22.88 | 187 | mg/g FW | 25.4 | 10.8 |
| Amino_Acids - Methionine | 3.99 | 6.14 | 4.92 | 187 | mg/g FW | 4.7 | −4.3 |
| Amino_Acids - Phenylalanine | 14.6 | 20.5 | 17.69 | 187 | mg/g FW | 18.5 | 4.8 |
| Amino_Acids - Proline | 15.1 | 21.2 | 18.05 | 187 | mg/g FW | 18.5 | 2.2 |
| Amino_Acids - Serine | 15 | 22.8 | 18.12 | 187 | mg/g FW | 20.5 | 12.9 |
| Amino_Acids - Threonine | 11.5 | 15.1 | 12.99 | 187 | mg/g FW | 12.5 | −4.1 |
| Amino_Acids - Tryptophan | 3.26 | 4.7 | 3.903 | 187 | mg/g FW | 4.0 | 3.3 |
| Amino_Acids - Tyrosine | 8.7 | 14.3 | 11.78 | 187 | mg/g FW | 12.6 | 6.9 |
| Amino_Acids - Valine | 14.5 | 20.5 | 17.14 | 187 | mg/g FW | 17.3 | 0.9 |

| Analyte | Minimum | Maximum | Average | n | Units | | |
|---|---|---|---|---|---|---|---|
| Proximates - Ash | 3.885 | 6.542 | 5.313 | 237 | % DW | | |
| Proximates - Carbohydrate By Calculation | 29.6 | 50.2 | 38.1 | 237 | % DW | | |
| Proximates - Crude Protein | 33.19 | 45.48 | 39.28 | 237 | % DW | | |
| Proximates - Total Fat | 8.104 | 23.562 | 16.94 | 237 | % DW | | |

EXAMPLE 5

Comparison of Odor and Color Properties of Commodity Soybeans with Soybeans Selected According to the Invention The odor and color properties of commodity soybeans were determined to compare with the odor and color properties of soybeans of the invention. Some soybeans produced less than 17.5 µg/g of hexanal plus hexanol and some produced less than 11 µg/g of 2,4 decadienal in the odor assay (Table 11). However, none of the commodity soybeans produced less than 20 µg of total 2,4 decadienal plus hexanal plus hexanol per gram of ground seeds following oxidation under mild aqueous conditions. Four lipoxygenase-containing lines of this invention were created that produced less than 20 µg/g of hexanal+hexanol+2,4 decadienal in two seasons (Tables 4, 5). For example, line A-1 from 2001 and 2002 harvests produced 18.0 and 18.2 µg/g, respectively of the sum of hexanal+hexanol and 2,4 decadienal (Tables 4, 5). More than 20 high β-conglycinin lines were created by the invention that produced had less than 20 µg/g of the total of hexanal+hexanol and 2,4 decadienal (Table 8). For example, one high βconglycinin soybean produced 9.7 µg/g hexanal+hexanol and 3.2 µg/g of 2,4 decadienal (Table 8).

The color of commodity soybeans covered a broad range. For example the b* value ranged from 27 to 34 (Table 11). The soybean lines of the invention were found to extend to values of b* as low as 22 (Table 4, Table 9).

TABLE 11A

| | | | Flavor | | | |
|---|---|---|---|---|---|---|
| Sample number | hexanal (pg/g) | Hexanal (pg/g) | Hexanol + (pg/g) | 2,4 decadienal | 1-octen-3-ol (MS'S) | 2,4 decadienal + hexanal + hexanol (µg/g) |
| 385 | 14.0 | 3.9 | 18.0 | 2.8 | 1.8 | 20.7 |
| 493 | 5.0 | 5.1 | 10.1 | 11.1 | 5.4 | 21.2 |
| 491-2 | 5.0 | 4.4 | 9.4 | 14.3 | 6.1 | 23.7 |
| 210 | 15.4 | 5.1 | 20.5 | 3.6 | 7.0 | 24.1 |
| 287 | 14.0 | 3.6 | 17.6 | 7.2 | 18.4 | 24.8 |
| 387 | 15.6 | 3.9 | 19.6 | 5.3 | 8.5 | 24.8 |
| 138 | 14.9 | 5.0 | 19.9 | 5.0 | 9.3 | 24.9 |
| 379 | 17.4 | 4.1 | 21.5 | 3.4 | 9.1 | 24.9 |
| 137 | 15.0 | 4.8 | 19.9 | 5.1 | 8.4 | 25.0 |
| 209 | 15.5 | 5.5 | 21.0 | 4.2 | 3.1 | 25.2 |
| 386 | 15.7 | 3.9 | 19.7 | 5.6 | 5.7 | 25.3 |
| 390 | 18.1 | 3.9 | 22.0 | 3.7 | 11.2 | 25.8 |
| 285 | 13.9 | 6.2 | 20.1 | 5.9 | 4.6 | 26.0 |
| 286 | 14.8 | 5.3 | 20.1 | 6.0 | 12.3 | 26.1 |
| 290 | 14.5 | 5.5 | 20.0 | 6.6 | 6.4 | 26.6 |
| 289 | 14.8 | 5.8 | 20.6 | 6.1 | 7.8 | 26.8 |
| 175 | 9.5 | 5.8 | 15.3 | 11.6 | 4.3 | 26.9 |
| 383 | 16.7 | 3.9 | 20.6 | 6.6 | 7.9 | 27.2 |
| 411 | 5.8 | 7.9 | 13.8 | 13.5 | 8.0 | 27.3 |
| 276 | 14.7 | 5.9 | 20.5 | 7.2 | 2.5 | 27.7 |
| 378 | 17.7 | 3.9 | 21.6 | 6.2 | 9.6 | 27.8 |
| 282 | 15.5 | 6.1 | 21.7 | 6.1 | 5.8 | 27.8 |
| 224 | 14.5 | 5.3 | 19.8 | 8.1 | 2.1 | 28.0 |
| 139 | 17.0 | 5.2 | 22.2 | 6.0 | 7.3 | 28.1 |
| 492 | 4.9 | 4.5 | 9.3 | 19.0 | 4.5 | 28.3 |
| 216 | 16.1 | 5.8 | 21.8 | 6.7 | 2.2 | 28.5 |
| 381 | 19.3 | 4.1 | 23.4 | 5.2 | 9.7 | 28.5 |
| 384 | 18.5 | 4.1 | 22.6 | 6.0 | 12.4 | 28.6 |
| 288 | 15.9 | 5.2 | 21.1 | 7.5 | 1.4 | 28.7 |
| 280 | 17.4 | 6.1 | 23.5 | 5.2 | 3.7 | 28.7 |
| 557 | 18.9 | 6.1 | 25.0 | 3.6 | 5.7 | 28.7 |
| 206-2 | 17.6 | 5.1 | 22.8 | 5.9 | 6.0 | 28.7 |
| 141 | 17.6 | 5.6 | 23.3 | 5.5 | 9.1 | 28.7 |
| 271 | 15.9 | 7.0 | 22.9 | 5.8 | 3.3 | 28.7 |
| 299 | 15.8 | 4.8 | 20.6 | 8.3 | 2.7 | 29.0 |
| 208 | 17.9 | 5.1 | 23.0 | 6.1 | 4.8 | 29.0 |
| 495 | 5.0 | 5.6 | 10.5 | 18.5 | 5.8 | 29.1 |
| 284 | 18.6 | 6.3 | 24.9 | 4.2 | 1.7 | 29.1 |
| 211 | 18.5 | 5.9 | 24.4 | 4.7 | 4.3 | 29.1 |
| 486 | 4.9 | 3.3 | 8.2 | 21.0 | 6.7 | 29.1 |
| 215 | 16.4 | 6.1 | 22.5 | 6.7 | 2.5 | 29.2 |
| 142 | 16.7 | 5.3 | 22.0 | 7.2 | 13.1 | 29.2 |
| 485 | 5.1 | 5.3 | 10.3 | 18.9 | 5.3 | 29.2 |
| 271-2 | 15.3 | 7.3 | 22.6 | 6.7 | 4.0 | 29.3 |
| 494 | 5.1 | 6.2 | 11.2 | 18.1 | 3.7 | 29.4 |
| 388 | 18.5 | 4.0 | 22.6 | 6.9 | 7.9 | 29.4 |
| 444 | 12.0 | 5.6 | 17.6 | 11.9 | 2.6 | 29.5 |
| 291 | 15.8 | 6.4 | 22.2 | 7.4 | 2.2 | 29.6 |
| 377-2 | 17.1 | 3.8 | 20.9 | 8.76 | 4.6 | 29.6 |
| 140 | 16.5 | 6.5 | 22.9 | 9 | 3.7 | 29.9 |
| 249 | 18.2 | 5.1 | 23.9 | 6.0 | 5.2 | 29.9 |
| 293 | 15.5 | 5.0 | 20.4 | 9.6 | 6.5 | 30.0 |
| 292 | 15.5 | 5.8 | 21.3 | 8.7 | 2.4 | 30.1 |
| 275 | 17.3 | 7.5 | 24.8 | 5.3 | 4.4 | 30.1 |
| 274 | 16.4 | 6.7 | 23.1 | 7.1 | 5.7 | 30.2 |

TABLE 11A-continued

Flavor

| Sample number | hexanal (pg/g) | Hexanal (pg/g) | Hexanol + (pg/g) | 2,4 decadienal | 1-octen-3-ol (MS'S) | 2,4 decadienal + hexanal + hexanol (μg/g) |
|---|---|---|---|---|---|---|
| 296 | 13.9 | 6.6 | 20.6 | 9.8 | 3.0 | 30.4 |
| 260 | 16.2 | 5.8 | 22.0 | 8.4 | 4.9 | 30.4 |
| 213 | 17.3 | 4.9 | 22.2 | 8.3 | 2.5 | 30.5 |
| 295 | 15.4 | 5.7 | 21.2 | 9.5 | 5.6 | 30.7 |
| 570 | 17.6 | 6.8 | 24.4 | 6.3 | 4.1 | 30.7 |
| 235 | 16.2 | 4.8 | 21.0 | 9.8 | 7.2 | 30.8 |
| 490 | 5.1 | 5.0 | 10.1 | 20.8 | 5.7 | 30.9 |
| 294 | 17.5 | 6.1 | 23.7 | 7.2 | 4.3 | 30.9 |
| 481 | 4.9 | 4.2 | 9.1 | 21.8 | 4.3 | 30.9 |
| 380 | 20.1 | 4.1 | 24.2 | 6.8 | 7.2 | 31.0 |
| 206 | 17.8 | 5.2 | 22.9 | 8.1 | 5.9 | 31.1 |
| 377 | 18.6 | 3.8 | 22.4 | 8.6 | 5.6 | 31.1 |
| 382 | 21.3 | 4.0 | 25.2 | 6.0 | 5.6 | 31.3 |
| 481-2 | 5.1 | 1.9 | 7.0 | 24.5 | 5.0 | 31.4 |
| 262 | 16.9 | 5.6 | 22.4 | 9.0 | 4.8 | 31.5 |
| 279 | 18.1 | 8.1 | 26.2 | 5.3 | 2.8 | 31.5 |
| 300 | 16.8 | 5.9 | 22.8 | 8.8 | 6.2 | 31.5 |
| 227 | 16.9 | 6.0 | 22.9 | 8.6 | 1.9 | 31.5 |
| 298 | 14.9 | 6.0 | 20.9 | 10.7 | 3.8 | 31.6 |
| 231 | 18.6 | 6.4 | 25.0 | 6.8 | 9.0 | 31.8 |
| 220 | 17.4 | 7.0 | 24.4 | 7.4 | 4.0 | 31.9 |
| 400 | 7.5 | 9.1 | 16.6 | 15.4 | 6.8 | 32.0 |
| 482 | 5.1 | 6.7 | 11.7 | 20.2 | 4.3 | 32.0 |
| 125 | 16.7 | 4.4 | 21.1 | 10.9 | 2.2 | 32.0 |
| 225 | 18.0 | 5.8 | 23.8 | 8.3 | 0.6 | 32.1 |
| 539 | 20.4 | 5.8 | 26.2 | 5.9 | 3.8 | 32.1 |
| 212 | 17.0 | 3.8 | 20.8 | 11.3 | 8.8 | 32.1 |
| 281 | 17.2 | 8.0 | 25.2 | 7.0 | 6.6 | 32.2 |
| 36 | 17.1 | 5.1 | 22.2 | 10.0 | 0.0 | 32.3 |
| 192 | 10.4 | 6.5 | 16.9 | 15.6 | 5.4 | 32.5 |
| 551 | 20.3 | 8.0 | 28.2 | 4.3 | 4.4 | 32.5 |
| 416 | 7.3 | 7.0 | 14.3 | 18.4 | 6.3 | 32.7 |
| 547 | 20.8 | 6.4 | 27.2 | 5.6 | 4.1 | 32.8 |
| 277 | 18.7 | 6.4 | 25.1 | 1.9 | 5.3 | 32.9 |
| 248 | 20.7 | 5.7 | 26.4 | 6.1 | 6.5 | 33.0 |
| 267 | 17.0 | 5.6 | 22.5 | 10.6 | 4.9 | 33.1 |
| 232 | 16.5 | 6.1 | 22.6 | 10.5 | 3.0 | 33.1 |
| 11 | 16.0 | 6.4 | 22.4 | 10.7 | 2.6 | 33.1 |
| 245 | 18.3 | 6.8 | 25.0 | 8.1 | 1.5 | 33.1 |
| 401 | 21.5 | 5.9 | 27.5 | 5.7 | 8.9 | 33.1 |
| 255 | 19.2 | 7.2 | 26.4 | 7.1 | 5.1 | 33.5 |
| 230 | 17.7 | 6.3 | 24.0 | 9.4 | 2.8 | 33.5 |
| 283 | 20.4 | 5.9 | 26.3 | 7.3 | 1.1 | 33.6 |
| 349 | 11.4 | 8.0 | 19.4 | 14.4 | 2.4 | 33.8 |
| 166 | 8.3 | 8.7 | 17.0 | 16.8 | 4.1 | 33.8 |
| 272 | 19.5 | 7.5 | 27.1 | 6.8 | 0.8 | 33.9 |
| 483 | 5.1 | 2.0 | 7.1 | 26.9 | 3.5 | 33.9 |
| 236 | 19.3 | 6.3 | 25.6 | 8.4 | 0.4 | 34.0 |
| 491 | 5.1 | 4.6 | 9.6 | 24.4 | 6.9 | 34.0 |
| 571 | 21.0 | 7.3 | 28.3 | 5.8 | 3.0 | 34.1 |
| 376-2 | 21.1 | 3.9 | 25.0 | 9.1 | 5.7 | 34.1 |
| 147 | 20.7 | 5.5 | 26.1 | 8.1 | 13.9 | 34.2 |
| 148 | 19.4 | 6.0 | 25.4 | 9.2 | 8.6 | 34.7 |
| 266 | 18.6 | 6.1 | 24.6 | 10.0 | 0.5 | 34.7 |
| 242 | 20.1 | 5.6 | 25.8 | 9.1 | 2.8 | 34.9 |
| 222-2 | 18.5 | 5.4 | 23.9 | 10.9 | 5.3 | 34.9 |
| 250 | 20.6 | 6.2 | 26.8 | 8.1 | 8.5 | 34.9 |
| 222 | 18.3 | 5.3 | 23.6 | 11.3 | 5.2 | 34.9 |
| 549 | 21.2 | 8.6 | 29.7 | 5.3 | 3.9 | 35.1 |
| 41 | 20.7 | 6.2 | 26.9 | 8.3 | 4.06 | 35.2 |
| 219 | 19.0 | 6.4 | 25.4 | 9.8 | 2 | 35.2 |
| 278 | 19.5 | 7.5 | 27.0 | 8.3 | 2.7 | 35.2 |
| 149 | 20.2 | 5.4 | 25.6 | 9.79 | 11.2 | 35.3 |
| 233 | 19.4 | 6.8 | 26.2 | 2 | 1.4 | 35.4 |
| 185 | 14.2 | 5.5 | 19.7 | 15.7 | 5.5 | 35.4 |
| 389 | 24.6 | 4.1 | 28.7 | 6.8 | 2.3 | 35.4 |
| 221 | 21.4 | 5.3 | 26.7 | 8.7 | 5.8 | 35.5 |
| 348 | 19.2 | 5.7 | 24.8 | 10.7 | 3.6 | 35.5 |
| 136-2 | 20.0 | 4.8 | 24.8 | 10.8 | 11.5 | 35.6 |
| 218 | 19.1 | 6.1 | 25.2 | 10.5 | 7.1 | 35.8 |
| 217 | 19.1 | 5.7 | 24.8 | 11.1 | 16.6 | 35.9 |
| 256 | 18.4 | 6.1 | 24.5 | 11.4 | 6.0 | 36.0 |
| 555 | 24.2 | 7.4 | 31.5 | 4.5 | 5.3 | 36.0 |
| 346 | 19.8 | 6.5 | 26.2 | 9.7 | 3.1 | 36.0 |

TABLE 11A-continued

Flavor

| Sample number | hexanal (pg/g) | Hexanal (pg/g) | Hexanol + (pg/g) | 2,4 decadienal | 1-octen-3-ol (MS'S) | 2,4 decadienal + hexanal + hexanol (µg/g) |
|---|---|---|---|---|---|---|
| 489 | 5.1 | 4.4 | 9.5 | 26.6 | 5.4 | 36.1 |
| 228 | 20.6 | 6.2 | 26.8 | 9.3 | 7.2 | 36.1 |
| 261 | 18.2 | 7.0 | 25.3 | 10.9 | 1.1 | 36.2 |
| 189 | 14.1 | 6.0 | 20.1 | 16.2 | 12.7 | 36.3 |
| 566 | 22.1 | 7.8 | 29.9 | 6.4 | 0.8 | 36.3 |
| 404 | 22.7 | 6.0 | 28.7 | 7.9 | 4.9 | 36.5 |
| 114 | 22.5 | 3.2 | 25.7 | 11.0 | 10.7 | 36.7 |
| 136 | 20.0 | 4.8 | 24.8 | 11.9 | 14.6 | 36.7 |
| 102 | 18.8 | 5.3 | 24.0 | 12.8 | 5.8 | 36.8 |
| 376 | 21.9 | 4.1 | 26.0 | 10.9 | 6.3 | 36.9 |
| 352 | 17.5 | 6.9 | 24.4 | 12.8 | 3.4 | 37.2 |
| 223 | 19.4 | 5.9 | 25.4 | 11.9 | 3.1 | 37.2 |
| 544 | 22.6 | 9.6 | 32.2 | 5.1 | 5.1 | 37.3 |
| 40 | 22.0 | 5.6 | 27.6 | 9.8 | 0.9 | 37.4 |
| 545 | 25.4 | 7.5 | 32.9 | 4.5 | 2.7 | 37.4 |
| 488 | 5.1 | 5.2 | 10.3 | 27.2 | 7.0 | 37.5 |
| 559 | 20.9 | 6.9 | 27.8 | 9.7 | 4.9 | 37.5 |
| 18O | 18.6 | 6.5 | 25.1 | 12.5 | 9.8 | 37.5 |
| 417 | 5.5 | 8.1 | 13.6 | 24.1 | 7.6 | 37.7 |
| 143 | 21.4 | 5.8 | 27.1 | 10.6 | 16.0 | 37.7 |
| 428 | 5.1 | 8.5 | 13.5 | 24.2 | 8.3 | 37.8 |
| 487 | 5.1 | 5.3 | 10.3 | 27.5 | 6.6 | 37.8 |
| 358 | 13.3 | 7.5 | 20.8 | 17.1 | 4.2 | 37.9 |
| 305 | 20.7 | 6.8 | 27.5 | 10.4 | 5.9 | 37.9 |
| 173 | 13.8 | 6.4 | 20.3 | 17.8 | 2.3 | 38.1 |
| 561 | 25.7 | 8.2 | 34.0 | 4.1 | 5.4 | 38.1 |
| 405 | 24.8 | 6.2 | 31.1 | 7.1 | 1.9 | 38.1 |
| 259 | 19.2 | 6.8 | 26.1 | 12.2 | 4.2 | 38.3 |
| 202 | 17.1 | 5.6 | 22.7 | 15.6 | 4.7 | 38.3 |
| 297 | 18.1 | 8.0 | 26.0 | 12.3 | 2.1 | 38.3 |
| 270 | 20.1 | 5.6 | 25.7 | 12.7 | 5.0 | 38.4 |
| 39 | 23.0 | 5.9 | 28.8 | 9.6 | 5.7 | 38.4 |
| 177 | 17.0 | 6.4 | 23.5 | 15.0 | 6.5 | 38.5 |
| 223-2 | 21.1 | 6.1 | 27.2 | 11.4 | 3.5 | 38.5 |
| 360 | 14.0 | 7.3 | 21.3 | 17.3 | 3.1 | 38.6 |
| 273 | 22.3 | 6.6 | 29.0 | 9.9 | 7.3 | 38.8 |
| 286-2 | 27.1 | 6.3 | 33.5 | 5.4 | 26.1 | 38.8 |
| 440 | 17.1 | 6.9 | 24.0 | 14.9 | 1.0 | 38.9 |
| 229 | 22.6 | 8.3 | 30.8 | 8.1 | 0.3 | 38.9 |
| 550 | 26.6 | 7.1 | 33.7 | 5.5 | 7.3 | 39.2 |
| 399 | 8.0 | 10.4 | 18.4 | 20.8 | 4.6 | 39.2 |
| 236-2 | 22.9 | 6.2 | 29.0 | 10.3 | 0.8 | 39.3 |
| 247 | 21.8 | 7.0 | 28.7 | 10.7 | 8.6 | 39.4 |
| 45 | 23.1 | 6.2 | 29.3 | 10.1 | 5.7 | 39.4 |
| 484 | 5.1 | 6.1 | 11.2 | 28.5 | 2.1 | 39.7 |
| 558 | 22.5 | 7.5 | 30.0 | 9.7 | 3.5 | 39.7 |
| 432 | 13.5 | 16.0 | 29.5 | 10.3 | 6.1 | 39.8 |
| 556-2 | 25.8 | 6.0 | 31.7 | 8.1 | 7.9 | 39.9 |
| 554 | 22.0 | 8.6 | 30.6 | 9.4 | 3.9 | 40.0 |
| 198 | 18.7 | 5.5 | 24.2 | 15.9 | 5.8 | 40.1 |
| 546 | 26.8 | 7.1 | 33.9 | 6.2 | 4.8 | 40.1 |
| 560 | 22.6 | 7.2 | 29.8 | 10.3 | 4.6 | 40.2 |
| 272-2 | 23.2 | 7.8 | 31.0 | 9.1 | 1.0 | 40.2 |
| 214 | 20.7 | 6.9 | 27.5 | 13.0 | 3.5 | 40.5 |
| 42 | 23.6 | 6.1 | 29.6 | 11.0 | 3.5 | 40.6 |
| 569 | 22.0 | 7.3 | 29.3 | 11.3 | 4.9 | 40.6 |
| 27 | 21.8 | 5.8 | 27.7 | 12.9 | 5.8 | 40.6 |
| 38 | 22.5 | 5.0 | 27.5 | 13.2 | 8.0 | 40.7 |
| 565 | 28.0 | 7.2 | 35.2 | 5.5 | 5.9 | 40.7 |
| 108 | 20.7 | 4.6 | 25.3 | 15.5 | 5.5 | 40.8 |
| 540 | 26.0 | 9.2 | 35.1 | 5.7 | 2.5 | 40.8 |
| 174 | 20.6 | 6.0 | 26.7 | 14.3 | 8.0 | 41.0 |
| 342-2 | 22.9 | 7.1 | 30.0 | 11.0 | 1.6 | 41.0 |
| 315 | 12.0 | 5.6 | 17.6 | 23.5 | 5.3 | 41.1 |
| 538 | 27.5 | 8.O | 35.5 | 5.6 | 5.6 | 41.1 |
| 237-2 | 23.5 | 6.0 | 29.5 | 11.7 | 8.0 | 41.2 |
| 310 | 20.5 | 7.4 | 28.0 | 13.2 | 8.3 | 41.2 |
| 192-2 | 19.6 | 5.1 | 24.7 | 16.6 | 5.9 | 41.3 |
| 354 | 18.9 | 10.7 | 29.6 | 11.8 | 5.0 | 41.3 |
| 391 | 23.5 | 3.8 | 27.3 | 14.1 | 7.1 | 41.4 |
| 146 | 22.4 | 5.6 | 28.0 | 13.6 | 9.3 | 41.6 |
| 418 | 15.9 | 7.0 | 23.0 | 18.6 | 5.7 | 41.6 |
| 263 | 22.1 | 5.8 | 27.9 | 13.7 | 4.0 | 41.7 |
| 573 | 22.7 | 8.7 | 31.4 | 10.4 | 3.9 | 41.8 |

TABLE 11A-continued

| | | | Flavor | | | |
|---|---|---|---|---|---|---|
| Sample number | hexanal (pg/g) | Hexanal (pg/g) | Hexanol + (pg/g) | 2,4 decadienal | 1-octen-3-ol (MS'S) | 2,4 decadienal + hexanal + hexanol (μg/g) |
| 200 | 17.9 | 5.7 | 23.6 | 18.2 | 4.7 | 41.8 |
| 347 | 21.3 | 7.3 | 28.6 | 13.7 | 5.1 | 42.3 |
| 395 | 25.0 | 6.1 | 31.0 | 11.4 | 9.2 | 42.4 |
| 36-2 | 24.1 | 5.1 | 29.2 | 13.3 | 0.4 | 42.5 |
| 237 | 23.1 | 6.3 | 29.4 | 13.1 | 9.1 | 42.5 |
| 251 | 28.2 | 7.6 | 35.7 | 6.8 | 6.0 | 42.5 |
| 22 | 22.8 | 5.7 | 28.5 | 14.1 | 5.5 | 42.6 |
| 335 | 16.3 | 9.1 | 25.4 | 17.2 | 4.3 | 42.6 |
| 256-2 | 22.3 | 7.1 | 29.4 | 13.2 | 9.4 | 42.6 |
| 375 | 23.9 | 3.9 | 27.8 | 14.9 | 4.9 | 42.7 |
| 203 | 19.0 | 5.5 | 24.5 | 18.1 | 6.2 | 42.7 |
| 254 | 25.8 | 6.4 | 32.2 | 10.5 | 3.2 | 42.8 |
| 563 | 22.7 | 7.6 | 30.3 | 12.6 | 2.9 | 42.9 |
| 572 | 25.1 | 7.8 | 33.0 | 9.9 | 2.3 | 42..9 |
| 536 | 26.8 | 5.9 | 32.7 | 10.2 | 6.6 | 42.9 |
| 144 | 24.0 | 5.0 | 29.1 | 13.9 | 15.6 | 43.0 |
| 241 | 27.1 | 5.5 | 32.6 | 10.4 | 6.5 | 43.0 |
| 191 | 14.4 | 6.5 | 20.9 | 22.1 | 4.3 | 43.0 |
| 461 | 26.0 | 1.3 | 27.3 | 15.7 | 6.8 | 43.0 |
| 359 | 22.6 | 7.4 | 30.0 | 13.0 | 4.9 | 43.1 |
| 179 | 20.0 | 5.4 | 25.4 | 17.7 | 10.2 | 43.1 |
| 556 | 26.8 | 3.8 | 30.6 | 12.6 | 7.4 | 43.1 |
| 541-2 | 25.6 | 6.6 | 32.2 | 11.0 | 6.2 | 43.2 |
| 252 | 25.1 | 9.0 | 34.1 | 9.2 | 0.5 | 43.4 |
| 201 | 18.6 | 6.3 | 24.8 | 18.6 | 5.8 | 43.4 |
| 257 | 25.1 | 5.4 | 30.4 | 13.4 | 3.6 | 43.8 |
| 269 | 23.6 | 6.2 | 29.8 | 14.1 | 9.0 | 43.9 |
| 301 | 22.8 | 5.9 | 28.7 | 15.2 | 3.2 | 43.9 |
| 191-2 | 18.9 | 6.6 | 25.5 | 18.4 | 4.3 | 43.9 |
| 190 | 22.6 | 5.7 | 28.4 | 15.6 | 4.4 | 43.9 |
| 407 | 14.8 | 7.1 | 21.9 | 22.1 | 7.4 | 44.0 |
| 562 | 25.1 | 7.8 | 32.9 | 11.2 | 4.2 | 44.1 |
| 178 | 22.5 | 7.9 | 30.4 | 13.8 | 12.8 | 44.1 |
| 244 | 29.7 | 6.7 | 36.4 | 7.8 | 4.7 | 44.2 |
| 445 | 26.4 | 6.7 | 33.1 | 11.1 | 0.8 | 44.2 |
| 151 | 24.8 | 5.4 | 30.3 | 13.9 | 13.4 | 44.2 |
| 111-2 | 16.2 | 13.5 | 29.8 | 14.4 | 7.5 | 44.3 |
| 145 | 25.1 | 6.7 | 31.8 | 12.4 | 16.6 | 44.3 |
| 542 | 23.7 | 6.4 | 30.1 | 14.2 | 1.7 | 44.3 |
| 531 | 28.4 | 5.4 | 33.9 | 10.6 | 7.5 | 44.5 |
| 246 | 22.4 | 6.1 | 28.5 | 16.0 | 3.5 | 44.5 |
| 15 | 25.0 | 5.6 | 30.6 | 13.9 | 3.9 | 44.5 |
| 37 | 27.0 | 5.9 | 33.0 | 11.6 | 5.9 | 44.6 |
| 258 | 23.5 | 6.0 | 29.5 | 15.2 | 1.5 | 44.6 |
| 446 | 22.2 | 7.0 | 29.2 | 15.5 | 6.5 | 44.7 |
| 205 | 20.9 | 5.4 | 26.4 | 18.4 | 5.3 | 44.8 |
| 197 | 20.8 | 5.9 | 26.7 | 18.1 | 5.6 | 44.8 |
| 112 | 24.9 | 51 | 30.6 | 14.3 | 9.7 | 45.0 |
| 72 | 24.7 | 6.4 | 31.1 | 13.9 | 14.1 | 45.0 |
| 240 | 27.5 | 7.3 | 34.8 | 10.3 | 6.9 | 45.1 |
| 460 | 26.7 | 1.8 | 28.5 | 16.6 | 3.6 | 45.1 |
| 153 | 25.5 | 5.3 | 30.8 | 14.3 | 5.0 | 45.1 |
| 534 | 22.6 | 7.8 | 30.3 | 14.9 | 4.2 | 45.2 |
| 447 | 26.7 | 7.0 | 33.8 | 11.6 | 4.8 | 45.3 |
| 57 | 25.9 | 6.5 | 32.4 | 13.0 | 4.9 | 45.4 |
| 132 | 24.4 | 5.1 | 30.1 | 15.4 | 9.1 | 45.5 |
| 332 | 22.4 | 6.8 | 29.2 | 16.2 | 2.2 | 45.5 |
| 3 | 19.8 | 5.5 | 25.3 | 20.2 | 3.2 | 45.5 |
| 181 | 23.2 | 5.4 | 28.5 | 17.1 | 6.2 | 45.6 |
| 127 | 24.6 | 5.2 | 29.8 | 16.0 | 8.4 | 45.7 |
| 172 | 22.5 | 1.9 | 31.4 | 14.4 | 5.2 | 45.8 |
| 43 | 26.8 | 6.6 | 33.4 | 12.5 | 0.9 | 45.9 |
| 68 | 23.6 | 7.1 | 30.7 | 15.3 | 15.7 | 46.0 |
| 150 | 24.5 | 6.2 | 30.7 | 15.3 | 9.6 | 46.0 |
| 451 | 21.9 | 2.7 | 24.6 | 21.4 | 4.5 | 46.0 |
| 541 | 26.9 | 6.8 | 33.7 | 12.5 | 5.1 | 46.1 |
| 312 | 15.3 | 7.3 | 22.6 | 23.6 | 5.3 | 46.1 |
| 110 | 24.9 | 3.9 | 28.8 | 17.3 | 10.7 | 46.1 |
| 548 | 28.7 | 7.4 | 26.2 | 10.1 | 6.4 | 46.3 |
| 530 | 29.0 | 7.3 | 36.3 | 10.1 | 5.3 | 465 |
| 66 | 24.6 | 7.0 | 31.7 | 14.8 | 9.8 | 46.5 |
| 157 | 27.0 | 5.7 | 32.8 | 13.8 | 9.3 | 46.5 |
| 226 | 31.2 | 7.2 | 38.4 | 8.1 | 4.9 | 46.5 |
| 343 | 22.9 | 8.2 | 31.0 | 15.6 | 6.9 | 46.7 |

TABLE 11A-continued

Flavor

| Sample number | hexanal (pg/g) | Hexanal (pg/g) | Hexanol + (pg/g) | 2,4 decadienal | 1-octen-3-ol (MS'S) | 2,4 decadienal + hexanal + hexanol (µg/g) |
|---|---|---|---|---|---|---|
| 152 | 25.8 | 5.1 | 30.9 | 15.8 | 11.2 | 46.7 |
| 164 | 25.0 | 6.6 | 31.6 | 15.2 | 9.3 | 46.8 |
| 374 | 25.1 | 4.0 | 29.1 | 17.7 | 3.0 | 46.8 |
| 336 | 26.9 | 6.3 | 33.2 | 13.6 | 4.6 | 46.8 |
| 171 | 21.0 | 13.0 | 34.0 | 12.9 | 4.9 | 46.9 |
| 567 | 31.9 | 9.6 | 41.5 | 5.4 | 3.5 | 46.9 |
| 90 | 26.8 | 6.1 | 32.8 | 14.1 | 8.2 | 46.9 |
| 350 | 21.1 | 9.2 | 30.3 | 16.6 | 8.0 | 47.0 |
| 131 | 26.9 | 5.4 | 32.3 | 14.7 | 7.0 | 47.0 |
| 345 | 21.9 | 8.3 | 30.2 | 16.9 | 6.3 | 47.1 |
| 436 | 22.3 | 6.5 | 28.8 | 18.3 | 6.3 | 47.1 |
| 309 | 24.6 | 7.6 | 32.2 | 14.8 | 2.8 | 47.1 |
| 181-2 | 23.1 | 5.9 | 28.9 | 18.2 | 8.7 | 47.1 |
| 81 | 28.3 | 5.0 | 33.3 | 13.9 | 4.7 | 47.2 |
| 196 | 22.6 | 5.1 | 27.7 | 19.5 | 6.6 | 47.2 |
| 154 | 27.5 | 5.3 | 32.8 | 14.5 | 7.4 | 47.3 |
| 70 | 25.5 | 5.6 | 31.1 | 16.3 | 8.9 | 47.4 |
| 119 | 28.7 | 3.8 | 32.6 | 14.9 | 4.9 | 47.5 |
| 419 | 13.4 | 8.8 | 22.2 | 25.3 | 1.6 | 47.5 |
| 195 | 19.9 | 6.0 | 25.9 | 21.7 | 5.0 | 475 |
| 396 | 25.6 | 5.6 | 31.3 | 16.3 | 5.7 | 47.5 |
| 109 | 26.1 | 5.4 | 31.5 | 16.1 | 7.1 | 47.5 |
| 347-2 | 25.4 | 7.8 | 33.1 | 14.6 | 5.6 | 47.7 |
| 529 | 24.2 | 7.5 | 31.7 | 16.1 | 5.5 | 47.8 |
| 50 | 28.3 | 7.5 | 35.8 | 12.2 | 6.7 | 48.0 |
| 304 | 22.5 | 6.4 | 29.0 | 19.1 | 1.6 | 48.0 |
| 78 | 26.3 | 6.7 | 33.1 | 15.1 | 6.2 | 48.1 |
| 121-2 | 25.7 | 5.7 | 31.4 | 16.7 | 14.8 | 48.2 |
| 62-2 | 27.1 | 5.9 | 32.9 | 15.2 | 14.0 | 48.2 |
| 553 | 25.7 | 9.7 | 35.4 | 12.9 | 3.2 | 48.3 |
| 511 | 26.3 | 2.7 | 29.1 | 19.2 | 3.8 | 48.3 |
| 413 | 19.2 | 8.8 | 28.0 | 20.4 | 5.8 | 48.4 |
| 106 | 25.9 | 4.2 | 30.1 | 18.3 | 12.8 | 48.4 |
| 303 | 22.9 | 5.4 | 28.3 | 20.2 | 1.9 | 48.5 |
| 182 | 24.1 | 5.5 | 29.6 | 18.9 | 4.5 | 48.5 |
| 12 | 22.6 | 5.9 | 28.5 | 20.1 | 4.5 | 48.5 |
| 176 | 22.7 | 5.6 | 28.3 | 20.3 | 5.2 | 48.6 |
| 265 | 27.8 | 7.2 | 35.0 | 13.7 | 0.9 | 48.7 |
| 264 | 26.5 | 8.0 | 34.5 | 14.3 | 1.8 | 48.8 |
| 344 | 23.6 | 8.0 | 31.6 | 17.3 | 4.4 | 48.8 |
| 85 | 21.4 | 11.4 | 32.8 | 16.1 | 5.1 | 48.9 |
| 394 | 24.5 | 6.2 | 30.7 | 18.2 | 8.4 | 49.0 |
| 268 | 27.8 | 8.5 | 36.3 | 12.8 | 1.3 | 49.1 |
| 535 | 36.1 | 7.2 | 43.3 | 5.8 | 5.1 | 49.1 |
| 194 | 21.8 | 5.9 | 27.7 | 21.5 | 8.3 | 49.2 |
| 443 | 21.7 | 6.8 | 28.5 | 20.9 | 0.8 | 49.4 |
| 340 | 23.7 | 8.1 | 31.8 | 17.6 | 4.7 | 49.4 |
| 129 | 26.6 | 5.3 | 32.0 | 17.5 | 12.9 | 49.4 |
| 152-2 | 27.8 | 5.2 | 33.0 | 16.6 | 11.2 | 49.5 |
| 128 | 27.0 | 4.6 | 31.5 | 18.0 | 15.3 | 49.5 |
| 564 | 27.6 | 7.5 | 35.1 | 14.5 | 3.4 | 49.6 |
| 337 | 29.8 | 6.2 | 36.0 | 13.7 | 3.3 | 49.6 |
| 159 | 28.6 | 5.4 | 34.0 | 15.7 | 15.2 | 49.7 |
| 105 | 25.7 | 6.0 | 31.7 | 18.1 | 15.9 | 49.8 |
| 311 | 25.6 | 6.1 | 31.7 | 18.1 | 6.2 | 49.9 |
| 302 | 23.0 | 6.0 | 28.9 | 21.0 | 7.1 | 49.9 |
| 346-2 | 28.0 | 6.7 | 34.7 | 15.2 | 3.3 | 49.9 |
| 62 | 27.0 | 6.0 | 33.0 | 17.0 | 9.7 | 49.9 |
| 44 | 28.3 | 7.3 | 35.5 | 14.5 | 2.9 | 50.0 |
| 421 | 27.2 | 7.7 | 34.9 | 15.3 | 5.5 | 50.2 |
| 238 | 25.1 | 6.3 | 31.4 | 18.9 | 3.9 | 50.2 |
| 158 | 28.0 | 5.5 | 33.5 | 16.8 | 10.6 | 50.3 |
| 338 | 28.4 | 1.5 | 35.9 | 14.5 | 3.1 | 50.4 |
| 92 | 28.1 | 6.1 | 34.2 | 16.3 | 8.2 | 50.5 |
| 356 | 26.7 | 7.6 | 34.2 | 16.5 | 7.0 | 50.7 |
| 80 | 28.0 | 6.7 | 34.8 | 16.1 | 8.3 | 50.9 |
| 568 | 31.3 | 10.5 | 41.7 | 9.1 | 7.4 | 50.9 |
| 456 | 25.1 | 0.6 | 25.8 | 25.1 | 90.1 | 50.9 |
| 409 | 27.5 | 7.6 | 35.1 | 15.8 | 7.7 | 50.9 |
| 452 | 26.4 | 1.1 | 27.6 | 23.4 | 20.4 | 51.0 |
| 331 | 24.2 | 8.1 | 32.3 | 18.7 | 5.6 | 51.1 |
| 65 | 27.8 | 7.8 | 35.6 | 15.8 | 9.0 | 51.4 |
| 193 | 29.3 | 6.9 | 26.2 | 15.3 | 5.2 | 51.5 |
| 365 | 26.9 | 4.0 | 30.9 | 20.6 | 4.3 | 51.5 |

TABLE 11A-continued

Flavor

| Sample number | hexanal (pg/g) | Hexanal (pg/g) | Hexanol + (pg/g) | 2,4 decadienal | 1-octen-3-ol (MS'S) | 2,4 decadienal + hexanal + hexanol (µg/g) |
|---|---|---|---|---|---|---|
| 462 | 21.9 | 0.6 | 28.5 | 23.2 | 95.0 | 51.7 |
| 204 | 23.7 | 5.9 | 29.6 | 22.2 | 6.2 | 51.8 |
| 115 | 31.1 | 6.2 | 37.3 | 14.7 | 3.7 | 52.0 |
| 441 | 23.4 | 7.6 | 31.0 | 21.0 | 5.8 | 52.0 |
| 307 | 26.5 | 6.3 | 32.9 | 19.2 | 5.5 | 52.1 |
| 391-2 | 26.5 | 5.6 | 32.1 | 20.1 | 7.6 | 52.2 |
| 63 | 28.1 | 6.2 | 34.4 | 17.8 | 14.5 | 52.2 |
| 543 | 35.8 | 8.4 | 44.1 | 8.1 | 3.6 | 52.2 |
| 46 | 31.5 | 6.2 | 37.7 | 14.5 | 4.9 | 52.2 |
| 133 | 29.9 | 5.1 | 35.0 | 17.2 | 10.1 | 52.2 |
| 302-2 | 24.6 | 6.4 | 31.0 | 21.2 | 7.3 | 52.3 |
| 243 | 30.2 | 7.6 | 37.9 | 14.5 | 7.5 | 52.3 |
| 170 | 26.5 | 8.1 | 34.6 | 17.8 | 11.8 | 52.4 |
| 25 | 28.6 | 5.9 | 34.5 | 17.9 | 6.8 | 52.4 |
| 450 | 32.6 | 7.8 | 40.4 | 12.2 | 5.9 | 52.6 |
| 239 | 29.4 | 7.4 | 36.8 | 15.9 | 4.7 | 52.7 |
| 448 | 24.1 | 13.4 | 37.4 | 15.3 | 2.2 | 52.7 |
| 519 | 32.6 | 5.1 | 37.8 | 14.9 | 2.6 | 52.7 |
| 438 | 26.3 | 6.6 | 32.9 | 19.9 | 9.0 | 52.8 |
| 111 | 31.0 | 6.1 | 37.7 | 15.2 | 5.5 | 52.9 |
| 71 | 29.8 | 6.1 | 35.9 | 17.2 | 12.7 | 53.1 |
| 163 | 29.0 | 5.8 | 34.8 | 18.5 | 154 | 53.3 |
| 464 | 26.7 | 0.8 | 27.5 | 25.8 | 35.5 | 53.3 |
| 107 | 29.9 | 4.7 | 34.6 | 18.7 | 20.6 | 53.3 |
| 371 | 28.8 | 4.1 | 32.9 | 20.4 | 8.6 | 53.3 |
| 313 | 25.3 | 6.2 | 32.1 | 21.3 | 9.7 | 53.3 |
| 199 | 23.3 | 5.3 | 28.6 | 24.8 | 6.3 | 53.4 |
| 104 | 25.7 | 6.9 | 32.5 | 20.9 | 17.9 | 53.5 |
| 103 | 29.1 | 3.8 | 32.9 | 20.6 | 13.4 | 53.5 |
| 339 | 25.7 | 9.1 | 34.8 | 18.7 | 4.8 | 53.5 |
| 439 | 27.2 | 6.2 | 33.9 | 19.6 | 6.5 | 53.6 |
| 372 | 27.5 | 3.8 | 31.4 | 22.4 | 6.4 | 53.8 |
| 187 | 15.0 | 22.2 | 37.2 | 16.6 | 2.1 | 53.8 |
| 317 | 26.8 | 5.9 | 32.7 | 21.1 | 7.6 | 53.8 |
| 306 | 23.7 | 6.6 | 30.3 | 23.5 | 8.0 | 53.9 |
| 355 | 30.9 | 7.2 | 38.1 | 15.8 | 4.4 | 53.9 |
| 86 | 30.8 | 6.3 | 37.1 | 16.8 | 11.7 | 53.9 |
| 436-2 | 26.5 | 6.3 | 32..8 | 21.3 | 6.2 | 54.0 |
| 91 | 31.0 | 6.4 | 37.4 | 16.7 | 9.0 | 54.1 |
| 61-2 | 28.1 | 7.8 | 35.9 | 18.2 | 15.4 | 54.1 |
| 77 | 29.7 | 7.0 | 36.7 | 17.5 | 3.3 | 54.2 |
| 156 | 31.5 | 5.4 | 36.9 | 17.3 | 5.9 | 54.2 |
| 511-2 | 27.9 | 2.8 | 30.7 | 23.8 | 5.0 | 54.5 |
| 28 | 34.7 | 6.0 | 40.7 | 13.8 | 7.9 | 54.5 |
| 113 | 32.2 | 5.6 | 37..8 | 16.8 | 15.7 | 54.6 |
| 76 | 30.7 | 6.5 | 37.2 | 17.4 | 9.1 | 54.6 |
| 427 | 32.8 | 7.1 | 39.9 | 14.8 | 5.0 | 54.7 |
| 449 | 26.7 | 7.3 | 34.0 | 20.9 | 4.7 | 54.9 |
| 324 | 26.6 | 8.1 | 34.7 | 20.5 | 0.9 | 55.2 |
| 207 | 36.2 | 8.7 | 44.9 | 10.4 | 0.2 | 55.3 |
| 316 | 29.0 | 6.1 | 35.2 | 20.2 | 6.8 | 55.4 |
| 121 | 29.2 | 5.5 | 34.7 | 20.6 | 11.0 | 55.4 |
| 28 | 32.6 | 6.3 | 38.9 | 16.5 |  | 55.4 |
| 126 | 30.0 | 5.6 | 35.6 | 19.9 | 11.5 | 55.5 |
| 451-2 | 27.2 | 0.8 | 28.0 | 27.6 | 7.8 | 55.6 |
| 135 | 30.1 | 6.0 | 36.1 | 19.7 | 15.3 | 55.8 |
| 393 | 27.9 | 6.5 | 34.5 | 21.4 | 9.2 | 55.8 |
| 130 | 30.2 | 6.1 | 36.3 | 19.6 | 14.2 | 55.9 |
| 357 | 24.3 | 18.1 | 42.4 | 13.5 | 4.1 | 55.9 |
| 314 | 26.0 | 6.7 | 32.6 | 23.3 | 8.3 | 55.9 |
| 184 | 29.0 | 5.5 | 34.5 | 21.5 | 92 | 56.0 |
| 151-2 | 32.5 | 5.6 | 38.2 | 17.9 | 14.5 | 56.1 |
| 101 | 31.5 | 4.0 | 35.5 | 20.6 | 9.0 | 56.1 |
| 331-2 | 27.6 | 7.8 | 35.5 | 20.6 | 5.0 | 56.1 |
| 330 | 30.9 | 8.6 | 39.5 | 16.6 | 7.1 | 56.1 |
| 325 | 28.7 | 9.7 | 38.4 | 17.8 | 5.6 | 56.2 |
| 351 | 27.7 | 6.7 | 34.3 | 21.9 | 4.8 | 56.2 |
| 403 | 39.1 | 8.1 | 47.1 | 9.1 | 6.3 | 56.2 |
| 322 | 29.8 | 8.1 | 37..8 | 18.6 | 4.6 | 56.5 |
| 463 | 26.8 | 0.7 | 27.5 | 28.9 | 36.7 | 56.5 |
| 155 | 32.7 | 5.7 | 38.4 | 18.1 | 6.3 | 56.5 |
| 435 | 32.0 | 7.4 | 39.5 | 17.2 | 4.2 | 56.6 |
| 397 | 28.8 | 6.4 | 35.2 | 21.6 | 4.3 | 56.8 |
|  | 29.2 | 7.0 | 36.3 | 20.6 | 10.4 | 56.9 |

TABLE 11A-continued

Flavor

| Sample number | hexanal (pg/g) | Hexanal (pg/g) | Hexanol + (pg/g) | 2,4 decadienal | 1-octen-3-ol (MS'S) | 2,4 decadienal + hexanal + hexanol (μg/g) |
|---|---|---|---|---|---|---|
| 465 | 26.5 | 1.0 | 27.5 | 29.5 | 44.8 | 56.9 |
| 183 | 29.4 | 8.1 | 37.5 | 19.5 | 12 | 57.0 |
| 321 | 35.0 | 9.4 | 44.4 | 12.9 | 4.0 | 57.3 |
| 457 | 31.2 | 0.7 | 31.8 | 25.5 | 15.4 | 57.4 |
| 21 | 32.9 | 6.3 | 39.2 | 18.2 | 2.4 | 57.4 |
| 316-2 | 28.5 | 6.1 | 34.6 | 22.9 | 7.9 | 57.5 |
| 34 | 33.6 | 7.1 | 40.7 | 16.9 | 9.4 | 57.6 |
| 69 | 30.5 | 6.9 | 37.4 | 20.2 | 11.4 | 57.6 |
| 94 | 31.9 | 8.3 | 40.2 | 17.4 | 8.3 | 57.6 |
| 317-2 | 28.3 | 6.0 | 34.3 | 23.5 | 8.8 | 57.8 |
| 422 | 25.9 | 10.0 | 35.9 | 22.0 | 6.2 | 57.9 |
| 366 | 35.1 | 4.3 | 39.4 | 18.5 | 6.5 | 51.9 |
| 188 | 28.9 | 9.4 | 38.3 | 19.7 | 9.2 | 58.0 |
| 87 | 32.2 | 7.3 | 39.5 | 18.5 | 7.3 | 58.0 |
| 473 | 27.8 | 4.6 | 32.4 | 25.6 | 10.7 | 58.0 |
| 527 | 31.5 | 6.7 | 38.2 | 19.9 | 4.1 | 58.1 |
| 341 | 28.6 | 7.9 | 36.5 | 21.7 | 3.7 | 58.2 |
| 117 | 33.6 | 6.6 | 40.2 | 18.0 | 8.7 | 58.2 |
| 342 | 28.6 | 1.9 | 36.5 | 21.8 | 4.3 | 58.2 |
| 4 | 28.9 | 1.1 | 36.6 | 21.7 | 11.7 | 58.3 |
| 67 | 31.7 | 7.0 | 38.7 | 19.7 | 12.0 | 58.4 |
| 47 | 34.1 | 6.9 | 41.0 | 17.4 | 3.2 | 58.4 |
| 165 | 33.2 | 6.2 | 39.4 | 19.0 | 12.9 | 58.5 |
| 369 | 30.5 | 4.1 | 34.6 | 24.0 | 12.3 | 58.6 |
| 370 | 38.8 | 4.1 | 42.9 | 15.9 | 4.2 | 58.8 |
| 421-2 | 29.1 | 7.8 | 37.0 | 21.9 | 5.3 | 58.9 |
| 533 | 31.1 | 7.4 | 38.5 | 20.7 | 5.7 | 59.2 |
| 35 | 34.1 | 6.3 | 40.4 | 18.8 | 6.4 | 59.2 |
| 434 | 22.0 | 10.2 | 32.2 | 27.0 | 8.6 | 59.2 |
| 364 | 30.8 | 3.9 | 34.7 | 24.5 | 4.6 | 59.2 |
| 326 | 27.0 | 8.7 | 35.7 | 23.6 | 2.9 | 59.3 |
| 123 | 32.0 | 5.9 | 37.8 | 21.5 | 11.4 | 59.4 |
| 120 | 33.2 | 4.0 | 37.2 | 22.2 | 20.2 | 59.4 |
| 116 | 34.5 | 6.2 | 40.8 | 18.7 | 8.7 | 59.4 |
| 361 | 33.1 | 4.1 | 37.2 | 22.3 | 2.3 | 59.5 |
| 84 | 34.8 | 6.3 | 41.1 | 18.8 | 1.5 | 59.9 |
| 24 | 31.1 | 5.7 | 36.8 | 23.1 | 3.4 | 59.9 |
| 353 | 30.5 | 8.8 | 39.3 | 20.6 | 5.9 | 60.0 |
| 122-2 | 32.7 | 5.7 | 38.4 | 21.6 | 17.5 | 60.1 |
| 528 | 32.7 | 6.6 | 39.3 | 20.9 | 5.3 | 60.2 |
| 186 | 35.3 | 8.2 | 43.5 | 16.7 | 6.2 | 60.2 |
| 21-2 | 32.6 | 6.2 | 38.8 | 21.4 | 3.2 | 60.2 |
| 415 | 26.9 | 7.0 | 33.9 | 26.4 | 5.8 | 60.3 |
| 328 | 26.5 | 8.1 | 34.6 | 25.8 | 5.9 | 60.4 |
| 118 | 36.0 | 3.9 | 39.9 | 20.5 | 7.1 | 60.4 |
| 402 | 32.8 | 6.5 | 39.4 | 21.2 | 4.6 | 60.5 |
| 466 | 31.8 | 1.0 | 32.8 | 27.9 | 38.5 | 60.7 |
| 13 | 31.8 | 6.6 | 38.4 | 22.4 | 8.2 | 60.8 |
| 442 | 27.1 | 12.1 | 39.2 | 21.8 | 2.6 | 60.9 |
| 61 | 32.9 | 8.1 | 41.0 | 20.3 | 15.7 | 61.3 |
| 455 | 28.4 | 0.8 | 29.2 | 32.1 | 30.6 | 61.3 |
| 423 | 29.2 | 6.1 | 35.3 | 26.1 | 3.8 | 61.4 |
| 169 | 36.0 | 8.5 | 44.5 | 17.0 | 7.8 | 61.4 |
| 458 | 27.8 | 2.2 | 30.0 | 31.6 | 5.4 | 61.5 |
| 362 | 35.8 | 3.9 | 39.7 | 22.1 | 5.2 | 61.8 |
| 124 | 33.6 | 5.9 | 39.5 | 22.4 | 11.9 | 61.9 |
| 33 | 35.7 | 6.4 | 42.1 | 19.9 | 7.2 | 62.0 |
| 22-2 | 32.7 | 6.0 | 38.6 | 23.3 | 6.2 | 62.0 |
| 23 | 36.2 | 6.7 | 42.9 | 19.2 | 2.3 | 62.1 |
| 32 | 34.0 | 6.5 | 40.5 | 21.8 | 9.7 | 62.3 |
| 253 | 36.1 | 11.2 | 47.3 | 15.0 | 1.7 | 62.3 |
| 75 | 36.9 | 6.1 | 43.0 | 19.5 | 8.2 | 62.5 |
| 318 | 28.4 | 9.2 | 37.6 | 25.0 | 4.7 | 62.6 |
| 420 | 26.8 | 11.3 | 38.1 | 24.5 | 7.8 | 62.6 |
| 161 | 34.0 | 6.1 | 40.1 | 22.6 | 8.2 | 62.7 |
| 74 | 34.3 | 7.4 | 41.7 | 21.1 | 12.2 | 62.8 |
| 48 | 39.0 | 6.4 | 45.4 | 17.5 | 2.5 | 62.9 |
| 26 | 33.8 | 6.7 | 40.5 | 22.6 | 5.7 | 63.1 |
| 406-2 | 32.4 | 9.1 | 41.5 | 21.7 | 7.4 | 63.2 |
| 552 | 42.2 | 7.8 | 50.0 | 13.9 | 4.1 | 63.9 |
| 51-2 | 37.5 | 6.5 | 44.1 | 19.8 | 4.0 | 63.9 |
| 424 | 31.4 | 1.6 | 39.1 | 24.9 | 7.6 | 63.9 |
| 88 | 37.9 | 6.1 | 44.6 | 19.4 | 8.3 | 63.9 |
| 122 | 34.9 | 62 | 41.2 | 23.0 | 13.0 | 64.2 |

TABLE 11A-continued

| | | | Flavor | | |
|---|---|---|---|---|---|
| Sample number | hexanal (pg/g) | Hexanal (pg/g) | Hexanol + (pg/g) | 2,4 decadienal | 1-octen-3-ol (MS'S) | 2,4 decadienal + hexanal + hexanol (µg/g) |
| 160 | 36.7 | 6.1 | 42.9 | 21.5 | 11.8 | 64.4 |
| 398 | 36.1 | 8.0 | 44.1 | 20.4 | 15.7 | 64.4 |
| 89 | 36.6 | 8.5 | 45.0 | 19.9 | 11.4 | 64.9 |
| 323 | 34.5 | 7.3 | 41.8 | 23.2 | 0.9 | 65.0 |
| 512 | 32.0 | 3.1 | 35.1 | 29.9 | 11.8 | 65.0 |
| 429 | 30.6 | 7.3 | 37.9 | 27.3 | 113 | 65.2 |
| 91-2 | 37.1 | 6.7 | 43.7 | 21.6 | 8.6 | 65.3 |
| 64 | 38.9 | 11.8 | 50.7 | 14.7 | 9.6 | 65.4 |
| 433 | 32.4 | 8.5 | 40.9 | 24.5 | 2.3 | 65.4 |
| 453 | 31.1 | 0.8 | 31.9 | 33.6 | 41.5 | 65.5 |
| 367 | 36.2 | 4.0 | 40.3 | 25.4 | 4.7 | 65.7 |
| 10 | 35.6 | 9.3 | 44.9 | 21.7 | 2.1 | 66.5 |
| 437-2 | 33.9 | 8.2 | 42.1 | 24.5 | 3.4 | 66.6 |
| 521 | 35.1 | 3.6 | 38.7 | 27.9 | 7.8 | 66.6 |
| 472 | 33.4 | 2.7 | 36.1 | 30.6 | 6.6 | 66.8 |
| 56 | 40.7 | 9.8 | 50.6 | 16.3 | 15.2 | 66.8 |
| 5 | 36.1 | 6.0 | 42.1 | 24.8 | 3.2 | 66.9 |
| 31 | 41.3 | 6.3 | 47.5 | 19.7 | 7.5 | 67.3 |
| 532 | 48.9 | 8.9 | 57.8 | 10.1 | 5.6 | 67.9 |
| 329 | 34.9 | 9.1 | 44.1 | 24.0 | 5.1 | 68.1 |
| 134 | 38.9 | 5.3 | 44.2 | 24.0 | 14.9 | 68.2 |
| 2 | 34.0 | 11.2 | 45.2 | 23.0 | 7.9 | 68.3 |
| 526 | 45.9 | 7.1 | 53.0 | 15.7 | 2.7 | 68.8 |
| 408 | 36.3 | 7.8 | 44.2 | 24.6 | 8.2 | 68.8 |
| 523 | 35.9 | 5.4 | 41.3 | 27.7 | 7.4 | 69.1 |
| 373 | 42.4 | 4.0 | 46.4 | 22.7 | 6.0 | 69.1 |
| 407-2 | 37.7 | 6.8 | 44.5 | 24.8 | 7.6 | 69.3 |
| 79 | 37.9 | 7.9 | 45.8 | 23.7 | 7.7 | 69.4 |
| 524 | 44.3 | 3.9 | 48.2 | 21.3 | 7.6 | 69.5 |
| 478 | 34.1 | 7.0 | 41.1 | 28.4 | 3.9 | 69.5 |
| 515 | 36.4 | 4.7 | 41.2 | 28.5 | 8.0 | 69.6 |
| 476 | 33.1 | 3.3 | 36.4 | 33.3 | 6.2 | 69.7 |
| 8 | 37.5 | 9.1 | 46.6 | 23.1 | 6.9 | 69.8 |
| 516 | 35.7 | 3.6 | 39.2 | 30.6 | 8.3 | 69.9 |
| 520 | 38.5 | 5.5 | 44.0 | 26.1 | 8.7 | 70.2 |
| 503 | 39.1 | 3.4 | 42.5 | 27.8 | 6.8 | 70.3 |
| 406 | 38.7 | 6.8 | 45.5 | 24.9 | 9.7 | 70.5 |
| 363 | 36.4 | 3.9 | 40.3 | 30.3 | 6.9 | 70.6 |
| 49 | 47.0 | 8.5 | 55.5 | 15.1 | 3.0 | 70.7 |
| 98 | 39.4 | 7.5 | 46.8 | 23.9 | 11.9 | 70.8 |
| 414 | 32.0 | 12.2 | 44.2 | 26.7 | 3.9 | 70.9 |
| 308 | 30.9 | 6.9 | 37.8 | 33.3 | 3.8 | 71.1 |
| 514 | 36.9 | 3.9 | 40.8 | 30.4 | 4.8 | 71.2 |
| 509 | 39.7 | 5.0 | 44.7 | 26.8 | 7.3 | 71.4 |
| 234 | 39.1 | 10.2 | 49.3 | 22.4 | 3.8 | 71.7 |
| 466-2 | 32.5 | 1.9 | 40.4 | 31.5 | 36.6 | 71.9 |
| 101-2 | 38.7 | 10.5 | 49.2 | 22.9 | 8.1 | 72.1 |
| 162 | 40.2 | 7.7 | 47.9 | 24.6 | 12.0 | 72.5 |
| 361-2 | 40.3 | 3.8 | 44.1 | 28.4 | 3.4 | 72.5 |
| 334 | 39.8 | 10.4 | 50.2 | 22.8 | 3.9 | 73.0 |
| 327 | 35.5 | 12.8 | 48.3 | 24.8 | 2.8 | 73.0 |
| 525 | 38.4 | 8.3 | 46.8 | 26.6 | 7.9 | 73.4 |
| 52 | 48.8 | 6.6 | 55.4 | 18.5 | 4.0 | 73.9 |
| 54 | 43.7 | 10.8 | 54.5 | 19.4 | 16.6 | 73.9 |
| 459 | 35.8 | 3.0 | 38.8 | 35.6 | 4.1 | 74.4 |
| 497 | 39.2 | 4.8 | 44.1 | 30.8 | 6.6 | 74.9 |
| 83 | 44.9 | 6.4 | 51.2 | 23.8 | 8.7 | 75.1 |
| 81-2 | 54.4 | 6.3 | 60.7 | 14.3 | 4.1 | 75.1 |
| 467 | 42.8 | 0.9 | 43.7 | 31.4 | 21.8 | 75.1 |
| 526-2 | 46.9 | 6.9 | 53.7 | 21.8 | 4.3 | 75.5 |
| 469 | 36.0 | 5.5 | 41.5 | 34.1 | 6.5 | 75.6 |
| 500 | 33.2 | 5.9 | 39.1 | 37.3 | 7.2 | 76.3 |
| 73 | 44.6 | 7.3 | 51.9 | 24.6 | 9.8 | 76.6 |
| 100 | 43.1 | 9.3 | 52.4 | 24.2 | 6.4 | 76.6 |
| 518 | 40.0 | 4.3 | 44.3 | 32.4 | 5.4 | 76.7 |
| 437 | 28.3 | 15.4 | 43.7 | 33.1 | 4.9 | 76.8 |
| 58 | 42.6 | 15.2 | 57.8 | 19.2 | 16.9 | 77.1 |
| 19 | 44.7 | 7.3 | 52.0 | 25.1 | 12.7 | 77.1 |
| 467-2 | 45.3 | 1.8 | 47.1 | 30.1 | 3.8 | 77.2 |
| 508 | 48.0 | 4.9 | 52.9 | 24.3 | 8.7 | 77.2 |
| 454 | 37.7 | 1.2 | 38.9 | 38.4 | 8.3 | 77.2 |
| 499 | 41.0 | 5.0 | 46.0 | 31.7 | 7.0 | 77.7 |
| 333 | 44.0 | 8.7 | 52.7 | 25.1 | 4.5 | 77.8 |
| 431 | 40.1 | 7.0 | 47.1 | 30.8 | 8.3 | 77.9 |

TABLE 11A-continued

| | | | Flavor | | |
|---|---|---|---|---|---|
| Sample number | hexanal (pg/g) | Hexanal (pg/g) | Hexanol + (pg/g) | 2,4 decadienal | 1-octen-3-ol (MS'S) | 2,4 decadienal + hexanal + hexanol (μg/g) |
| 167 | 54.4 | 6.9 | 61.2 | 16.8 | 9.5 | 78.0 |
| 480 | 41.3 | 5.5 | 46.8 | 31.3 | 5.9 | 78.1 |
| 6 | 46.4 | 9.1 | 55.5 | 22.7 | 11.9 | 78.2 |
| 501 | 48.8 | 7.3 | 56.1 | 22.3 | 8.4 | 78.4 |
| 410 | 48.2 | 9.0 | 57.2 | 21.6 | 3.7 | 78.7 |
| 471 | 38.8 | 3.9 | 42.7 | 36.1 | 7.2 | 78.8 |
| 468 | 38.7 | 5.6 | 44.3 | 34.9 | 7.4 | 79.1 |
| 475 | 36.7 | 6.3 | 43.0 | 36.1 | 6.5 | 79.1 |
| 470 | 36.7 | 7.4 | 44.1 | 35.2 | 6.5 | 79.3 |
| 502 | 39.4 | 3.9 | 43.3 | 36.1 | 12.5 | 79.3 |
| 477 | 43.2 | 2.9 | 46.1 | 33.6 | 5.9 | 79.7 |
| 479 | 41.0 | 6.5 | 47.5 | 32.9 | 6.2 | 80.4 |
| 368 | 46.8 | 4.0 | 50.8 | 29.6 | 8.6 | 80.4 |
| 60 | 49.0 | 4.0 | 53.0 | 27.7 | 13.7 | 80.6 |
| 166-2 | 49.7 | 8.1 | 57.8 | 23.2 | 3.8 | 81.0 |
| 412 | 47.3 | 8.4 | 55.8 | 25.3 | 6.9 | 81.1 |
| 93 | 52.5 | 4.2 | 56.8 | 26.5 | 6.4 | 83.2 |
| 510 | 42.4 | 6.0 | 48.4 | 35.3 | 7.5 | 83.7 |
| 474 | 41.4 | 5.8 | 47.2 | 37.2 | 10.8 | 84.4 |
| 53 | 55.2 | 6.5 | 61.7 | 24.3 | 7.6 | 86.0 |
| 99 | 51.5 | 8.1 | 59.6 | 26.5 | 10.1 | 86.0 |
| 537 | 68.9 | 8.9 | 77.8 | 8.4 | 4.0 | 86.2 |
| 522 | 45.2 | 6.1 | 51.3 | 35.6 | 7.9 | 86.9 |
| 11.2 | 53.2 | 15.8 | 69.0 | 18.1 | 3.5 | 87.1 |
| 55 | 56.0 | 9.8 | 65.8 | 21.5 | 11.4 | 87.3 |
| 504 | 43.5 | 5.2 | 48.7 | 38.8 | 8.2 | 87.5 |
| 320 | 51.0 | 12.2 | 63.2 | 24.6 | 5.8 | 87.7 |
| 319 | 51.6 | 10.6 | 62.2 | 26.5 | 4.8 | 88.7 |
| 506 | 55.0 | 5.1 | 60.1 | 28.9 | 6.0 | 88.9 |
| 95 | 54.3 | 7.5 | 61.8 | 27.9 | 7.9 | 89.7 |
| 30 | 57.4 | 6.6 | 64.0 | 25.9 | 8.2 | 89.9 |
| 517 | 59.1 | 5.4 | 64.5 | 25.7 | 10.5 | 90.3 |
| 96 | 53.5 | 7.9 | 61.4 | 28.9 | 9.6 | 90.3 |
| 29 | 61.2 | 7.1 | 68.3 | 26.1 | 3.8 | 94.4 |
| 496 | 60.6 | 5.2 | 65.9 | 29.6 | 4.5 | 95.5 |
| 512-2 | 53.4 | 3.5 | 56.9 | 38.6 | 13.7 | 95.5 |
| 59 | 55.8 | 9.5 | 65.3 | 30.5 | 14.1 | 95.9 |
| 7 | 56.6 | 11.3 | 67.9 | 28.7 | 8.5 | 96.6 |
| 16 | 60.4 | 11.6 | 72.1 | 29.3 | 11.8 | 101.4 |
| 20 | 67.2 | 8.1 | 75.3 | 26.8 | 9.9 | 102.1 |
| 513 | 64.3 | 4.1 | 68.4 | 37.2 | 10.8 | 105.6 |
| 498 | 60.3 | 4.8 | 65.1 | 41.4 | 10.3 | 106.5 |
| 9 | 67.4 | 8.4 | 75.8 | 32.1 | 9.1 | 107.9 |
| 14 | 65.8 | 7.4 | 73.2 | 35.8 | 7.8 | 109.0 |
| 496-2 | 79.1 | 6.0 | 85.2 | 28.4 | 4.5 | 113.5 |
| 507 | 78.1 | 6.2 | 84.3 | 29.5 | 6.5 | 113.8 |
| 97 | 69.2 | 10.8 | 80.0 | 34.9 | 11.2 | 114.9 |
| 430 | 76.1 | 14.0 | 90.1 | 25.1 | 3.7 | 115.2 |
| 12 | 74.1 | 11.5 | 85.6 | 30.6 | 2.9 | 116.2 |
| 505 | 83.3 | 6.5 | 89.8 | 29.9 | 7.8 | 119.6 |
| 18 | 77.1 | 6.7 | 83.8 | 36.0 | 7.6 | 119.8 |
| 17 | 81.7 | 8.2 | 89.8 | 36.6 | 10.1 | 126.5 |
| 392 | 92.1 | 14.7 | 106.8 | 20.5 | 15.0 | 127.4 |
| 425 | 90.2 | 12.7 | 102.9 | 28.8 | 8.2 | 131.7 |
| 60 | 86.9 | 8.3 | 95.2 | 41.3 | 25.8 | 136.5 |
| 426 | 119.6 | 15.4 | 135.0 | 24.1 | 4.19.0 | 159.1 |
| 82 | 119.9 | 50.5 | 170.4 | 13.9 | | 184.4 |
| Range | 4.9-120 | 0.6-51 | 7.0-170 | 2.8-41 | 0-95 | 21-184 |
| Average | 28.5 | 6.6 | 35.0 | 17.4 | 7.3 | 52.4 |
| Stdev | 13.9 | 2.9 | 15.1 | 7.8 | 7.0 | 20.1 |

TABLE 11B

| Color | | |
|---|---|---|
| Sample Name | b* | L* |
| ID:47 | 27.18 | 82.34 |
| ID:42 | 27.29 | 83.02 |
| ID:45 | 27.40 | 81.58 |
| JA:48 | 27.88 | 84.41 |
| LB:32 | 28.10 | 83.24 |
| LB:33 | 28.24 | 81.99 |

TABLE 11B-continued

| | Color | |
|---|---|---|
| Sample Name | b* | L* |
| LB:30 | 28.47 | 80.80 |
| JA:45 | 28.62 | 82.83 |
| LB:26 | 28.71 | 82.43 |
| JA:44 | 28.86 | 84.03 |
| ID:34 | 28.94 | 80.43 |
| KA:45 | 29.17 | 84.29 |
| ID:15 | 29.43 | 79.01 |
| ID:48 | 29.56 | 79.52 |
| LB:15 | 29.60 | 82.41 |
| ID:28 | 30.05 | 78.60 |
| KA:44 | 30.83 | 81.90 |
| JB:12 | 31.17 | 78.99 |
| JB:16 | 31.42 | 79.02 |
| KA:25 | 32.69 | 80.71 |
| LB:9 | 32.89 | 79.97 |
| JA:49 | 33.48 | 79.05 |
| JB:14 | 33.80 | 77.60 |
| Range | 27-34 | 77-84 |
| Average | 29.73 | 81:22 |

EXAMPLE 6

Demonstration of the Ability to Combine the Low Odor-Producing Trait with a Low Linolenic Acid Composition Trait This example shows that it is possible to combine the low odor-producing trait with a low linolenic acid composition trait and further explores the effects of dehulling soybeans on the production of odors. The percentage of soybean fatty acids that are linolenic acid is normally about 8%. Using traditional breeding it was possible to create soybeans containing less that 6% linolenic acids and low odor producing property (Table 12).

The formation of 1-octen-3-ol is independent of the formation of other volatile compounds measured in the odor assay. One hypothesis is that fungal enzymes on the surface of the soybeans are the source of the rapid formation of 1-octen-3-ol in the assay. It was reasoned that dehulling the seed before grinding to flour, should decrease the levels of fungal enzymes in the odor assay. Whole soybeans are normally ground to create flour that is used in the odor assay. A retest was performed using six low odor, low linolenic soybean lines that were carefully dehulled. The amount of 1-octen-3-ol formed from the dehulled seeds was about half that of the whole seeds, supporting the hypothesis that components such as fungus and fungal enzymes in the hull portion contribute to 1-octen-3-ol formation (Table 13). Lipoxygenase-null soybeans frequently produce higher levels of 1-octen-3-ol (Table 3). It was reasoned that lipoxygenases may play a role in inhibiting the growth of mold, so in the absence of lipoxygenases, mold infections may be greater allowing more fungal enzymes and formation of 1-octen-3-ol. Low odor soybeans containing lipoxygenases, that were identified by the screen of this invention tend to have a lower 1-octen-3-ol range than that of higher odor soybeans (e.g., Table 12).

Table 12 A1 to A 4: Color and odor-producing properties of low linolenic soybean lines. Color values are L* (lightness), a* (green-red), and b* (blue-yellow).

TABLE 12 A1

| Cross Type | Linolenic acid (%) | Hexanal (μg/g) | Hexanol (μg/g) | 1-octen-3-ol (μg/g) | 2,4 decadienal (μg/g) | 12,4 decadienal, hexanal, hexanol (μg/g) | L* | a* | b* |
|---|---|---|---|---|---|---|---|---|---|
| J-2 | 4.0 | 5.0 | 0.5 | 4.4 | 4.0 | 9.6 | 79.9 | 1.5 | 27.5 |
| J-1 | 3.7 | 7.3 | 0.6 | 5.1 | 4.8 | 12.7 | 82.6 | 0.4 | 27.0 |
| J-3 | 3.5 | 7.6 | 0.7 | 6.3 | 8.6 | 16.8 | 81.9 | 1.0 | 26.8 |
| J-4 | 4.6 | 5.8 | 5.1 | 4.3 | 9.4 | 20.3 | 81.9 | 0.9 | 27.5 |
| J-5 | 4.2 | 6.5 | 5.1 | 4.7 | 8.9 | 20.5 | 81.8 | 0.7 | 26.3 |
| F-2 | 2.7 | 14.8 | 0.4 | 3.9 | 7.6 | 22.7 | 82.6 | 0.6 | 26.2 |
| E-11 | 2.7 | 19.9 | 5.1 | 4.4 | 7.0 | 32.0 | | | |
| G-31 | 4.1 | 20.3 | 1.1 | 5.5 | 11.0 | 32.4 | | | |
| I-7 | 3.1 | 16.0 | 5.1 | 3.5 | 12.2 | 33.3 | | | |
| J-12 | 3.3 | 16.5 | 5.1 | 4.2 | 12.5 | 34.1 | | | |
| I-4 | | 15.5 | 5.5 | 3.6 | 13.7 | 34.3 | | | |
| G-21 | 4.1 | 20.7 | 2.1 | 6.0 | 12.1 | 34.8 | | | |
| F-20 | 4.9 | 24.6 | 1.4 | 3.8 | 9.3 | 35.3 | | | |
| F-3 | 2.8 | 23.3 | 0.9 | 9.1 | 11.7 | 35.9 | | | |
| E-13 | 3.0 | 23.4 | 5.1 | 4.1 | 7.4 | 35.9 | | | |
| G-30 | 3.2 | 21.8 | 1.3 | 5.4 | 13.0 | 36.0 | | | |
| F-6 | | 23.0 | 1.7 | 5.9 | 11.6 | 36.3 | | | |
| G-27 | | 22.6 | 0.9 | 6.6 | 12.9 | 36.4 | | | |
| G-16 | 4.2 | 19.5 | 3.5 | 4.6 | 13.6 | 36.6 | | | |
| G-10 | 4.1 | 17.3 | 3.6 | 3.5 | 16.0 | 36.9 | | | |
| G-15 | 4.4 | 18.9 | 3.0 | 4.8 | 15.4 | 37.2 | | | |
| G-28 | 4.2 | 24.8 | 1.0 | 7.0 | 11.4 | 37.2 | | | |
| H-1 | 3.4 | 17.2 | 5.1 | 3.0 | 15.2 | 37.5 | | | |
| F-17 | 3.9 | 25.7 | 1.3 | 5.3 | 10.5 | 37.5 | | | |
| G-26 | 3.8 | 23.1 | 1.0 | 5.1 | 13.7 | 37.9 | | | |
| E-14 | 3.0 | 20.9 | 5.1 | 5.3 | 11.9 | 37.9 | | | |
| J-16 | 3.2 | 19.8 | 5.1 | 4.5 | 13.0 | 38.0 | | | |
| E-6 | 2.9 | 17.4 | 5.1 | 4.3 | 15.6 | 38.0 | | | |
| E-3 | 2.9 | 17.8 | 5.1 | 3.0 | 15.4 | 38.2 | | | |
| F-10 | 4.3 | 20.1 | 5.1 | 3.0 | 13.0 | 38.3 | | | |
| F-1 | 2.7 | 21.6 | 1.5 | 5.4 | 15.6 | 38.6 | | | |

TABLE 12 A2

| Cross Type | Linolenic acid (%) | Hexanal (μg/g) | Hexanol (μg/g) | 1-octen-3-ol (μg/g) | 2,4 decadienal (μg/g) | 2,4 decadienal, hexanal, hexanol (μg/g) |
|---|---|---|---|---|---|---|
| E-7 | 3.0 | 20.1 | 5.1 | 4.0 | 13.5 | 38.7 |
| E-5 | 2.7 | 20.2 | 5.1 | 4.2 | 13.7 | 38.9 |
| G-8 | 4.2 | 27.1 | 3.5 | 4.1 | 8.3 | 38.9 |
| E-16 | 3.1 | 22.2 | 2.3 | 3.8 | 14.6 | 39.1 |
| F-19 | 3.6 | 26.2 | 5.1 | 3.3 | 7.9 | 39.1 |
| G-19 | 4.3 | 20.0 | 4.2 | 4.6 | 15.2 | 39.4 |
| F-25 | 3.9 | 23.4 | 0.7 | 9.5 | 15.3 | 39.4 |
| F-21 | 2.8 | 22.9 | 1.1 | 7.2 | 15.7 | 39.6 |
| G-11 | 4.2 | 22.1 | 4.0 | 4.6 | 13.6 | 39.7 |
| J-17 | 3.0 | 22.8 | 5.1 | 4.9 | 12.4 | 40.2 |
| E-15 | 3.0 | 19.5 | 5.1 | 5.0 | 15.8 | 40.4 |
| E-4 | 2.8 | 21.1 | 5.1 | 3.2 | 14.5 | 40.6 |
| J-14 | 3.2 | 20.6 | 5.1 | 4.3 | 15.2 | 40.9 |
| G-24 | 4.0 | 22.9 | 1.9 | 7.0 | 16.1 | 40.9 |
| J-13 | 3.2 | 20.9 | 5.1 | 4.1 | 15.0 | 41.0 |
| E-10 | 2.8 | 22.9 | 5.1 | 4.0 | 13.1 | 41.1 |
| F-31 | 3.5 | 26.8 | 0.0 | 9.6 | 14.3 | 41.2 |
| J-34 | 3.2 | 26.2 | 5.1 | 3.5 | 10.1 | 41.3 |
| G-25 | 3.5 | 23.6 | 2.5 | 7.2 | 15.3 | 41.4 |
| F-5 | 2.7 | 25.7 | 1.3 | 9.6 | 14.5 | 41.5 |
| J-30 | 3.2 | 26.5 | 5.1 | 4.8 | 10.0 | 41.5 |
| H-7 | 3.2 | 22.2 | 5.1 | 4.2 | 14.6 | 41.9 |
| G-22 | 4.0 | 22.6 | 1.5 | 7.5 | 17.9 | 42.0 |
| E-11 | 2.9 | 27.6 | 5.1 | 4.1 | 9.4 | 42.1 |
| J-19 | 3.0 | 22.2 | 5.1 | 3.8 | 14.9 | 42.2 |
| F-13 | 4.0 | 30.4 | 1.2 | 4.3 | 10.8 | 42.3 |
| G-23 | 3.2 | 23.6 | 2.2 | 6.2 | 16.6 | 42.4 |
| E-9 | 2.9 | 25.2 | 5.1 | 3.4 | 12.3 | 42.6 |
| F-22 | 3.4 | 25.3 | 1.0 | 8.7 | 16.4 | 42.7 |
| E-8 | 2.9 | 25.2 | 5.1 | 4.1 | 12.7 | 42.9 |
| E-1 | 2.8 | 21.9 | 5.1 | 2.6 | 16.6 | 43.6 |
| F-8 | 3.7 | 26.0 | 5.1 | 3.1 | 12.6 | 43.6 |
| F-32 | 2.8 | 25.6 | 0.9 | 9.1 | 17.4 | 43.8 |
| F-23 | 3.6 | 28.6 | 0.9 | 6.5 | 14.8 | 44.3 |

TABLE 12 A3

| Cross Type | Linolenic acid (%) | Hexanal (μg/g) | Hexanol (μg/g) | 1-octen-3-ol (μg/g) | 2,4 decadienal (μg/g) | 2,4 decadienal, hexanal, hexanol (μg/g) |
|---|---|---|---|---|---|---|
| J-6 | 2.7 | 23.8 | 5.1 | 4.2 | 15.7 | 44.6 |
| G-29 | 4.0 | 23.7 | 1.5 | 6.8 | 19.3 | 44.6 |
| F-7 | 4.1 | 25.4 | 5.1 | 3.8 | 14.1 | 44.6 |
| I-12 | 2.9 | 22.0 | 5.1 | 3.9 | 17.7 | 44.8 |
| G-17 | 4.1 | 20.8 | 4.2 | 4.1 | 20.1 | 45.1 |
| F-4 | 2.8 | 24.0 | 5.1 | 3.6 | 16.2 | 45.3 |
| H-6 | 3.1 | 24.7 | 5.1 | 3.5 | 15.7 | 45.4 |
| G-9 | 4.5 | 23.9 | 3.8 | 3.8 | 17.8 | 45.5 |
| I-11 | 3.1 | 21.2 | 5.1 | 3.6 | 19.2 | 45.5 |
| G-14 | 4.1 | 22.8 | 3.3 | 4.9 | 19.5 | 45.7 |
| I-13 | 2.9 | 21.1 | 5.1 | 4.8 | 19.6 | 45.8 |
| J-15 | 3.1 | 24.4 | 5.1 | 5.6 | 16.8 | 46.3 |
| F-33 | 3.0 | 29.0 | 0.9 | 10.1 | 17.6 | 47.5 |
| E-2 | 2.8 | 25.3 | 5.1 | 3.4 | 17.4 | 47.8 |
| J-32 | 3.0 | 31.5 | 5.1 | 4.6 | 11.2 | 47.8 |
| E-18 | 3.0 | 28.8 | 2.9 | 3.2 | 16.2 | 48.0 |
| H-5 | 3.0 | 30.0 | 5.1 | 3.3 | 13.0 | 48.0 |
| E-17 | 3.2 | 29.0 | 3.2 | 2.5 | 16.3 | 48.6 |
| I-6 | 2.9 | 30.8 | 5.1 | 4.1 | 12.8 | 48.7 |
| J-33 | 2.9 | 28.6 | 5.1 | 2.6 | 15.2 | 48.9 |
| G-2 | 2.9 | 26.8 | 1.5 | 6.5 | 20.7 | 49.0 |
| G-12 | 4.1 | 23.1 | 4.9 | 4.5 | 21.4 | 49.4 |
| I-8 | 2.8 | 26.5 | 5.1 | 5.7 | 18.0 | 49.5 |
| G-5 | 2.9 | 31.1 | 3.4 | 8.1 | 15.2 | 49.7 |

TABLE 12 A3-continued

| Cross Type | Linolenic acid (%) | Hexanal (μg/g) | Hexanol (μg/g) | 1-octen-3-ol (μg/g) | 2,4 decadienal (μg/g) | 2,4 decadienal, hexanal, hexanol (μg/g) |
|---|---|---|---|---|---|---|
| G-6 | 3.2 | 31.7 | 1.6 | 8.9 | 16.7 | 50.1 |
| J-23 | 2.9 | 30.0 | 5.1 | 6.9 | 15.0 | 50.1 |
| F-35 | 2.9 | 28.8 | 1.2 | 6.5 | 20.4 | 50.4 |
| I-5 | 2.8 | 30.4 | 5.1 | 3.1 | 15.0 | 50.6 |
| G-20 | 4.0 | 23.8 | 5.0 | 5.3 | 22.0 | 50.8 |
| J-29 | 3.0 | 31.3 | 5.1 | 4.5 | 14.6 | 51.0 |
| G-13 | 4.4 | 35.8 | 3.8 | 4.8 | 11.5 | 51.0 |
| I-0 | 3.0 | 32.7 | 5.1 | 4.1 | 13.3 | 51.1 |
| H-2 | 2.8 | 34.0 | 5.1 | 3.2 | 12.6 | 51.7 |
| G-18 | 3.9 | 27.6 | 4.4 | 4.5 | 19.9 | 51.9 |

TABLE 12 A 4

| Cross Type | Linolenic acid (%) | Hexanal (μg/g) | Hexanol (μg/g) | 1-octen-3-ol (μg/g) | 2,4 decadienal (μg/g) | 2,4 decadienal, hexanal, hexanol (μg/g) |
|---|---|---|---|---|---|---|
| H-3 | 3.0 | 28.6 | 5.1 | 3.3 | 18.5 | 52.2 |
| F-18 | 2.9 | 33.3 | 5.1 | 4.5 | 14.0 | 52.4 |
| F-26 | 4.6 | 31.4 | 1.6 | 4.5 | 19.3 | 52.4 |
| G-4 | 3.1 | 28.7 | 2.4 | 7.6 | 21.4 | 52.5 |
| J-9 | 3.5 | 29.9 | 5.1 | 5.4 | 17.7 | 52.7 |
| J-31 | 3.0 | 33.6 | 5.1 | 4.7 | 14.1 | 52.8 |
| J-27 | 3.1 | 34.5 | 5.1 | 5.9 | 13.9 | 53.5 |
| G-7 | 2.6 | 32.2 | 5.1 | 8.8 | 16.3 | 53.6 |
| J-24 | 3.1 | 31.1 | 5.1 | 6.2 | 17.7 | 53.9 |
| I-1 | 2.9 | 32.1 | 5.1 | 4.5 | 17.0 | 54.2 |
| I-2 | 3.0 | 32.1 | 5.1 | 4.8 | 17.2 | 54.3 |
| I-3 | 2.9 | 34.0 | 5.1 | 5.2 | 16.2 | 55.3 |
| J-11 | 3.3 | 34.8 | 5.1 | 6.2 | 16.1 | 55.9 |
| G-1 | 2.7 | 29.8 | 4.2 | 5.4 | 22.2 | 56.1 |
| H-4 | 2.9 | 36.0 | 5.1 | 3.8 | 16.1 | 57.2 |
| I-9 | 3.1 | 30.4 | 5.1 | 4.7 | 22.0 | 57.4 |
| F-14 | 4.3 | 41.7 | 2.0 | 4.4 | 13.8 | 57.5 |
| J-10 | 3.1 | 35.8 | 5.1 | 4.8 | 17.3 | 58.2 |
| J-25 | 3.1 | 37.6 | 5.1 | 7.0 | 16.7 | 59.3 |
| J-28 | 3.1 | 38.3 | 5.1 | 4.8 | 16.1 | 59.5 |
| J-18 | 3.3 | 39.1 | 2.4 | 7.8 | 18.2 | 59.6 |
| J-21 | 3.1 | 37.7 | 5.1 | 5.3 | 17.1 | 59.9 |
| J-22 | 3.2 | 38.0 | 5.1 | 7.2 | 16.9 | 60.0 |
| F-30 | 3.1 | 35.7 | 0.8 | 13.2 | 23.8 | 60.2 |
| J-26 | 3.1 | 37.1 | 5.1 | 5.2 | 19.0 | 61.2 |
| J-8 | 3.3 | 37.6 | 5.1 | 5.5 | 18.9 | 61.6 |
| J-7 | 3.2 | 38.6 | 5.1 | 5.5 | 18.3 | 62.0 |
| F-12 | 4.8 | 36.5 | 5.1 | 3.9 | 21.0 | 62.5 |
| G-3 | 2.9 | 32.6 | 2.5 | 9.8 | 27.7 | 62.7 |
| F-28 | 2.9 | 43.5 | 2.4 | 6.2 | 16.9 | 62.8 |
| F-24 | 4.4 | 42.0 | 3.5 | 6.4 | 18.3 | 63.7 |
| F-34 | 3.0 | 35.3 | 1.5 | 7.8 | 27.0 | 63.8 |
| E-19 | 3.0 | 40.9 | 4.6 | 1.7 | 19.3 | 64.8 |
| F-29 | 3.6 | 42.0 | 3.5 | 4.6 | 20.8 | 66.2 |
| E-12 | 2.8 | 39.9 | 5.1 | 4.4 | 21.8 | 66.7 |
| J-20 | 2.9 | 41.5 | 5.1 | 5.3 | 21.5 | 68.1 |
| F-27 | 2.9 | 42.1 | 0.9 | 8.1 | 26.5 | 69.6 |
| F-11 | 3.6 | 41.3 | 5.1 | 3.5 | 23.7 | 70.1 |
| F-9 | 4.6 | 46.7 | 1.4 | 5.2 | 21.9 | 70.1 |
| F-16 | 4.1 | 42.8 | 5.1 | 4.5 | 22.5 | 70.4 |
| F-15 | 3.7 | 54.5 | 2.2 | 6.7 | 25.8 | 82.5 |

TABLE 13

Formation of 1-octen-3-ol in odor assay was reduced when soybeans were dehulled prior to making soy flour.

| Soybean 14 | 1-octen-3-ol(µg/µg) | | |
|---|---|---|---|
| | Whole seed | Dehulled | Dehulled Stdev |
| J-2 | 4.39 | 2.17 | 0.13 |
| J-1 | 5.08 | 2.25 | 0 |
| J-3 | 6.26 | 2.36 | |
| j-4 | 4.27 | 1.35 | 0 |
| HiBC | 10.36 | 3.19 | 0.09 |

EXAMPLE 7

Effects of pH on Odor Formation

A standard odor assay provided by the invention involved the addition of soy flour to water, resulting in odor formation at about pH 6.3. The purpose of the following experiment was to determine if varieties that produce low levels of odors under this condition also produce low levels of odors under other pH conditions. The odor producing properties of a commercial control soybean were compared with a low odor producing line (A-4). Line A-4 produced lower levels of decadienal and hexanal at pH 3.0 and pH 5.5, and pH 7 and pH 9.2 (Table 14). These data support the use of the assay without buffer as a method for selecting soybeans that will produce low levels of odors over a wide range of pH conditions. The highest concentrations of hexanal and 2,4 decadienal were produced at pH 9, the pH where the least amount of 1-octen-3-ol was produced (Table 14).

TABLE 14

Effects of pH on formation of odors from commodity control and low odor producing soybean (A-4 of FIGS. 4 and 5 harvested in 2003). Odor assay use for this measure was the same as in example 1 except soy flour was added to 0.1 M $K_2HPO_4$ at the respective pH (3.02, 5.45, 7.01, and 9.16).

| | Decadienal (µg/g) | | | | Hexanal (µg/g) | | | | 1-octen-3-=ol (µg/g) | | | |
|---|---|---|---|---|---|---|---|---|---|---|---|---|
| pH | Control | Stdev | A-4 | Stdev | Control | Stdev | A-4 | Stdev | Control | Stdev | A-4 | stdev |
| 3.02 | 3.60 | 0.98 | 1.79 | 0.96 | 18.47 | 4.40 | 7.35 | 0.76 | 13.37 | 7.86 | 11.71 | 2.79 |
| 5.45 | 8.03 | 1.97 | 3.65 | 2.27 | 36.49 | 2.66 | 11.30 | 1.78 | 12.41 | 6.56 | 8.06 | 3.62 |
| 7.01 | 8.10 | 1.90 | 3.51 | 0.64 | 30.75 | 9.50 | 10.68 | 0.74 | 10.57 | 4.17 | 6.03 | 3.87 |
| 9.20 | 37.72 | 33.17 | 9.12 | 3.66 | 60.38 | 30.20 | 27.93 | 6.11 | 2.10 | 1.71 | 2.98 | 1.67 |

EXAMPLE 8

Effects of Soybean Protein Composition on Soymilk Sediment

This example describes the lower levels of sediment formed in soymilk made from soybeans having the modified protein composition of the invention. Protein-containing sediment has a negative impact on the organoleptic quality of soymilk as it is not desired to feel particles in beverages.

Soymilk preparation. A control low odor soybean (A-4) and a soybean having about 39% β-conglycinin and about 13% glycinin were ground using a Mega Grinder to make soy flour. Each flour sample was added to 36.75 grams of water (4° C.) in a 50 mL disposable polypropylene centrifuge tube so the final concentration of protein in the mixtures were 3.3% weight basis and sonicated for 15 sec at output power control setting of 8. The sonicated samples were centrifuged for 10 minutes at 8,000 rpm at 4° C. using the Eppendorf Centrifuge 5804 R. The supernatants (soymilk) were decanted into 50 ml disposable polypropylene centrifuge tubes. A portion of each soymilk (27.25 grams) was transferred to another 50 ml disposal centrifuge tube. The above samples were prepared in duplicate to accommodate the following variation in sucrose addition. Sucrose (0.6987 grams) was added to the 27.25 grams of soymilk either before or after heat-treatment.

Soymilk samples were heat-treated by placing the 50 ml disposal polypropylene centrifuge tube into the 95° C. silicon oil bath for 5 minutes, then the samples were transferred to an ice bath to cool, followed by refrigerated storage for 30 days. Sediment formed in the soymilk samples over time. The amount of sediment formed was quantified as follows. The sediment in the bottom of the centrifuge tubes were dispersed by tipping the tubes back and forth. The soymilk samples were transferred into a weighed centrifuge tube and the final weight was recorded. The tubes were placed into the Eppendorf Centrifuge 5804 R and centrifuged for 2 minutes at 8,000 rpm at 25° C. The soymilk supernatant was decanted and the weight of the sediment remaining was calculated. The amount of sediment was recorded as percentage of soymilk weight (% Sediment=100×Wt of Sediment/Wt of Soymilk).

Results. The control soymilks had at least twice as much sediment as the high β-conglycinin soymilks (Table 15).

TABLE 15

Effects of soybean protein composition on soymilk sediment. A-4 is control soybean. HBC is a high β-conglycinin, low glycinin soybean

| Soybean Type | Sucrose addition | % Sediment |
|---|---|---|
| A-4 | Before heating | 1.8 |
| A-4 | After heating | 2.0 |
| HBC | Before heating | 0.7 |
| HBC | After heating | 1.0 |

The above examples show that unique compositions were created that can produce low levels of odors even when soybeans contained lipoxygenases 1, 2 and 3. Also demonstrated was the ability to select soybeans that have improved organoleptic properties where soybeans were selected based on the amounts of glycinin proteins, free arginine and asparagine, yellow pigments and polyunsaturated fatty acids in the soybeans and the amounts of the odors 2,4 decadienal, hexanal, hexanol, and 1-octen-3-ol produced by the aqueous ground soybean suspensions. A method was disclosed for estimating the potential for soybeans to produce 2,4 decadienal, hexanal, hexanol and 1-octen-3-ol and other even more potent odors in soybean ingredients and foods. In this method of estimation of soybean odors, the value of incubated the soy flour in water at a 1 to 4 ratio resulted in original observations that 2,4 decadienal forms rapidly at room temperature in the suspensions and that it is possible to breed soybeans containing lipoxygenases 1, 2 and 3 that produce very low levels of odors.

It was also shown in the examples that it is possible to create endogenous soy compositions having greater than 30% β-conglycinins and less than 25% glycinins that have normal or low free arginine and free asparagine. It was further demonstrated that low odor and color properties can be combined with high β-conglycinin compositions and further combinations were conceived with low linolenic and mid-oleic soybeans. Glycinins are a source of insoluble proteins in soy ingredients and foods, creating sediment in beverages and undesirable mouthfeel. Free arginine and asparagine can form ammonia during processing which further react with odor compounds such as 2,4 decadienal to form potent odors such as 2 pentyl pyridine. Linoleic and linolenic acids are polyunsaturated fatty acids that are substrates for odor formation; lowering their content in soybeans will help lower formation of odors. Pigments of soybeans contribute to the off-color of soybean products, further impacting the organoleptic response. All together, the high β-conglycinin, low free arginine and asparagine, low odor and low color and low polyunsaturated fatty acid soybean composition is the most valued composition of the invention for creating soy protein ingredients and foods that are organoleptically pleasing. It is also recognized that these compositions will not lack the health properties associated with soy protein ingredients as β-conglycinins are associated with the cholesterol and triglyceride lowering properties of soy protein (Duranti et al., 2004) and in the inhibition of artherosclerosis (Adams et al., 2004).

EXAMPLE 9

Additional Sedimentation Analysis of Low Odor Soy Compositions

The study in Example 8 was repeated with the following changes. A commodity soybean control was included (AG3302). The soybeans were dehulled before making flour and the flour was sifted prior to addition to water. The supernatants (soymilk) were transferred to preweighed weighed centrifuge tubes. Sucrose was added before heat-treatment to make the final sucrose concentration 2.5% (w/w basis). The samples were stored in a refrigerator for 21 days. The heights of soymilk sediments in the centrifuge tubes were measured, then samples were centrifuged for 5 minutes at 8,000 rpm. The supernatants were decanted and weighed, the pH of the supernatants were determined (all samples had pH=6.7), and the tubes containing pellet were weighed. The weight percent of the wet soy sediments were calculated for each sample (weight % of wet soy sediment=100×weight of wet soy sediment/(weight of wet soy sediment+weight of soy supernatant).

The beneficial effects of the HBC and low odor soybeans in reducing protein sediment formation were found using dehulled soybeans (Table 16). The HBC soymilk had a 2.2 fold reduction of sediment compared to the low odor soybean line and a 7 fold reduction of sediment compared to control soybean. A surprising 3.1 fold reduction was found in sediment in the low odor soybean compared to the control. It is possible that the low odor trait reduced sediment formation by limiting free radical formation and protein oxidation. This therefore indicated the further beneficial properties of the optimized composition combining high β-conglycinin and low odor traits.

TABLE 16

Effects of high beta-conglycinin and low odor traits on soymilk sediment height and sediment-pellet weight compared to a control soybean compositions

|  | Sediment Height (mm) | Pellet weight (%) | Pellet wt. Stdev |
|---|---|---|---|
| HBC | 0 | 2.1 | 0.14 |
| A-4 | 8 | 4.7 | 0.42 |
| Control | 14 | 14.8 | 2.8 |

EXAMPLE 9

Preparation of Dehulled Soybean Flour and Isolated Soy Protein Ingredient

A control soybean (AG3302) and soybeans comprising greater than 30% of the total proteins as beta-conglycinins and less than 25% of the total proteins as glycinins and less than 2500 micrograms/g of free arginine plus asparagine (DJB2104GOR, EXP319AP) were dehulled to make dehull-soybean flour and then further processed to make isolated soy protein ingredient according the steps below.

TABLE 17

Composition of beta-conglycinins and glycinins in different soybean lines.

| Soybean line | Beta-conglycinins (% of total protein) | Glycinins (% of total protein) | Free Arg (ug/g) | Free Asn (ug/g) |
|---|---|---|---|---|
| AG3302 | 24.1 | 33.6 | 1455 | 155 |
| DJB1804BOR | 33.9 | 12.9 | 1230 | 93 |
| EXP319AP | 40.1 | 12.5 | 2197 | 224 |

1. Adjust soybeans to about 10% moisture and temper at room temperature.
2. Crack soybeans by using a cracking mill.
3. Dehull the cracked soybeans by using an Aspirator.
4. Condition the cracked and dehulled soybeans at 50-60 degrees C. by using a cooker.
5. Flake the conditioned soybeans using a Flaking Mill.
6. Extract soybean flakes with hexane.
7. Desolventize the defatted soybean meal, resulting in flakes.
8. Flakes were ground to make flour.
9. Water was added to a 300 liter jacked tank and adjusted to 50 degrees C. and pH 9.0 using 40% NaOH. Defatted soybean flour was added and mixed. The water to soy flour ratio was 12/1 (w/w). Extraction time was 45 minutes.
10. The solubilized soy protein was recovered from the extraction slurry by using a desludging disk centrifuge (back pressure, 58-60 psi).
11. The clarified protein solution was adjusted to pH 4.5 by adding hydrochloric acid (18%) and allowed to react for 30 minutes at 45 degrees C.
12. The precipitated protein was recovered using a desludging disk centrifuge.

13. The protein curd was washed two times using acidified water (pH 4.5+/−0.1, 30-35 degrees C.). Ratio of washing water to packed wet solids was 6:1 (w/w). The protein curd was recovered using a desludging disk centrifuge after each washing (back pressure, 58-60 psi).

14. The washed curd was mixed with sodium hydroxide (30%) to adjust pH to 6.8 using 30% NaOH and then heat treated at 116 degrees C. for 7.5 seconds. Then the pH was adjusted to pH 6.8.

15. The protein solution was adjusted to 45-55 degrees C. and was spray dried using an inlet air temperature of 204-215 degrees C., outlet air temperature of 82-88 degrees C.

16. The Nitrogen solubility index of the isolate soy protein ingredients were determined. A portion of sample was suspended in water with stirring at 30° C. for two hours. It was then diluted to a known volume with water. A portion of sample extract was centrifuged and an aliquot analyzed for protein. A separate portion of sample was analyzed for total protein by the same method. Water-soluble protein was calculated as a percent of total protein, which was proportional to water-soluble nitrogen as a percent of total nitrogen.

Results:

The nitrogen solubility index of the of soy protein powders (Table 18) were directly proportional to the amounts of beta-conglycinin in the soybeans used to make the soy protein ingredients: NSI=1.4716(% beta-conglycinin)+7.4502; R-squared=0.9975. A reduction in the levels of insoluble protein improves the organoleptic quality (e.g. smoother more refreshing mouthfeel) of food products which are formulated with the soy protein ingredients.

TABLE 18

Nitrogen Solubility Index

| Soybean line used to make Isolated Soy Protein. | NSI (%) | Standard Deviation |
|---|---|---|
| AG3302 | 42.7 | 2.5 |
| DJB1804BOR | 58.0 | 2.5 |
| EXP319AP | 66.0 | 2.3 |

The amino acid composition of the isolated soy protein ingredients made from soybeans had similar amino acid composition with the exception that the lysine content of the high beta-conglycinin (HBC) ingredients were about 6% higher than the control.

TABLE 19

Total amino acid composition of isolated soy protein ingredients.

| | AG3302 | DJB1804BOR | EXP319AP |
|---|---|---|---|
| Aspartic | 114.5 | 111.2 | 114.7 |
| Threonine | 37.6 | 37.3 | 36.8 |
| Serine | 50.8 | 52.0 | 52.7 |
| Glutamic | 203.3 | 192.0 | 202.2 |
| Proline | 55.5 | 53.8 | 55.2 |
| Glycine | 41.6 | 40.0 | 39.8 |
| Alanine | 42.9 | 42.2 | 41.9 |
| Valine | 49.1 | 49.6 | 49.7 |
| Methionine | 13.3 | 13.1 | 12.3 |
| Isoleucine | 44.3 | 44.5 | 44.9 |
| Leucine | 81.1 | 81.3 | 82.6 |
| Tyrosine | 38.4 | 39.1 | 39.3 |
| Phenylalanine | 50.9 | 51.8 | 53.7 |
| Histidine | 23.7 | 25.9 | 26.3 |
| Lysine | 62.3 | 65.4 | 66.5 |
| Arginine | 73.8 | 71.9 | 75.8 |
| Cysteine (after ox) | 13.1 | 14.6 | 13.6 |

TABLE 19-continued

Total amino acid composition of isolated soy protein ingredients.

| | AG3302 | DJB1804BOR | EXP319AP |
|---|---|---|---|
| Methionine (after ox) | 14.7 | 14.5 | 13.3 |
| Tryptophan | 12.1 | 12.0 | 11.4 |

EXAMPLE 10

Preparation of Cultured Soy Product from Dehulled Soybean Flour

Dehulled soybean flour was prepared from a commodity soybean (AG3302), a high beta-conglycinin soybean (DJB2104GOR) and a low odor producing soybean line (03JBK8-25), all harvested in the U.S. in 2004.

Methods use to prepare and test cultured product made from soybeans:

1. Soybeans were cracked using a cracking mill.
2. Cracked soybean seeds were dehulled using an aspirator.
3. The soybean meats (dehulled soybeans) were milled for 1 pass through a hammer mill and 5 passes through a pin mill.
4. Dehulled soybean flour was packaged plastic bags within fiber drums.
5. Protein content of the flour was determined.
6. Dehulled soybean flour (3 degrees C.) was added to water (3 degrees C.) so the protein content would be 3.5% (weight basis) and mixed using a hand held homogenizer for about 1 to 2 minutes.
7. Soy flour suspension was warmed in a plate heat exchanger and then injected with steam to treat the suspension at 141 degrees C. for 3.5 seconds and deaerated before cooling to about 4 degrees C.
8. Heat-treated suspensions were filtered to remove fiber, resulting in soymilk.
9. Dairy flavor ingredients, sugar (3%), and salt (0.2%) were added to the soymilk and mixed using a hand held homogenizer.
10. Flavored soymilk was warmed in a plate heat exchanger and then injected with steam to treat the suspension at 141 degrees C. for 3.5 seconds and deaerated before cooling to about 4 degrees C. and packaged in sterile containers.
11. Soymilk samples, each containing 2.2% protein, were weighed into sterilized, quart jars and warmed in the microwave from 45 to 60 seconds (about 24 degrees C.).
12. Sugar (3.1%), vanilla extract (0.4%) and cultured soy yogurt (*L. Bulgaricus, S. Thermophilus, L. Acidophilus, B. Bifidum, L. Casei, L. Rhamnosus*) (8%) were added to the soymilk and the samples were mixed.
13. Soymilk containing culture was placed in an incubator at 43 degrees C. and incubated to 4 hours, removed and refrigerated overnight (4 degrees C.).
14. The pH and viscosity measurements were taken on the refrigerated samples and a sensory evaluation was conducted by a 3 person panel who were blind to sample formulations. Viscosity was measured using a Brookfield viscometer with Spindle #3 at 20 rpms Results: The flavor profile of the cultured product made from DJB2104GOR was pleasant and would lend itself to a fruit flavored smoothie. The profile of the product made from 03JBK8-25 was pleasant and would lend itself well a sour cream or dip product. It was reasoned that a combination of high beta-conglycinin and low odor producing traits would also create pleasant cultured soymilk products. The lower viscosity of the high beta-conglycinin protein material may help in creating higher protein products at the same thickness level.

TABLE 20

Soybean composition and odor property.

| Soybean | Beta-conglycinins (% of total protein) | Glycinins (% of total protein) | Oil (Dry Matter Basis) | Protein (Dry Matter Basis) | Free Arg (ug/g) | Free Asn (ug/g) | Hexanal (ug/g) | Hexanol (ug/g) | 1-octen-3-ol (ug/g) | 2,4-decadienal (ug/g) |
|---|---|---|---|---|---|---|---|---|---|---|
| DJB2104GOR | 37.7 | 14.7 | 18.9 | 39.5 | 2197 | 142 | 8.8 | 3.17 | 5.9 | 11.7 |
| AG3302 | 24.1 | 33.6 | 22.4 | 38.1 | 1455 | 155 | 12.5 | 4.47 | 3.0 | 13.7 |
| 03JBK8-25 | 25.7 | 34.3 | 19.1 | 38.2 | 1711 | 116 | 2.6 | 1.39 | 3.3 | 5.6 |

TABLE 21

Flavor profile of the cultured product

| Sample Identification | Initial pH (4° C.) | Final pH (4° C.) | pH Change | Viscosity (Centipoise) | Sensory Comments |
|---|---|---|---|---|---|
| AG3302 | 6.828 | 4.629 | 2.199 | 2025 | Has a smoothie consistency, some coagulated bits, earthy, fermented flavor, tart, vanilla, cooked, not as sweet as others. |
| DJB2104GOR | 6.922 | 4.581 | 2.341 | 1095 | Thinner than other samples, sweet, "bright", balanced, vanilla comes through, tart. |
| 03JBK8-25 | 6.835 | 4.662 | 2.173 | 1948 | Thickest sample, rice pudding like texture, flavor like a sour cream, seems to be a different type of sour profile versus the others, fairly bland, some mouth drying. |

EXAMPLE 11

Demonstration of Combination of Low Odor and High β-Conglycinin

This example describes the combination of low odor producing properties with high β-conglycinin compositions. It demonstrates the ability to produce low odor soybean compositions comprising decreased glycinin and increased β-conglycinin content. Cross types such as A and E (Table 3) were combined with high beta-conglycinin germplasm having a pedigree of A3233/B2G2/A1923.

Protein analysis was carried out as follows: Eight soybean seeds were pooled and ground using the CAT Mega-Grinder (SOP Asci-01-0002). Ground samples were stored at 4° C. For analysis, ~30 mg of flour from each was weighed into one well of a 96 well 2 ml microtiter plate. Protein was extracted for 1 hour with shaking in 1.0 ml 1× Laemmli SDS buffer pH 6.8 containing 0.1M dithiothreitol (DTT) as a reluctant. Following centrifugation, a portion of each extract was further diluted in SDS buffer to yield 0.2-0.5 μg/μL total protein, heated to 90-100° C. for 10 min, and cooled. For each sample, 1-2 μg total protein was loaded using a 12 channel pipet onto a 26 lane 15% T gradient Tris/HCl Criterion gel. Molecular weight standards and a parental control were included in two of the lanes in each gel. The gels were electrophoresed until the tracking dye reached the bottom of the gel ~1.2 hrs, then stained overnight in Colloidal Coomassie Blue G-250, destained in DI water, and imaged using the GS800 Calibrated Densitometer. Quantitation was performed using Bio-Rad Quantity One™ Software. The software was used to determine the relative quantity of each band in the sample lane. The percent glycinin and percent β-conglycinin protein sub-unit bands are reported as the relative percent of the total protein in the lane. The a5-glycinin subunit was not quantitated and was not included in total acidic glycinin value. The sample identities and weights are tracked using Master LIMS™.

Low odor producing soybeans compositions with high β-conglycinin trait are illustrated along with some lines that did not have the low odor trait (Table 22). Duplicate odor analyses are shown for the first line in the table. Several lines are shown that lack glycinins and produced compositions with less than 20 μg/g of total 2,4 decadienal plus hexanal plus hexanal per gram of ground seeds following oxidation under mild aqueous conditions. The compositions produced will be further evaluated for other characteristics (e.g., yield, free amino acids, color and fatty acid composition).

TABLE 22

Odor producing and protein subunit makeup of high beta-conglycinin soybean compositions.

| Sample ID | hexanal (ug/g) | Hexanol (ug/g) | Hexanal + Hexanol (ug/g) | 1-octen-3-ol (ug/g) | 2,4 decadienal (ug/g) | Alpha' BC (%) | Alpha BC (%) | Beta BC (%) | AcGly (%) |
|---|---|---|---|---|---|---|---|---|---|
| JB0305620.0102.0001 | ND | 2.5 | 2.5 | 6.9 | 3.8 | 16.0 | 24.4 | 8.1 | 0.0 |
| JB0305620.0102.0001 | 4.4 | 2.5 | 7.0 | 8.2 | 4.0 | 16.0 | 24.4 | 8.1 | 0.0 |
| JB0305616.0349.0016 | 5.7 | 2.3 | 8.0 | 8.9 | 3.0 | 14.7 | 18.3 | 6.3 | 12.1 |
| JB0305597.0181.0008 | 7.1 | 2.2 | 9.4 | 5.4 | 3.0 | 14.0 | 15.2 | 4.4 | 5.0 |
| JB0305617.0178.0015 | 5.3 | 2.0 | 7.3 | 1.5 | 5.2 | 15.4 | 17.4 | 3.5 | 0.0 |
| JB0305618.0035.0025 | 7.2 | 1.7 | 8.9 | 8.9 | 3.8 | 16.4 | 19.2 | 6.6 | 0.0 |
| JB0305616.0349.0011 | 7.1 | 2.2 | 9.3 | 10.9 | 3.8 | 13.6 | 18.8 | 8.7 | 2.6 |

TABLE 22-continued

Odor producing and protein subunit makeup of high beta-conglycinin soybean compositions.

| Sample ID | hexanal (ug/g) | Hexanol (ug/g) | Hexanal + Hexanol (ug/g) | 1-octen-3-ol (ug/g) | 2,4 decadienal (ug/g) | Alpha' BC (%) | Alpha BC (%) | Beta BC (%) | AcGly (%) |
|---|---|---|---|---|---|---|---|---|---|
| JB0305611.0213.0020 | 5.9 | 2.7 | 8.6 | 9.9 | 4.5 | 15.3 | 18.5 | 5.7 | 1.2 |
| JB0305620.0102.0018 | 7.8 | 2.6 | 10.4 | 5.5 | 3.0 | 16.8 | 23.9 | 10.1 | 0.0 |
| JB0305620.0102.0004 | 7.9 | 2.3 | 10.2 | 9.7 | 3.3 | 16.0 | 23.0 | 9.0 | 0.0 |
| JB0305617.0094.0031 | 7.3 | 2.3 | 9.5 | 1.6 | 4.6 | 16.8 | 21.4 | 6.6 | 3.2 |
| JB0305617.0178.0010 | 8.0 | 1.9 | 9.9 | 12.1 | 4.4 | 14.8 | 16.3 | 3.4 | 0.0 |
| JB0305611.0098.0009 | 7.7 | 2.3 | 10.0 | 8.8 | 4.4 | 14.9 | 18.2 | 10.3 | 6.7 |
| JB0305611.0213.0004 | 7.3 | 2.2 | 9.5 | 12.7 | 5.0 | 14.0 | 16.1 | 4.1 | 0.9 |
| JB0305611.0380.0010 | 7.5 | 2.2 | 9.7 | 6.7 | 4.9 | 16.3 | 19.5 | 6.5 | 3.8 |
| JB0305611.0213.0022 | 7.0 | 2.4 | 9.4 | 11.6 | 5.3 | 13.6 | 15.4 | 6.0 | 1.6 |
| JB0305619.0275.0007 | 16.8 | 4.5 | 21.3 | 14.0 | 14.0 | 14.5 | 13.4 | 3.9 | 0.0 |
| JB0305620.0078.0012 | 19.4 | 9.2 | 28.6 | 4.5 | 7.5 | 17.0 | 18.7 | 7.7 | 0.0 |
| JB0305618.0035.0021 | 21.1 | 5.1 | 26.2 | 7.0 | 10.2 | 11.6 | 13.5 | 3.4 | 0.0 |
| JB0305618.0047.0021 | 20.5 | 4.2 | 24.7 | 16.5 | 12.2 | 12.5 | 13.5 | 2.3 | 0.0 |
| JB0305620.0282.0008 | 24.7 | 3.9 | 28.6 | 7.4 | 8.4 | 12.3 | 13.9 | 3.3 | 0.0 |

Gly = acidic glycinins. ND = not detectable.

DEPOSIT INFORMATION

A deposit of Monsanto Technology LLC, soybean 0119149 seed disclosed above and recited in the claims, has been made under the Budapest Treaty with the American Type Culture Collection (ATCC), 10801 University Boulevard, Manassas, Va. 20110. The deposited line 0119149 also has the designations "A-4" and "03JBK8-25", which are used herein in the working examples and tables. The ATCC accession number for the deposit is PTA-6197 and the date of deposit was Sep. 10, 2004. The deposit will be maintained in the depository for a period of 30 years, or 5 years after the last request, or for the effective life of the patent, whichever is longer, and will be replaced as necessary during that period.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,777,080
U.S. Pat. No. 5,981,781
U.S. Pat. No. 6,171,640
U.S. Pat. No. 6,171,640
U.S. Pat. No. 6,171,640.
U.S. Pat. No. 6,355,296
U.S. Pat. No. 6,444,874
U.S. Pat. No. 6,653,534.
U.S. Patent Appln. 20030074693
U.S. Patent Pub. 2003/0146313 A1
Adams et al., *J. Nutr.,* 134:511-516, 2004.
Bazzano et al., *Arch Intern. Med.,* 161:2573-2578, 2001.
Boatright and Lei, *J. Food Sci.,* 64:667-670, 1999.
Boatright et al., *JAOCS,* 75:1379-1383, 1998.
Boatright, *JAOCS,* 79:317-323, 2002.
Bradstreet, In: *The Kjeldahl Method for Organic Nitrogen,* Academic Press: NY, 1965.
Dahuja and Madaan, *Sci. Food Agric.,* 84:547-550, 2004.
Duranti et al., *J. Nutr.,* 134:1334-1339, 2004.
Edwin N. Frankel. Page 64-65, Lipid Oxidation; The Oily Press, LTD, Dundee, Scotland, 1988
Food and Drug Administration, Food labeling: Health claims; Soy Proteins and Coronary Diseases, Federal Register, 64(206):57699-57733, 1999.
Franzen and Kinsella, *Agric. Food Chem.,* 22:675-678, 1974.
Freese, *Successful Farming,* 97:7, 1999.
Hajika et al., *Jpn J. Breed.,* 41:507-509, 1991.
Hao et al., *Agricultural Sciences in China,* 1:965-971, 2002.
Hermansen et al., *Advances in Natural Therapy,* 20:50-78, 2003.
Husson et al., *J. Molecular Catalysis B: Enzymatic,* 5:159-163, 1998.
Joshi, *Chemical Innovation,* 19-24, 2000.
Jung et al., *J. Food Sci.,* 68:1287-1290, 2003.
Kalthoff and Sandell, In: *Quantitative Inorganic Analysis,* MacMillan, NY, 1948.
Kim et al., *J. Agric. Food Chem.,* 44:3906-3908, 1996.
Knize et al., *Fd Chem. Toxic,* 32:55-60, 1994.
Knowles and Briggs, In: *Introduction to Plant Breeding,* Reinhold Publication Corp., NY, 1967.
Kobayashi et al., *J. Agric. Food Chem.,* 43:2448-2452, 1995.
Kwok get al., *J. Food Engineering,* 40:15-20, 1999.
Lei and Boatright, *J. Food Sci.,* 68:1568-1572, 2003.
Lin et al., J; *Agric. Food Chem.,* 47, 2813-2821, 1999.
Lin, *Agric. Food Chem.,* 51:4364-4369, 2003.
Maheshwari et al., *J. Agric. Food Chem.,* 45:2488-2494, 1997.
Matsumura, *Food Chemistry,* 83:107-119, 2003.
McLeod and Ames, *Crit. Rev. Food Sci. Nutr.,* 27:219-402, 1988.
Minor et al., *JAOCS,* 72:1431-1434, 1995.
O'Keefe et al., *J. Food Sci.,* 56:802-806, 1991.

Obata and Matsuura, *Nipon Shokuhin Kagaku Kaishi,* 44:768-773, 1997.
Official Methods of Analysis of AOAC INTERNATIONAL, 17th Ed., Method 982.30, AOAC INTERNATIONAL: Gaithersburg, Md., 2000.
PCT Appln. WO 01/06866
Rackis, *Am. Oil Chem. Soc.,* 54:468, 1977.
Salete et al., *J. Agric. Food Chem.,* 51:1634-1639, 2003.
Samoto et al., *Biosci. Biotechnol. Biochem.,* 62:935-940, 1998.
Sinnecker et al., *J. Agric. Food Chem.,* 50:3961-3966, 2002.
Skarra and Miller, *Inform.,* 13:247-253, 2002.
SoySource, The United Soybean Board Sep. 16, 1999.
Takahashi et al., *Planta.,* 217:577-586, 2003.
Torres-Penaranda and Reitmeirer, *J. Food Sci.,* 66:352-356, 2001.
United States Department of Agriculture, *Energy Value of Food*, Agriculture Handbook No. 74, 2-11, 1973.
Utsumi et al., In: *Food Proteins and Their Applications*, Damodaran and Paraf (Eds.), Marcel Dekker, Inc., NY, 1997.
Warner et al. *J. Agric. Food Chem.,* 49:899-905, 2001.
Weel et al., *J. Agric. Food Chem.,* 50:5149-5155, 2002.
Wilson, In: *Lipoxygenase and Lipoxygenase Pathway Enzymes*, Piazza (Ed.), 209-225, 1996.
Wolfe and Cowan, In: *Soybean as a Food Source*, CRC Press, Inc., Boca Raton, Fla., 1975.
Wurzenberger and Grosch, *Biochim. Biophys. Acta,* 794:25-30, 1984.
Yuan, *Agric. Food Chem.,* 50:4953-4958, 2002.
Zhou and Boatright, *Food Sci.,* 64:852-854, 1999.
Zhou and Boatright, *J. Food Sci.,* 65:1155-1159, 2000.
Zhou et al., *J. Food Sci.,* 67:142-145, 2002.

What is claimed is:

1. A soybean meat composition produced from soybeans comprising lipoxygenases 1, 2 and 3, wherein the composition comprises greater than 10% linoleic acid as a percentage of total fatty acids and less than 20 μg of total 2,4 decadienal plus hexanal plus hexanol per gram following oxidation under mild aqueous conditions.

2. The composition of claim 1, comprising less than 4% linolenic acid as percent of total fatty acids.

3. The composition of claim 1, comprising less than 2000 μg per gram free arginine and less than 400 μg free asparagine per gram.

4. The composition of claim 1, having color measured as b* value of less than 30 and an L* value greater than 80, as monitored by the CIE-L*a*b* system where L* indicates lightness and b* indicates hue on a blue (−) to yellow (+) axis.

5. The composition of claim 1, comprising less than 4 μg of 1-octen-3-ol content per gram following oxidation under mild aqueous conditions.

6. The composition of claim 1, having greater than 30% of the protein as β-conglycinin.

7. The composition of claim 1, having less than 25% of the protein as glycinin.

8. The composition of claim 1, having a linoleic acid concentration between 10% and 60% of the total fatty acids.

9. A soybean meat composition having greater than 30% of the protein as β-conglycinin and less than 25% of the protein as glycinin, less than 5,000 μg per gram of free arginine, and less than 900 μg per gram free asparagine, further defined as comprising less than 4 μg per gram 1-octen-3-ol content following oxidation under mild aqueous conditions, or comprising less than 20 μg of total 2,4 decadienal plus hexanal plus hexanol per gram following oxidation under mild aqueous conditions.

10. The composition of claim 9, having less than 2,000 μg per gram of free arginine and less than 400 μg per gram free asparagine.

11. The composition of claim 9, having a linolenic acid concentration between 1.5% and 14% of the total fatty acids.

12. The composition of claim 9, having a linoleic acid concentration between 10% and 60% of the total fatty acids.

13. The composition of claim 9, having a color characterized by b* value less than 30 and an L* value greater than 80 as monitored by the CIE-L*a*b* system where L* indicates lightness and b* indicates hue on a blue (−) to yellow (+) axis.

14. The composition of claim 9, comprising 67-69 mg lysine per gram of protein.

15. The composition of claim 9, comprising 72-80 mg arginine per gram of protein.

16. The composition of claim 9, comprising 28-30 mg histidine per gram of protein.

17. A soybean meat composition having greater than 30% of the protein as β-conglycinin and less than 25% of the protein as glycinin and less than 20 μg of total 2,4 decadienal plus hexanal plus hexanol per gram following oxidation under mild aqueous conditions.

18. The composition of claim 17, having a linolenic acid concentration between 1.5% and 14% of the total fatty acids.

19. The composition of claim 17, having a linoleic acid concentration between 10% and 60% of the total fatty acids.

20. The composition of claim 17, having a color characterized by b* value less than 30 and an L* value greater than 80 as monitored by the CIE-L*a*b* system where L* indicates lightness and b* indicates hue on a blue (−) to yellow (+) axis.

* * * * *